(12) United States Patent
Maclellan et al.

(10) Patent No.: US 11,331,377 B2
(45) Date of Patent: May 17, 2022

(54) VECTORS AND METHODS FOR REGENERATIVE THERAPY

(71) Applicant: UNIVERSITY OF WASHINGTON, Seattle, WA (US)

(72) Inventors: W. Robb Maclellan, Seattle, WA (US); Danny El-Nachef, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 803 days.

(21) Appl. No.: 15/566,987

(22) PCT Filed: Apr. 20, 2016

(86) PCT No.: PCT/US2016/028459
§ 371 (c)(1),
(2) Date: Oct. 16, 2017

(87) PCT Pub. No.: WO2016/172224
PCT Pub. Date: Oct. 27, 2016

(65) Prior Publication Data
US 2018/0117125 A1 May 3, 2018

Related U.S. Application Data

(60) Provisional application No. 62/150,159, filed on Apr. 20, 2015.

(51) Int. Cl.
| A61K 48/00 | (2006.01) |
| A61K 38/44 | (2006.01) |
| C12N 9/02 | (2006.01) |
| A61K 35/34 | (2015.01) |
| A61K 9/00 | (2006.01) |
| C12N 5/077 | (2010.01) |
| A61K 38/00 | (2006.01) |

(52) U.S. Cl.
CPC ............ *A61K 38/44* (2013.01); *A61K 9/0019* (2013.01); *A61K 35/34* (2013.01); *A61K 48/0058* (2013.01); *C12N 5/0657* (2013.01); *C12N 9/0071* (2013.01); *C12Y 114/11* (2013.01); *A61K 38/00* (2013.01); *C12N 2750/14144* (2013.01)

(58) Field of Classification Search
None
See application file for complete search history.

(56) References Cited

U.S. PATENT DOCUMENTS

| 2009/0162329 A1 | 6/2009 | Anversa et al. |
| 2013/0347136 A1 | 12/2013 | Emerson, Jr. et al. |
| 2014/0155339 A1 | 6/2014 | McCord et al. |

FOREIGN PATENT DOCUMENTS

| WO | WO2008116156 A2 | 9/2008 |
| WO | WO2014014518 A1 | 1/2014 |
| WO | WO2015048577 A3 | 9/2014 |

OTHER PUBLICATIONS

Khoury-Hadda et al., PNAS, Feb. 2014; pp. E728-E737.*
Khoury-Hadda et al, supplementary materiial, Feb. 2014, 11 pages.*
ClonTech, pTRE2 Vector information, 2006, 2 pages.*
Kieserman et al, 2019, J. AMer. Heart Assoc., 14 pages.*
Laflamme MA, Murry CE. Heart regeneration. Nature May 19, 2011;473(7347):326-35.
Li AH, Liu PP, Villarreal FJ, Garcia RA. Dynamic changes in myocardial matrix and relevance to disease: translational perspectives. Circ Res Feb. 28, 2014;114(5):916-27.
Nowbar AN, Howard JP, Finegold JA, Asaria P, Francis DP. 2014 global geographic analysis of mortality from ischaemic heart disease by country, age and income: statistics from World Health Organisation and United Nations. Int J Cardiol Jun. 15, 2014;174(2):293-8.
Jopling C, Sleep E, Raya M, Marti M, Raya A, Izpisua Belmonte JC. Zebrafish heart regeneration occurs by cardiomyocyte dedifferentiation and proliferation. Nature Mar. 25, 2010;464(7288):606-9.
Porrello ER, Mahmoud AI, Simpson E et al. Transient regenerative potential of the neonatal mouse heart. Science Feb. 25, 2011;331(6020):1078-80.
Porrello ER, Mahmoud AI, Simpson E et al. Regulation of neonatal and adult mammalian heart regeneration by the miR-15 family. Proc Natl Acad Sci U S A Jan. 2, 2013;110(1):187-92.
Xin M, Kim Y, Sutherland LB et al. Hippo pathway effector Yap promotes cardiac regeneration. Proc Natl Acad Sci U S A Aug. 20, 2013;110(34):13839-44.
Senyo SE, Steinhauser ML, Pizzimenti CL et al. Mammalian heart renewal by pre-existing cardiomyocytes. Nature Jan. 17, 2013;493(7432):433-6.
Bergmann O, Bhardwaj RD, Bernard S et al. Evidence for cardiomyocyte renewal in humans. Science Apr. 3, 2009;324(5923):98-102.
Sdek P, Zhao P, Wang Y et al. Rb and p130 control cell cycle gene silencing to maintain the postmitotic phenotype in cardiac myocytes. J Cell Biol Aug. 8, 2011;194(3):407-23.
Angelis E, Garcia A, Chan SS et al. A cyclin D2-Rb pathway regulates cardiac myocyte size and RNA polymerase III after biomechanical stress in adult myocardium Circ Res May 23, 2008;102(10):1222-9.

(Continued)

*Primary Examiner* — Michael D Burkhart
(74) *Attorney, Agent, or Firm* — Karen S. Canady; canady + lortz LLP

(57) ABSTRACT

An expression vector capable of disrupting the silencing of cell cycle genes in adult cells, such as adult cardiac myocytes and other quiescent cells in terminally differentiated tissues, comprising: (a) a nucleic acid sequence encoding lysine-specific demethylase 4D (KDM4D); (b) a promoter that induces or effects overexpression of KDM4D, wherein the promoter is operably linked to the nucleic acid sequence; and (c) a regulatory element that inducibly represses the overexpression of KDM4D. The vector can be administered to a subject in a method for inducing tissue-specific hyperplasia in a mammal, including cardiomyocyte proliferation. The method provides for regenerative therapy, including improving cardiac function after myocardial infarct and other forms of cardiac damage.

12 Claims, 18 Drawing Sheets
Specification includes a Sequence Listing.

(56) References Cited

OTHER PUBLICATIONS

Zhong W, Mao S, Tobis S et al. Hypertrophic growth in cardiac myocytes is mediated by Myc through a Cyclin D2-dependent pathway. EMBO J Aug. 23, 2006;25(16):3869-79.
Ahuja P, Sdek P, MacLellan WR. Cardiac myocyte cell cycle control in development, disease, and regeneration. Physiol Rev Apr. 2007;87(2):521-44.
Neufeld TP, Edgar BA. Connections between growth and the cell cycle. Curr Opin Cell Biol Dec. 1998;10(6):784-90.
He A, Ma Q, Cao J et al. Polycomb repressive complex 2 regulates normal development of the mouse heart. Circ Res Feb. 3, 2012;110(3):406-15.
Oyama K, El-Nachef D, Zhang Y, Sdek P, MacLellan WR. Epigenetic regulation of cardiac myocyte differentiation. Front Genet 2014;5:375.
Hohl M, Wagner M, Reil JC et al. HDAC4 controls histone methylation in response to elevated cardiac load. J Clin Invest Mar. 1, 2013;123(3):1359-70.
Lee S, Lee JW, Lee SK. UTX, a histone H3-lysine 27 demethylase, acts as a critical switch to activate the cardiac developmental program. Dev Cell Jan. 17, 2012;22(1):25-37.
Movassagh M, Choy MK, Knowles DA et al. Distinct epigenomic features in end-stage failing human hearts. Circulation Nov. 29, 2011;124(22):2411-22.
Eulalio A, Mano M, Dal FM et al. Functional screening identifies miRNAs inducing cardiac regeneration. Nature Dec. 20, 2012;492(7429):376-81.
Beisel C, Paro R. Silencing chromatin: comparing modes and mechanisms. Nat Rev Genet Feb. 2011; 12(2):123-35.
Musselman CA, Lalonde ME, Cote J, Kutateladze TG. Perceiving the epigenetic landscape through histone readers. Nat Struct Mol Biol Dec. 2012;19(12):1218-27.
Kouzarides T. Chromatin modifications and their function. Cell Feb. 23, 2007;128(4):693-705.
Filion GJ, van Bemmel JG, Braunschweig U et al. Systematic protein location mapping reveals five principal chromatin types in *Drosophila* cells. Cell Oct. 15, 2010;143(2):212-24.
Margueron R, Li G, Sarma K et al. Ezh1 and Ezh2 maintain repressive chromatin through different mechanisms. Mol Cell Nov. 21, 2008;32(4):503-18.
Tessarz P, Kouzarides T. Histone core modifications regulating nucleosome structure and dynamics. Nat Rev Mol Cell Biol Nov. 2014;15(11):703-8.
Simon M, North JA, Shimko JC et al. Histone fold modifications control nucleosome unwrapping and disassembly. Proc Natl Acad Sci U S A Aug. 2, 2011;108(31):12711-6.
Chandra T, Kirschner K, Thuret JY et al. Independence of repressive histone marks and chromatin compaction during senescent heterochromatic layer formation. Mol Cell Jul. 27, 2012;47(2):203-14.
Solovei I, Kreysing M, Lanctôt C et al. Nuclear architecture of rod photoreceptor cells adapts to vision in mammalian evolution. Cell Apr. 17, 2009;137(2):356-68.
Zhang R, Chen W, Adams PD. Molecular dissection of formation of senescence-associated heterochromatin foci. Mol Cell Biol Mar. 2007;27(6):2343-58.
Giacinti C, Giordano A. RB and cell cycle progression. Oncogene Aug. 28, 2006;25(38):5220-7.
Blais A, Dynlacht BD. E2F-associated chromatin modifiers and cell cycle control. Curr Opin Cell Biol Dec. 2007;19(6):658-62.
Gonzalo S, Garcia-Cao M, Fraga MF et al. Role of the RB1 family in stabilizing histone methylation at constitutive heterochromatin. Nat Cell Biol Apr. 2005;7(4):420-8.
MacAluso M, Montanari M, Giordano A. Rb family proteins as modulators of gene expression and new aspects regarding the interaction with chromatin remodeling enzymes. Oncogene Aug. 28, 2006;25(38):5263-7.
Bracken AP, Ciro M, Cocito A, Helin K. E2F target genes: unraveling the biology. Trends Biochem Sci Aug. 2004;29(8):409-17.

Blais A, van Oevelen CJ, Margueron R, Acosta-Alvear D, Dynlacht BD. Retinoblastoma tumor suppressor protein-dependent methylation of histone H3 lysine 27 is associated with irreversible cell cycle exit. J Cell Biol Dec. 31, 2007,179(7):1399-412.
Xiao G, Mao S, Baumgarten G et al. Inducible activation of c-Myc in adult myocardium in vivo provokes cardiac myocyte hypertrophy and reactivation of DNA synthesis. Circ Res Dec. 7, 2001;89(12):1122-9.
Dahiya A, Wong S, Gonzalo S, Gavin M, Dean DC. Linking the Rb and polycomb pathways. Mol Cell Sep. 2001;8(3):557-69.
Narita M, Nunez S, Heard E et al. Rb-mediated heterochromatin formation and silencing of E2F target genes during cellular senescence. Cell Jun. 13, 2003;113(6):703-16.
Whetstine JR, Nottke A, Lan F et al. Reversal of histone lysine trimethylation by the JMJD2 family of histone demethylases. Cell May 5, 2006;125(3):467-81.
Bannister AJ, Kouzarides T. Reversing histone methylation. Nature Aug. 25, 2005;436(7054):1103-6.
McManus KJ, Biron VL, Heit R, Underhill DA, Hendzel MJ. Dynamic changes in histone H3 lysine 9 methylations: identification of a mitosis-specific function for dynamic methylation in chromosome congression and segregation. J Biol Chem Mar. 31, 2006;281(13):8888-97.
Mosammaparast N, Shi Y. Reversal of histone methylation: biochemical and molecular mechanisms of histone demethylases. Annu Rev Biochem 2010;79:155-79.
Shi Y, Whetstine JR. Dynamic regulation of histone lysine methylation by demethylases. Mol Cell Jan. 12, 2007;25(1):1-14.
Berry WL, Shin S, Lightfoot SA, Janknecht R. Oncogenic features of the JMJD2A histone demethylase in breast cancer. Int J Oncol Nov. 2012;41(5):1701-6.
Berry WL, Janknecht R. KDM4/JMJD2 histone demethylases: epigenetic regulators in cancer cells. Cancer Res May 15, 2013;73(10):2936-42.
Kim TD, Oh S, Shin S, Janknecht R. Regulation of tumor suppressor p53 and HCT116 cell physiology by histone demethylase JMJD2D/KDM4D. PLoS One 2012;7(4):e34618.
Shin S, Janknecht R. Activation of androgen receptor by histone demethylases JMJD2A and JMJD2D. Biochem Biophys Res Commun Aug. 3, 2007;359(3):742-6.
Zhang QJ, Chen HZ, Wang L, Liu DP, Hill JA, Liu ZP. The histone trimethyllysine demethylase JMJD2A promotes cardiac hypertrophy in response to hypertrophic stimuli in mice. J Clin Invest Jun. 2011;121(6):2447-56.
Chen, G., Guy, C.T., Chen, H.W., Hu, N., Lee, E.Y., and Lee, W.H. (1996). Molecular cloning and developmental expression of mouse p130, a member of the retinoblastoma gene family. J. Biol. Chem. 271, 9567-9572. doi:10.1074/ibc.271.16.9567.
Chen, G., Zhu, J., Lv, T., Wu, G., Sun, H., Huang, X., et al. (2009). Spatiotemporal expression of histone acetyltransferases, p300 and CBP, in developing embryonic hearts. J. Biomed. Sci. 16, 24. doi:10.1186/1423-0127-16-24.
Chen, L., Ma, Y., Kim, E.Y., Yu, W., Schwartz, R.J., Qian, L., et al. (2012). Conditional ablation of Ezh2 in murine hearts reveals its essential roles in endocardial cushion formation, cardiomyocyte proliferation and survival. PLoS ONE 7:e31005. doi: 10.1371/journal.pone.0031005.
Chen, T., and Dent, S.Y. (2014). Chromatin modifiers and remodellers: regulators of cellular differentiation. Nat. Rev. Genet. 15, 93-106. doi:10.1038/nrg3607.
Chuang, J.Y., and Hung, J.J. (2011). Overexpression of HDAC1 induces cellular senescence by Sp1/PP2A/pRb pathway. Biochem. Biophys. Res. Commun. 407, 587-592. doi:10.1016/j.bbrc.2011.03.068.
Costantini, D.L., Arruda, E.P., Agarwal, P., Kim, K.H., Zhu, Y., Zhu, W., et al. (2005). The homeodomain transcription factor Irx5 establishes the mouse cardiac ventricular repolarization gradient. Cell 123, 347-358. doi:10.1016/j.cell.2005.08.004.
Dai, Y.S., Cserjesi, P., Markham, B.E., and Molkentin, J.D. (2002). The transcription factors GATA4 and dHAND physically interact to synergistically activate cardiac gene expression through a p300-dependent mechanism. J. Biol. Chem. 277, 24390-24398. doi:10.1074/jbc.M202490200.

(56) References Cited

OTHER PUBLICATIONS

Daniel, J.A., Pray-Grant, M.G., and Grant, P.A. (2005). Effector proteins for methylated histones: an expanding family. Cell Cycle 4, 919-926. doi: 10.4161/cc.4.7.1824.

Delgado-Olguín, P., Huang, Y., Li, X., Christodoulou, D., Seidman, C.E., Seidman, J.G., et al. (2012). Epigenetic repression of cardiac progenitor gene expression by Ezh2 is required for postnatal cardiac homeostasis. Nat. Genet. 44, 343-347. doi: 10.1038/ng.1068.

Diehl, F., Brown, M.A., van Amerongen, M.J., Novoyatleva, T., Wietelmann, A., Harriss, J., et al. (2010). Cardiac deletion of Smyd2 is dispensable for mouse heart development. PLoS ONE 5:e9748. doi:10.1371/journal.pone.0009748.

Eom, G.H., Nam, Y.S., Oh, J.G., Choe, N., Min, H.K., Yoo, E.K., et al. (2014). Regulation of acetylation of histone deacetylase 2 by p300/CBP-associated factor/histone deacetylase 5 in the development of cardiac hypertrophy. Circ. Res. 114, 1133 1143. doi:10.1161/CIRCRESAHA.114.303429.

Fujii, T., Tsunesumi, S., Yamaguchi, K., Watanabe, S., and Furukawa, Y. (2011). Smyd3 is required for the development of cardiac and skeletal muscle in zebrafish PLoS ONE 6:e23491. doi:10.1371/journal.pone.0023491.

Gonzalo, S., and Blasco, M.A. (2005). Role of Rb family in the epigenetic definition of chromatin. Cell Cycle 4, 752-755. doi:10.4161/cc.4.6.1720.

Gottlieb, P.D., Pierce, S.A., Sims, R.J., Yamagishi, H., Weihe, E.K., Harriss, J.V., et al. (2002). Bop encodes a muscle-restricted protein containing MYND and SET domains and is essential for cardiac differentiation and morphogenesis. Nat. Genet. 31, 25-32.

Grewal, S.I., and Jia, S. (2007). Heterochromatin revisited. Nat. Rev. Genet. 8, 35-46. doi: 10.1038/nrg2008.

Haberland, M., Montgomery, R.L., and Olson, E.N. (2009). The many roles of histone deacetylases in development and physiology: implications for disease and therapy. Nat. Rev. Genet. 10, 32-42. doi:10.1038/nrg2485.

Hasegawa, K., Meyers, M.B., and Kitsis, R.N. (1997). Transcriptional coactivator p300 stimulates cell type-specific gene expression in cardiac myocytes. J Biol Chem. 272, 20049-20054. doi:10.1074/jbc.272.32.20049.

Hathaway, N.A., Bell, O., Hodges, C., Miller, E.L., Neel, D.S., and Crabtree, G.R. (2012). Dynamics and memory of heterochromatin in living cells. Cell 149, 1447-1460. doi:10.1016/j.cell.2012.03.052.

He, A., Kong, S.W., Ma, Q., and Pu, W.T. (2011). Co-occupancy by multiple cardiac transcription factors identifies transcriptional enhancers active in heart Proc. Natl. Acad. Sci. U.S.A. 108, 5632-5637. doi:10.1073/pnas.1016959108.

He, A., Shen, X., Ma, Q., Cao, J., von Gise, A., Zhou, P., et al. (2012b). PRC2 directly methylates GATA4 and represses its transcriptional activity. Genes Dev. 26, 37-42. doi: 10.1101/gad.173930.111.

Hong, S., Cho, Y.W., Yu, L.R., Yu, H., Veenstra, T.D., and Ge, K. (2007). Identification of JmjC domain-containing UTX and JMJD3 as histone H3 lysine 27 demethylases. Proc. Natl. Acad. Sci. U.S.A. 104, 18439-18444. doi: 10.1073/pnas.0707292104.

Inagawa, M., Nakajima, K., Makino, T., Ogawa, S., Kojima, M., Ito, S., et al. (2013). Histone H3 lysine 9 methyltransferases, G9a and GLP are essential for cardiac morphogenesis. Mech. Dev. 130, 519-531. doi:10.1016/j.mod.2013.07.002.

James, T.C., and Elgin, S.C.R. (1986). Identification of a nonhistone chromosomal protein associated with heterochromatin in *Drosophila melanogaster* and its gene. Mol. Cell. Biol. 6, 3862-3872.

Johnson, A., Wu, R., Peetz, M., Gygi, S.P., and Moazed, D. (2013). Heterochromatic gene silencing by activator interference and a transcription elongation barrier. J Biol Chem. 288, 28771-28782. doi:10.1074/jbc.M113.460071.

Just, S., Meder, B., Berger, I.M., Etard, C., Trano, N., Patzel, E., et al. (2011). The myosin-interacting protein SMYD1 is essential for sarcomere organization. J. Cell Sci. 124, 3127-3136. doi:10.1242/jcs.084772.

Karamboulas, C., Swedani, A., Ward, C Al-Madhoun, A.S., Wilton, S., Boisvenue, S., et al. (2006). HDAC activity regulates entry of mesoderm cells into the cardiac muscle lineage. J. Cell Sci. 119, 4305-4314. doi:10 1242/jcs.03185.

Kawamura, T., Ono, K., Morimoto, T., Wada, H., Hirai, M., Hidaka, K., et al. (2005). Acetylation of GATA-4 is involved in the differentiation of embryonic stem cells into cardiac myocytes. J. Biol. Chem. 280, 19682-19688. doi:10.1074/jbc.M412428200.

Kellum, R. (2003). HP1 complexes and heterochromatin assembly. Curr. Top. Microbiol. Immunol. 274, 53-77. doi:10.1007/978-3-642-55747-7_3.

Klose, R.J., Kallin, E.M., and Zhang, Y. (2006). JmjC-domain-containing proteins and histone demethylation. Nat. Rev. Genet. 7, 715-727. doi:10.1038/nrg1945.

Kooistra, S.M., and Helin, K. (2012). Molecular mechanisms and potential functions of histone demethylases. Nat. Rev. Mol. Cell Biol. 13, 297-311. doi:10.1038/nrm3327.

Kotake, Y., Cao, R., Viatour, P., Sage, J., Zhang, Y., and Xiong, Y. (2007). pRB family proteins are required for H3K27 trimethylation and Polycomb repression complexes binding to and silencing p16INK4α tumor suppressor gene. Genes Dev. 21, 49-54.doi:10.1101/gad.1499407.

Lachner, M., O'Carroll, D., Rea, S., Mechtler, K., and Jenuwein, T. (2001). Methylation of histone H3 lysine 9 creates a binding site for HP1 proteins. Nature 410, 116-120. doi:10.1038/35065132.

Lagger, G., O'Carroll, D., Rembold, M., Khier, H., Tischler, J., Weitzer, G., et al. (2002). Essential function of histone deacetylase 1 in proliferation control and CDK inhibitor repression. EMBO J. 21, 2672-2681. doi:10.1093/emboj/21.11.2672.

Lai, A., Lee, J.M., Yang, W.M., DeCaprio, J.A., Kaelin, W.G. Jr., Seto, E., et al. (1999). RBP1 recruits both histone deacetylase-dependent and -independent repression activities to retinoblastoma family proteins. Mol. Cell. Biol. 19, 6632-6641.

Lan, F., Bayliss, P.E., Rinn, J.L., Whetstine, J.R., Wang, J.K., Chen, S., et al. (2007). A histone H3 lysine 27 demethylase regulates animal posterior development. Nature 449, 689-694. doi:10.1038/nature06192.

Lan, F., Nottke, A.C., and Shi, Y. (2008). Mechanisms involved in the regulation of histone lysine demethylases. Curr. Opin. Cell Biol. 20, 316-325.doi:10.1016/j.ceb.2008.03.004.

Li, G., and Reinberg, D. (2011). Chromatin higher-order structures and gene regulation. Curr. Opin. Genet. Dev. 21, 175-186. doi:10.1016/j.gde.2011.01.022.

Li, H., Zhong, Y., Wang, Z., Gao, J., Xu, J., Chu, W., et al. (2013). Smyd1b is required for skeletal and cardiac muscle function in zebrafish. Mol. Biol. Cell 24, 3511-3521. doi:10.1091/mbc.E13-06-0352.

Li, L., Zhu, J., Tian, J., Liu, X., and Feng, C. (2010). A role for Gcn5 in cardiomyocyte differentiation of rat mesenchymal stem cells. Mol. Cell. Biochem. 345, 309-316. doi: 10.1007/s11010-010-0586-3.

Lin, Q., Schwarz, J., Bucana, C., and Olson, E.N. (1997). Control of mouse cardiac morphogenesis and myogenesis by transcription factor MEF2C. Science 276, 1404 1407. doi:10.1126/science.276.5317.1404.

Luo, R.X., Postigo, A.A., and Dean, D.C. (1998). Rb interacts with histone deacetylase to repress transcription. Cell 92, 463-473. doi:10.1016/S0092-8674(00)80940-X.

Ma, K., Chan, J.K., Zhu, G., and Wu, Z. (2005). Myocyte enhancer factor 2 acetylation by p300 enhances its DNA binding activity, transcriptional activity, and myogenic differentiation. Mol. Cell. Biol. 25, 3575-3582. doi:10.1128/MCB.25.9.3575-3582.2005.

MacLellan, W.R., Garcia, A., Oh, H., Frenkel, P., Jordan, M.C., Roos, K.P., et al. 2005). Overlapping roles of pocket proteins in the myocardium are unmasked by germ line deletion of p130 plus heart-specific deletion of Rb. Mol. Cell. Biol. 25, 2486-2497. doi:10.1128/MCB.25.6.2486-2497.2005.

Magnaghi-Jaulin, L., Groisman, R., Naguibneva, I., Robin, P., Lorain, S., LeVillain, J.P., et al. (1998). Retinoblastoma protein represses transcription by recruiting a histone deacetylase. Nature 391, 601-605. doi:10.1038/35410.

Margueron, R., and Reinberg, D. (2011). The Polycomb complex PRC2 and its mark in life. Nature 469, 343-349. doi:10.1038/nature09784.

(56) References Cited

OTHER PUBLICATIONS

Mathiyalagan, P., Chang, L., Du, X.J., and El-Osta, A. (2010). Cardiac ventricular chambers are epigenetically distinguishable. Cell Cycle 9, 612-617. doi:10.4161/cc.9.3.10612.

May, D., Blow, M.J., Kaplan, T., McCulley, D.J., Jensen, B.C., Akiyama, J.A., et al. (2012). Large-scale discovery of enhancers from human heart tissue. Nat. Genet. 44, 89-93. doi:10.1038/ng.1006.

McFadden, D.G., Charité, J., Richardson, J.A., Srivastava, D., Firulli, A.B., and Olson, E.N. (2000). A GATA-dependent right ventricular enhancer Controls dHAND transcription in the developing heart. Development 127, 5331-5341.

Minc, E., Allory, Y., Courvalin, J.C., and Buendia, B. (2001). Immunolocalization of HP1 proteins in metaphasic mammalian chromosomes. Methods Cell Sci. 23, 171-174. doi:10.1023/A:1013168323754.

Minc, E., Allory, Y., Worman, H.J., Courvalin, J.C., and Buendia, B. (1999). Localization and phosphorylation of HP1 proteins during the cell cycle in mammalian cells. Chromosoma 108, 220-234. doi:10.1007/s004120050372.

Hillringhaus L, Yue WW, Rose NR et al. Structural and evolutionary basis for the dual substrate selectivity of human KDM4 histone demethylase family. J Biol Chem Dec. 2, 2011;286(48):41616-25.

Krishnan S, Trievel RC. Structural and functional analysis of JMJD2D reveals molecular basis for site-specific demethylation among JMJD2 demethylases. Structure Jan. 8, 2013;21(1):98-108.

Shin S, Janknecht R. Diversity within the JMJD2 histone demethylase family. Biochem Biophys Res Commun Feb. 23, 2007;353(4):973-7.

Zhang Y, Matsushita N, Eigler T, Marban E. Targeted MicroRNA Interference Promotes Postnatal Cardiac Cell Cycle Re-Entry. J Regen Med 2013;2:2.

Siedner S, Krüger M, Schroeter M et al. Developmental changes in contractility and sarcomeric proteins from the early embryonic to the adult stage in the mouse heart. J Physiol Apr. 15, 2003;548(Pt2):493-505.

Iwamori N, Zhao M, Meistrich ML, Matzuk MM. The testis-enriched histone demethylase, KDM4D, regulates methylation of histone H3 lysine 9 during spermatogenesis in the mouse but is dispensable for fertility. Biol Reprod Jun. 2011;84(6):1225-34.

Zhu Y, van Essen D, Saccani S. Cell-type-specific control of enhancer activity by H3K9 trimethylation. Mol Cell May 25, 2012;46(4):408-23.

Zhang Y, Li TS, Lee ST et al. Dedifferentiation and proliferation of mammalian cardiomyocytes. PLoS One 2010;5(9):e12559.

Peters AH, O'Carroll D, Scherthan H et al. Loss of the Suv39h histone methyltransferases impairs mammalian heterochromatin and genome stability. Cell Nov. 2, 2001;107(3):323-37.

Sanbe A, Gulick J, Hanks MC, Liang Q, Osinska H, Robbins J. Reengineering inducible cardiac-specific transgenesis with an attenuated myosin heavy chain promoter. Circ Res Apr. 4, 2003;92(6):609-16.

Schoeftner S, Blasco MA. A 'higher order' of telomere regulation: telomere heterochromatin and telomeric RNAs. EMBO J Aug. 19, 2009;28(16):2323-36.

Lange UC, Siebert S, Wossidlo M et al. Dissecting the role of H3K64me3 in mouse pericentromeric heterochromatin. Nat Commun 2013;4:2233.

Schotta G, Lachner M, Sarma K et al. A silencing pathway to induce H3-K9 and H4-K20 trimethylation at constitutive heterochromatin. Genes Dev Jun. 1, 2004;18(11):1251-62.

Kikuchi K, Holdway JE, Werdich AA et al. Primary contribution to zebrafish heart regeneration by gata4(+) cardiomyocytes. Nature Mar. 25, 2010;464(7288):601-5.

Purcell NH, Wilkins BJ, York A et al. Genetic inhibition of cardiac ERK1/2 promotes stress-induced apoptosis and heart failure but has no effect on hypertrophy in vivo. Proc Natl Acad Sci U S A Aug. 28, 2007;104(35):14074-9.

Milch RA, Rall DP, Tobie JE. Bone localization of the tetracyclines. J Natl Cancer Inst Jul. 1957;19(1):87-93.

Sánchez AR, Rogers RS, III, Sheridan PJ. Tetracycline and other tetracycline derivative staining of the teeth and oral cavity. Int J Dermatol Oct. 2004;43(10):709-15.

Mahmoud AI, Kocabas F, Muralidhar SA et al. Meis1 regulates postnatal cardiomyocyte cell cycle arrest. Nature May 9, 2013;497(7448):249-53.

Daub H, Olsen JV, Bairlein M et al. Kinase-selective enrichment enables quantitative phosphoproteomics of the kinome across the cell cycle. Mol Cell Aug. 8, 2008;31(3):438-48.

Muramatsu D, Singh PB, Kimura H, Tachibana M, Shinkai Y. Pericentric heterochromatin generated by HP1 protein interaction-defective histone methyltransferase Suv39h1. J Biol Chem Aug. 30, 2013;288(35):25285-96.

Peters AH, Kubicek S, Mechtler K et al. Partitioning and plasticity of repressive histone methylation states in mammalian chromatin. Mol Cell Dec. 2003;12(6):1577-89.

Black JC, Allen A, Van RC et al. Conserved antagonism between JMJD2A/KDM4A and HP1gamma during cell cycle progression. Mol Cell Dec. 10, 2010;40(5):736-48.

Barski A, Cuddapah S, Cui K et al. High-resolution profiling of histone methylations in the human genome. Cell May 18, 2007;129(4):823-37.

Hawkins RD, Hon GC, Lee LK et al. Distinct epigenomic landscapes of pluripotent and lineage-committed human cells. Cell Stem Cell May 7, 2010;6(5):479-91.

Mikkelsen TS, Ku M, Jaffe DB et al. Genome-wide maps of chromatin state in pluripotent and lineage-committed cells. Nature Aug. 2, 2007;448(7153):553-60.

Gray SG, Iglesias AH, Lizcano F et al. Functional characterization of JMJD2A, a histone deacetylase- and retinoblastoma-binding protein. J Biol Chem Aug. 5, 2005;280(31):28507-18.

Nielsen SJ, Schneider R, Bauer UM et al. Rb targets histone H3 methylation and HP1 to promoters. Nature Aug. 2, 2001;412(6846):561-5.

Rose BA, Force T, Wang Y. Mitogen-activated protein kinase signaling in the heart: angels versus demons in a heart-breaking tale. Physiol Rev Oct. 2010;90(4):1507-46.

Brattelid T, Winer LH, Levy FO, Liestøl K, Sejersted OM, Andersson KB. Reference gene alternatives to Gapdh in rodent and human heart failure gene expression studies. BMC Mol Biol 2010;11:22.

Kolwicz SC, Jr., Purohit S, Tian R. Cardiac metabolism and its interactions with contraction, growth, and survival of cardiomyocytes. Circ Res Aug. 16, 2013;113(5):603-16.

Agger, K., Cloos, P.A., Christensen, J., Pasini, D., Rose, S., Rappsilber, J., et al. (2007). UTX and JMJD3 are histone H3K27 demethylases involved in HOX gene regulation and development. Nature 449, 731-734. doi:10.1038/nature06145.

Ait-Si-Ali, S., Guasconi, V., Fritsch, L., Yahi, H., Sekhri, R., Naguibneva, I., et al. (2004). A Suv39h-dependent mechanism for silencing S-phase genes in differentiating but not in cycling cells. EMBO J. 23, 605-615. doi:10.1038/sj.emboj.7600074.

Angus, S. P., Mayhew, C.N., Solomon, D.A., Braden, W.A., Markey, M.P., Okuno, Y., et al. (2004). RB reversibly inhibits DNA replication via two temporally distinct mechanisms. Mol. Cell. Biol. 24, 5404-5420. doi:10.1128/MCB.24.12.5404-5420.2004.

Auth, T., Kunkel, E., and Grummt, F. (2006). Interaction between HP1α and replication proteins in mammalian cells. Exp. Cell Res. 312, 3349-3359. doi: 10.1016/j.yexcr.2006 07.014.

Backs, J., Worst, B.C., Lehmann, L.H., Patrick, D.M., Jebessa, Z., Kreusser, M. M., et al. (2011). Selective repression of MEF2 activity by PKA-dependent proteolysis of HDAC4. J. Cell Biol. 195, 403-415. doi:10.1083/jcb.201105063.

Bandyopadhyay, D., Curry, J. L., Lin, Q., Richards, H. W., Chen, D., Hornsby, P.J., et al. (2007). Dynamic assembly of chromatin complexes during cellular senescence: implications for the growth arrest of human melanocytic nevi. Aging Cell 6, 577-591. doi:10.1111/j.1474-9726.2007.00308.x.

Bannister, A. J., Zegerman, P., Partridge, J. F., Miska, E. A., Thomas, J. O., Allshire, R. C., et al. (2001). Selective recognition of methylated lysine 9 on histone H3 by the HP1 chromo domain. Nature 410, 120-124. doi:10.1038/35065138.

(56) References Cited

OTHER PUBLICATIONS

Bergemann, A.D., Cole, F., and Hirschhorn, K. (2005). The etiology of Wolf-Hirschhorn syndrome. Trends Genet. 21, 188-195. doi:10.1016/j.tig.2005.01.008.

Blow, M.J., McCulley, D.J., Li, Z. ,Zhang, T., Akiyama, J.A., Holt, A., et al. (2010). ChIP-Seq identification of weakly conserved heart enhancers Nat. Genet. 42, 806-810. doi:10.1038/ng.650.

Bose, J., Gruber, A.D., Helming, L., Schiebe, S., Wegener, I., Hafner, M., et al. (2004). The phosphatidylserine receptor has essential functions during embryogenesis but not in apoptotic cell removal. J. Biol. 3, 15. doi:10.1186/ibiol10.

Boyer, L.A., Plath, K., Zeitlinger, J., Brambrink, T., Medeiros, L.A., Lee, T.I., et al.(2006). Polycomb complexes repress developmental regulators in murine embryonic stem cells. Nature 441, 349-353. doi:10 1038/nature04733.

Brehm, A., Miska, E.A., McCance, D.J., Reid, J.L., Bannister, A.J., and Kouzarides, T. (1998). Retinoblastoma protein recruits histone deacetylase to repress transcription. Nature 391, 597-601. doi:10.1038/35404.

Breitbart, R.E., Nguyen, H.T., Medford, R.M., Destree, A.T., Mahdavi, V., and Nadal-Ginard, B. (1985). Intricate combinatorial patterns of exon splicing generate multiple regulated troponin T isoforms from a single gene. Cell 41, 67-82. doi: 10.1016/0092-8674(85)90062-5.

Brero, A., Easwaran, H.P., Nowak, D., Grunewald, I., Cremer, T., Leonhardt, H., et al. (2005). Methyl CpG-binding proteins induce large-scale chromatin reorganization during terminal differentiation. J. Cell Biol. 169, 733-743. doi: 10.1083/jcb.200502062.

Canzig, D., Liao, M., Naber, N., Pate, E., Larson, A., Wu, S., et al. (2013). A conformational switch in HP1 releases auto-inhibition to drive heterochromatin assembly. Nature 496, 377-381. doi:10.1038/nature12032.

Cao, R., Wang, L., Wang, H., Xia, L., Erdjument-Bromage, H., Tempst, P., et al. (2002). Role of histone H3 lysine 27 methylation Polycomb-group silencing. Science 298, 1039-1043. doi:10 1126/science.1076997.

Chang, B., Chen, Y., Zhao, Y., and Bruick, R.K. (2007). JMJD6 is a histone arginine demethylase. Science 318, 444-447. doi:10.1126/science.1145801.

Chang, S., McKinsey, T.A., Zhang, C.L., Richardson, J.A., Hill, J.A., and Olson, E.N. (2004). Histone deacetylases 5 and 9 govern responsiveness of the heart to a subset of stress signals and play redundant roles in heart development. Mol. Cell. Biol. 24, 8467-8476. doi:10.1128/MCB.24.19.8467-8476.2004.

Mollova, M., Bersell, K., Walsh, S., Savla, J., Das, L.T., Park, S.Y., et al. (2013). Cardiomyocyte proliferation contributes to heart growth in young humans. Proc. Natl. Acad. Sci. U.S.A. 110, 1446-1451. doi: 10.1073/pnas.1214608110.

Montgomery, R.L., Davis, C.A., Potthoff, M.J., Haberland, M., Fielitz, J., Qi,X., et al. (2007). Histone deacetylases 1 and 2 redundantly regulate cardiac morphogenesis, growth, and contractility. Genes Dev. 21, 1790-1802. doi:10.1101/gad.1563807.

Montgomery, R.L., Potthoff, M.J., Haberland, M., Qi, X., Matsuzaki, S., Humphries, K.M., et al. (2008). Maintenance of cardiac energy metabolism by histone deacetylase 3 in mice. J. Clin. Invest. 118, 3588-3597. doi:10.1172/JCI35847.

Nakayama, J., Rice, J.C., Strahl, B.D., Allis, C.D., and Grewal, S.I. (2001). Role of histone H3 lysine 9 methylation in epigenetic control of heterochromatin assembly. Science 292, 110-113. doi:10.1126/science.1060118.

Naqvi, N., Li, M., Calvert, J.W., Tejada, T., Lambert, J.P., Wu, J., et al. (2014). A proliferative burst during preadolescence establishes the final cardiomyocyte number. Cell 157, 795-807. doi:10.1016/j.cell.2014.03.035.

Nimura, K., Ura, K., Shiratori, H., Ikawa, M., Okabe, M., Schwartz, R.J., et al. (2009). A histone H3 lysine 36 trimethyltransferase links Nkx2-5 to Wolf-Hirschhorn syndrome. Nature 460, 287-291. doi:10.1038/nature08086.

Paige, S.L., Thomas, S., Stoick-Cooper, C.L., Wang, H., Maves, L., Sandstrom, R., et al. (2012). A temporal chromatin signature in human embryonic stem cells identifies regulators of cardiac development. Cell 151, 221-232. doi:10.1016/j.cell.2012.08.027.

Panteleeva, I., Boutillier, S., See, V., Spiller, D.G., Rouaux, C., Almouzni, G., et al. (2007). HP1α guides neuronal fate by timing E2F-targeted genes silencing during terminal differentiation. EMBO J. 26, 3616-3628. doi:10.1038/sj.emboj.7601789.

Papait, R., Cattaneo, P., Kunderfranco, P., Greco, C., Carullo, P., Guffanti A., et al. (2013). Genome-wide analysis of histone marks identifying an epigenetic signature of promoters and enhancers underlying cardiac hypertrophy. Proc. Natl. Acad. Sci. U.S.A. 110, 20164-20169. doi:10.1073/pnas.1315155110.

Park, C.Y., Pierce, S.A., Von Drehle, M., Ivey, K.N., Morgan, J.A., Blau, H.M., et al. (2010). skNAC, a Smyd1-interacting transcription factor, is involved in cardiac development and skeletal muscle growth and regeneration. Proc. Natl. Acad. Sci. U.S.A. 107, 20750-20755. doi:10.1073/pnas.1013493107.

Partanen, M., Motoyama, J., and Hui, C.C. (1999). Developmentally regulated expression of the transcriptional cofactors/histone acetyltransferases CBP and p300 during mouse embryogenesis. Int.J.Dev.Biol. 43, 487-494.

Pasini, D., Bracken, A.P., Hansen, J.B., Capillo, M., and Helin, K. (2007). The polycomb group protein Suz12 is required for embryonic stem cell differentiation. Mol. Cell. Biol. 27, 3769-3779. doi:10.1128/MCB.01432-06.

Poizat, C., Sartorelli, V., Chung, G., Kloner, R.A., and Kedes, L. (2000). Proteasome-mediated degradation of the coactivator p300 impairs cardiac transcription. Mol. Cell. Biol. 20, 8643-8654. doi:10.1128/MCB.20.23.8643-8654.2000.

Qiao, W., Zhang, W., Gai, Y., Zhao, L., and Fan, J. (2014). The histone acetyltransferase MOF overexpression blunts cardiac hypertrophy by targeting ROS in mice. Biochem. Biophys. Res. Commun. 448, 379-384. doi:10.1016/j.bbrc.2014.04.112.

Rada-Iglesias, A., Bajpai, R., Swigut, T., Brugmann, S.A., Flynn, R.A., and Wysocka, J. (2011). A unique chromatin signature uncovers early developmental enhancers in humans. Nature 470, 279-283. doi:10.1038/nature09692.

Robertson, K.D., Ait-Si-Ali, S., Yokochi, T., Wade, P.A., Jones, P.L., and Wolffe, A.P. (2000). DNMT1 forms a complex with Rb, E2F1 and HDAC1 and represses transcription from E2F-responsive promoters. Nat. Genet. 25, 338-342. doi:10.1038/77124.

Schlesinger, J., Schueler, M., Grunert, M., Fischer, J.J., Zhang, Q., Krueger, T., et al. (2011). The cardiac transcription network modulated by Gata4, Mef2a, Nkx2.5, Srf, histone modifications, and microRNAs. PLoS Genet. 7:e1001313. doi: 10.1371/journal.pgen.1001313.

Schneider, J.E., Böse, J., Bamforth, S.D., Gruber, A.D., Broadbent, C., Clarke, K., et al. (2004). Identification of cardiac malformations in mice lacking Ptdsr using a novel high-throughput magnetic resonance imaging technique. BMC Dev. Biol. 4:16. doi:10.1186/1471-213X-4-16.

Schueler, M., Zhang, Q., Schlesinger, J., Tönjes, M., and Sperling, S.R. (2012). Dynamics of Srf, p300 and histone modifications during cardiac maturation in mouse. Mol. Biosyst. 8, 495-503. doi:10.1039/c1mb05363a.

Sdek, P., Oyama, K., Angelis, E., Chan, S.S., Schenke-Layland, K., and MacLellan, W.R. (2013). Epigenetic regulation of myogenic gene expression by heterochromatin protein 1 alpha. PLoS ONE 8:e58319. doi:10.1371/journal.pone.0058319.

Sheikh, F., Raskin, A., Chu, P.H., Lange, S., Domenighetti, A.A., Zheng, M., et al. (2008). An FHL1-containing complex within the cardiomyocyte sarcomere mediates hypertrophic biomechanical stress responses in mice. J. Clin. Invest. 118, 3870-3880. doi:10.1172/JCI34472.

Shen, X., Liu, Y., Hsu, Y.J., Fujiwara, Y., Kim, J., Mao, X., et al. (2008). EZH1 mediates methylation on histone H3 lysine 27 and complements EZH2 in maintaining stem cell identity and executing pluripotency. Mol. Cell 32, 491-502. doi:10.1016/j.molcel.2008.10.016.

Shikama, N., Lutz, W., Kretzschmar, R., Sauter, N., Roth, J.F., Marino, S., et al. (2003). Essential function of p300 acetyltransferase activity in heart, lung and small intestine formation. EMBO J. 22, 5175-5185. doi:10.1093/emboj/cdg502.

(56) References Cited

OTHER PUBLICATIONS

Siddiqui, H., Fox, S.R., Gunawardena, R.W., and Knudsen, E.S. (2007). Loss of RB compromises specific heterochromatin modifications and modulates HP1α dynamics. J Cell. Physiol. 211, 131-137.doi:10.1002/jcp.20913.

Sims, R.J. III, Weihe, E.K., Zhu, L., O'Malley, S., Harriss, J.V., and Gottlieb, P.D. (2002). m-Bop, a repressor protein essential for cardiogenesis, interacts with skNAC, a heart- and muscle-specific transcription factor. J. Biol. Chem. 277, 26524-26529. doi:10.1074/jbc.M204121200.

Sirinupong, N., Brunzelle, J., Ye, J., Pirzada, A., Nico, L., and Yang, Z. (2010). Crystal structure of cardiac-specific histone methyltransferase SmyD1 reveals unusual active site architecture. J. Biol. Chem. 285, 40635-40644. doi:10.1074/jbc.M110.168187.

Slepak, T.I., Webster, K.A., Zang, J., Prentice, H., O'Dowd, A., Hicks, M. N., et al. (2001). Control of cardiac-specific transcription by p300 through myocyte enhancer factor-2D. J. Biol. Chem. 276, 7575-7585. doi:10.1074/jbc.M004625200.

Stadler, J.A., Shkumatava, A., Norton, W.H., Rau, M.J., Geisler, R., Fischer, S., et al. (2005). Histone deacetylase 1 is required for cell cycle exit and differentiation in the zebrafish retina. Dev. Dyn. 233, 883-889. doi:10.1002/dvdy.20427.

Stein, A.B., Jones, T.A., Herron, T.J., Patel, S.R., Day, S.M., Noujaim, S. F., et al. (2011). Loss of H3K4 methylation destabilizes gene expression patterns and physiological functions in adult murine cardiomyocytes. J. Clin. Invest. 121, 2641-2650. doi:10.1172/JCI44641.

Sun, H., Yang, X., Zhu, J., Lv, T., Chen, Y., Chen, G., et al. (2010). Inhibition of p300-HAT results in a reduced histone acetylation and down-regulation of gene expression in cardiac myocytes. Life Sci. 87, 707-714. doi:10.1016/j.lfs.2010.10.009.

Takeuchi, T., Watanabe, Y., Takano-Shimizu, T., and Kondo, S. (2006). Roles of jumonji and jumonji family genes in chromatin regulation and development. Dev. Dyn. 235, 2449-2459. doi:10.1002/dvdy.20851.

Tan, X., Rotllant, J., Li, H., Deyne, D.P., and Du, S.J. (2006). SmyD1, a histone methyltransferase, is required for myofibril organization and muscle contraction in zebrafish embryos. Proc. Natl. Acad. Sci. U.S.A. 103, 2713-2718. doi:10.1073/pnas.0509503103.

Tanaka, Y., Naruse, I., Hongo, T., Xu, M., Nakahata, T., Maekawa, T., et al. (2000). Extensive brain hemorrhage and embryonic lethality in a mouse null mutant of CREB-binding protein. Mech. Dev. 95, 133-145. doi:10.1016/S0925-4773(00)00360-9.

Tao, Y., Neppl, R.L., Huang, Z.P., Chen, J., Tang, R.H., Cao, R., et al. (2011). The histone methyltransferase Set7/9 promotes myoblast differentiation and myofibril assembly. J. Cell Biol. 194, 551-565. doi:10.1083/jcb.201010090.

Tonini, T., Bagella, L., D'Andrilli, G., Claudio, P.P., and Giordano, A. (2004). Ezh2 reduces the ability of HDAC1-dependent pRb2/p130 transcriptional repression of cyclin A. Oncogene 23, 4930-4937. doi:10.1038/sj.onc.1207608.

Trivedi, C.M., Lu, M.M., Wang, Q., and Epstein, J.A. (2008). Transgenic overexpression of Hdac3 in the heart produces increased postnatal cardiac myocyte proliferation but does not induce hypertrophy. J. Biol. Chem. 283, 26484-26489. doi:10.1074/jbc.M803686200.

Tsukada, Y., Fang, J., Erdjument-Bromage, H., Warren, M.E., Borchers, C.H., Tempst, P., et al. (2006). Histone demethylation by a family of JmjC domain containing proteins Nature 439, 811 816.doi:10.1038/nature04433.

Wamstad, J.A., Alexander, J.M., Truty, R.M., Shrikumar, A., Li, F., Eilertson, K.E., et al. (2012). Dynamic and coordinated epigenetic regulation of developmental transitions in the cardiac lineage. Cell 151, 206-220. doi:10.1016/j.cell.2012.07.035.

Wang, G.L., Salisbury, E., Shi, X., Timchenko, L., Medrano, E.E., and Timchenko, N.A. (2008). HDAC1 cooperates with C/EBPα in the inhibition of liver proliferation in old mice. J. Biol. Chem. 283, 26169-26178. doi:10.1074/jbc.M803544200.

Willis-Martinez, D., Richards, H.W., Timchenko, N.A., and Medrano, E.E. (2010). Role of HDAC1 in senescence, aging, and cancer. Exp. Gerontol. 45, 279-285. doi:10.1016/j.exger.2009.10.001.

Yamaguchi, M., Tonou-Fujimori, N., Komori, A., Maeda, R., Nojima, Y., Li, H., et al. (2005). Histone deacetylase 1 regulates retinal neurogenesis in zebrafish by suppressing Wnt and Notch signaling pathways. Development 132, 3027-3043. doi: 10.1242/dev.01881.

Yamamoto, K., and Sonoda, M. (2003). Self-interaction of heterochromatin protein 1 is required for direct binding to histone methyltransferase, SUV39H1 .Biochem. Biophys. Res. Commun. 301, 287-292. doi:10.1016/S0006-291X(02) 03021-8.

Yao, T.P., Oh, S.P., Fuchs, M., Zhou, N.D., Ch'ng, L.E., Newsome, D., et al. (1998). Gene dosage-dependent embryonic development and proliferation defects in mice lacking the transcriptional integrator p300. Cell 93, 361-372. doi: 10.1016/30092-8674(00)81165-4.

Ye, F., Chen, Y., Hoang, T., Montgomery, R.L., Zhao, X.H., Bu, H., et al. (2009). HDAC1 and HDAC2 regulate oligodendrocyte differentiation by disrupting the β-catenin-TCF interaction. Nat. Neurosci. 12, 829-838.doi:10.1038/nn.2333.

Zaidi, S., Choi, M., Wakimoto, H., Ma, L., Jiang, J., Overton, J.D., et al. (2013). De novo mutations in histone modifying genes in congenital heart disease. Nature 498, 220-223. doi:10.1038/nature12141.

Zhang, C.L., McKinsey, T.A., Chang, S., Antos, C.L., Hill, J.A., and Olson, E.N. (2002). Class II histone deacetylases act as signal-responsive repressors of cardiac hypertrophy. Cell 110, 479-488. doi:10 1016/30092-8674(02)00861-9.

Zhang, Y., Gao, Y., Zhao, L., Han, L., Lu, Y., Hou, P., et al. (2013). Mitogen-activated protein kinase p38 and retinoblastoma protein signalling is required for DNA damage-mediated formation of senescence-associated heterochromatic foci in tumour cells. FEBS J. 280, 4625-4639. doi:10.1111/febs.12435.

El-Nachef, Danny "H3K9me3 is Required for Adult Cardiac Myocyte Cell Cycle Exit and Gene Silencing In Vivo" International Society for Heart Research, Young Investigator Awards, Jun. 15, 2015, Seattle, Washington.

El-Nachef, Danny et al: "Repressive histone methylation regulates cardiac myocyte cell cycle exit", Journal of Molecular and Cellular Cardiology, vol. 121, 2018, pp. 1-12, XP085446456, ISSN: 0022-2828, DOI: 10.1016/J.YJMCC.2018.05.013.

El-Nachef, Danny: Epigenetic Regulation of Mammalian Cardiac Myocyte Cell Cycle, UCLA Electronic Theses and Dissertations, Jan. 1, 2016, https://escholarship.org/uc/item/2pq0h55c.

Oyama, Kyohei et al: "Regeneration potential of adult cardiacmyocytes", Cell Research—Xibao Yanjiu, vol. 23, No. 8, Jun. 18, 2013 (Jun. 18, 2013), pp. 978-979, XP55509191,GB, CN ISSN: 1001-0602, DOI: 10.1038/cr.2013.78.

Matoba, Shogo et al: "Embryonic Development following Somatic Cell Nuclear Transfer Impeded by Persisting Histone Methylation", Cell, Cell Press, Amsterdam, NL, vol. 159, No. 4, Oct. 30, 2014 (Oct. 30, 2014), pp. 884-895, XP029095123, ISSN: 0092-8674, DOI: 10.1016/J.CELL.2014.09.055.

Tae-Dong Kim et al: "Regulation of Tumor Suppressor p53 and HCT116 Cell Physiology by Histone Demethylase JMJD2D/KDM4D", PLOS ONE, vol. 7, No. 4, Jan. 1, 2012 (Jan. 1, 2012), p. e34618, XP55418471, DOI: 10.1371 /journal.pone.0034618.

Zoabi, Muhammad: "Supplementary Data RNA-dependent chromatin localization of KDM4D lysine demethylase promotes H3K9me3 demethylation", Nov. 5, 2014 (Nov. 5, 2014), XP55509166, [retrieved on Sep. 24, 2018]; XP55509163, URL:https://www.ncbi.nlm.nih.gov/pmc/articles/PMC4245933/pdf/gku1021.pdf.

Extended European Search Report dated Nov. 19, 2018, for corresponding European Application No. 16783775.6 (EP3285871).

Carroll, Patrick A., et al. Deregulated Myc Requires MondoA/Mlx for MetabolicReprogramming and Tumorigenesis. Cancer Cell. Feb. 9, 2015; 27(2): 271-285. doi:10.1016/j.ccell.2014.11.024.

Illi, Barbara, et al., Chromatin methylation and cardiovascular aging. Journal of Molecular and Cellular Cardiology vol. 83, Jun. 2015, pp. 21-31.

Oyama, Kyohei, et al., Epigenetic regulation of cardiac myocyte differentiation. Frontiers in Genetics. Nov. 2014, vol. 5, Article 375. doi: 10.3389/fgene.2014.00375.

(56) References Cited

OTHER PUBLICATIONS

Tingare, Asmita, et al., Epigenetics in the heart: the role of histone modifications in cardiac remodelling. Biochem. Soc. Trans. (2013) 41, 789-796; doi:10.1042/BST20130012.
International Search Report for PCT/US2016/028459 (WO2016172224) Published Oct. 27, 2016.

* cited by examiner

SEQUENCE LISTING

```
<160> NUMBER OF SEQ ID NOS: 54

<210> SEQ ID NO 1
<211> LENGTH: 523
<212> TYPE: PRT
<213> ORGANISM: Homo sapiens

<400> SEQUENCE: 1

Met Glu Thr Met Lys Ser Lys Ala Asn Cys Ala Gln Asn Pro Asn Cys
1               5                   10                  15

Asn Ile Met Ile Phe His Pro Thr Lys Glu Glu Phe Asn Asp Phe Asp
                20                  25                  30

Lys Tyr Ile Ala Tyr Met Glu Ser Gln Gly Ala His Arg Ala Gly Leu
            35                  40                  45

Ala Lys Ile Ile Pro Pro Lys Glu Trp Lys Ala Arg Glu Thr Tyr Asp
        50                  55                  60

Asn Ile Ser Glu Ile Leu Ile Ala Thr Pro Leu Gln Gln Val Ala Ser
65                  70                  75                  80

Gly Arg Ala Gly Val Phe Thr Gln Tyr His Lys Lys Lys Ala Met
                85                  90                  95

Thr Val Gly Glu Tyr Arg His Leu Ala Asn Ser Lys Lys Tyr Gln Thr
            100                 105                 110

Pro Pro His Gln Asn Phe Glu Asp Leu Glu Arg Lys Tyr Trp Lys Asn
        115                 120                 125

Arg Ile Tyr Asn Ser Pro Ile Tyr Gly Ala Asp Ile Ser Gly Ser Leu
    130                 135                 140

Phe Asp Glu Asn Thr Lys Gln Trp Asn Leu Gly His Leu Gly Thr Ile
145                 150                 155                 160

Gln Asp Leu Leu Glu Lys Glu Cys Gly Val Val Ile Glu Gly Val Asn
                165                 170                 175

Thr Pro Tyr Leu Tyr Phe Gly Met Trp Lys Thr Thr Phe Ala Trp His
            180                 185                 190

Thr Glu Asp Met Asp Leu Tyr Ser Ile Asn Tyr Leu His Leu Gly Glu
        195                 200                 205

Pro Lys Thr Trp Tyr Val Val Pro Pro Glu His Gly Gln Arg Leu Glu
    210                 215                 220

Arg Leu Ala Arg Glu Leu Phe Pro Gly Ser Ser Arg Gly Cys Gly Ala
225                 230                 235                 240

Phe Leu Arg His Lys Val Ala Leu Ile Ser Pro Thr Val Leu Lys Glu
```

245                 250                 255
Asn Gly Ile Pro Phe Asn Arg Ile Thr Gln Glu Ala Gly Glu Phe Met
                    260                 265                 270

Val Thr Phe Pro Tyr Gly Tyr His Ala Gly Phe Asn His Gly Phe Asn
                275                 280                 285

Cys Ala Glu Ala Ile Asn Phe Ala Thr Pro Arg Trp Ile Asp Tyr Gly
            290                 295                 300

Lys Met Ala Ser Gln Cys Ser Cys Gly Glu Ala Arg Val Thr Phe Ser
305                 310                 315                 320

Met Asp Ala Phe Val Arg Ile Leu Gln Pro Glu Arg Tyr Asp Leu Trp
                325                 330                 335

Lys Arg Gly Gln Asp Arg Ala Val Val Asp His Met Glu Pro Arg Val
                340                 345                 350

Pro Ala Ser Gln Glu Leu Ser Thr Gln Lys Val Gln Leu Pro Arg
            355                 360                 365

Arg Ala Ala Leu Gly Leu Arg Gln Leu Pro Ser His Trp Ala Arg His
        370                 375                 380

Ser Pro Trp Pro Met Ala Ala Arg Ser Gly Thr Arg Cys His Thr Leu
385                 390                 395                 400

Val Cys Ser Ser Leu Pro Arg Gln Ser Ala Val Ser Gly Thr Ala Thr
                405                 410                 415

Gln Pro Arg Ala Ala Val His Ser Ser Lys Lys Pro Ser Ser Thr
            420                 425                 430

Pro Ser Ser Thr Pro Gly Pro Ser Ala Gln Ile Ile His Pro Ser Asn
        435                 440                 445

Gly Arg Arg Gly Arg Gly Arg Pro Pro Gln Lys Leu Arg Ala Gln Glu
    450                 455                 460

Leu Thr Leu Gln Thr Pro Ala Lys Arg Pro Leu Ala Gly Thr Thr
465                 470                 475                 480

Cys Thr Ala Ser Gly Pro Glu Pro Glu Pro Leu Pro Glu Asp Gly Ala
                485                 490                 495

Leu Met Asp Lys Pro Val Pro Leu Ser Pro Gly Leu Gln His Pro Val
            500                 505                 510

Lys Ala Ser Gly Cys Ser Trp Ala Pro Val Pro
        515                 520

<210> SEQ ID NO 2
<211> LENGTH: 31
<212> TYPE: PRT
<213> ORGANISM: Artificial Sequence
<220> FEATURE:
<223> OTHER INFORMATION: FLAG and MYC tags
<220> FEATURE:
<221> NAME/KEY: myc
<222> LOCATION: (7)..(16)
<223> OTHER INFORMATION: myc tag
<220> FEATURE:
<221> NAME/KEY: flag
<222> LOCATION: (23)..(30)
<223> OTHER INFORMATION: flag tag

<400> SEQUENCE: 2

Thr Arg Thr Leu Pro Leu Glu Gln Lys Leu Ile Ser Glu Glu Asp Leu
1               5                   10                  15

Ala Ala Asn Asp Ile Leu Asp Tyr Lys Asp Asp Asp Asp Lys Val
            20                  25                  30

<210> SEQ ID NO 3

-continued

<211> LENGTH: 22
<212> TYPE: DNA
<213> ORGANISM: Artificial Sequence
<220> FEATURE:
<223> OTHER INFORMATION: primer

<400> SEQUENCE: 3
ccaatgtgtc cgtcgtggat ct                                    22

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
gttgaagtcg caggagacaa cc                                    22

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
aggattggag cccagagtgg a                                     21

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
tgatagatga aggcaggaag c                                     21

<210> SEQ ID NO 7
<211> LENGTH: 23
<212> TYPE: DNA
<213> ORGANISM: Artificial Sequence
<220> FEATURE:
<223> OTHER INFORMATION: primer

<400> SEQUENCE: 7
gcgactcaaa aagaaggact ttg                                   23

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
ggcttgctca tcctcaatcc                                       20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
agaagcccag cgctccctca                          20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
gggcgttctt ggccttgcct                          20

<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11
gcagcccaga ggaaacccaa cc                       22

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12
agccgcatcg ctgctctcat c                        21

<210> SEQ ID NO 13
<211> LENGTH: 24
<212> TYPE: DNA
<213> ORGANISM: Artificial Sequence
<220> FEATURE:
<223> OTHER INFORMATION: primer

<400> SEQUENCE: 13
tgctgcaaat ggaactgctt ctgg                     24

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
taccatggag ggtgggttgg aaat                     24

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
gcttcgggtc tgagttccaa                          20

<210> SEQ ID NO 16
<211> LENGTH: 19
<212> TYPE: DNA

```
<213> ORGANISM: Artificial Sequence
<220> FEATURE:
<223> OTHER INFORMATION: primer

<400> SEQUENCE: 16
ggatgaagag cagggtcc                                                19

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
gggacctgaa gccagagaac                                              20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
ccacagaaga gaggcttccg                                              20

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
gcctcacaaa gcacatgact g                                            21

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
tcgacaactt ccgttagcct                                              20

<210> SEQ ID NO 21
<211> LENGTH: 23
<212> TYPE: DNA
<213> ORGANISM: Artificial Sequence
<220> FEATURE:
<223> OTHER INFORMATION: primer

<400> SEQUENCE: 21
ggcgagttct tcacagagac ttg                                          23

<210> SEQ ID NO 22
<211> LENGTH: 24
<212> TYPE: DNA
<213> ORGANISM: Artificial Sequence
<220> FEATURE:
<223> OTHER INFORMATION: primer

<400> SEQUENCE: 22
ccctatactc cagatgtcaa ccgg                                         24
```

<210> SEQ ID NO 23
<211> LENGTH: 21
<212> TYPE: DNA
<213> ORGANISM: Artificial Sequence
<220> FEATURE:
<223> OTHER INFORMATION: primer

<400> SEQUENCE: 23
gcacctgaaa catcccaaca t                                              21

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
ggtccgactc ttctgcagtt                                                20

<210> SEQ ID NO 25
<211> LENGTH: 19
<212> TYPE: DNA
<213> ORGANISM: Artificial Sequence
<220> FEATURE:
<223> OTHER INFORMATION: primer

<400> SEQUENCE: 25
gtattcccaa gcacatcaa                                                 19

<210> SEQ ID NO 26
<211> LENGTH: 19
<212> TYPE: DNA
<213> ORGANISM: Artificial Sequence
<220> FEATURE:
<223> OTHER INFORMATION: primer

<400> SEQUENCE: 26
gtagccagaa gtgaagaac                                                 19

<210> SEQ ID NO 27
<211> LENGTH: 21
<212> TYPE: DNA
<213> ORGANISM: Artificial Sequence
<220> FEATURE:
<223> OTHER INFORMATION: primer

<400> SEQUENCE: 27
tgccaagaag tccaagaatc a                                              21

<210> SEQ ID NO 28
<211> LENGTH: 18
<212> TYPE: DNA
<213> ORGANISM: Artificial Sequence
<220> FEATURE:
<223> OTHER INFORMATION: primer

<400> SEQUENCE: 28
ctgctgctca ctctcctg                                                  18

<210> SEQ ID NO 29
<211> LENGTH: 18
<212> TYPE: DNA
<213> ORGANISM: Artificial Sequence
<220> FEATURE:

<223> OTHER INFORMATION: primer

<400> SEQUENCE: 29
tgtccttggc agcactca                                                  18

<210> SEQ ID NO 30
<211> LENGTH: 22
<212> TYPE: DNA
<213> ORGANISM: Artificial Sequence
<220> FEATURE:
<223> OTHER INFORMATION: primer

<400> SEQUENCE: 30
ttcaccactg tccttgttct ca                                             22

<210> SEQ ID NO 31
<211> LENGTH: 24
<212> TYPE: DNA
<213> ORGANISM: Artificial Sequence
<220> FEATURE:
<223> OTHER INFORMATION: primer

<400> SEQUENCE: 31
cctgataacc ttgaacctgc ttgt                                           24

<210> SEQ ID NO 32
<211> LENGTH: 19
<212> TYPE: DNA
<213> ORGANISM: Artificial Sequence
<220> FEATURE:
<223> OTHER INFORMATION: primer

<400> SEQUENCE: 32
gctgaggctg cttgtgtct                                                 19

<210> SEQ ID NO 33
<211> LENGTH: 21
<212> TYPE: DNA
<213> ORGANISM: Artificial Sequence
<220> FEATURE:
<223> OTHER INFORMATION: primer

<400> SEQUENCE: 33
caccgaactt atgatggaca g                                              21

<210> SEQ ID NO 34
<211> LENGTH: 18
<212> TYPE: DNA
<213> ORGANISM: Artificial Sequence
<220> FEATURE:
<223> OTHER INFORMATION: primer

<400> SEQUENCE: 34
atggcttctg ctctcact                                                  18

<210> SEQ ID NO 35
<211> LENGTH: 21
<212> TYPE: DNA
<213> ORGANISM: Artificial Sequence
<220> FEATURE:
<223> OTHER INFORMATION: primer

<400> SEQUENCE: 35
gcagaggagg agattggaac a                                              21

```
<210> SEQ ID NO 36
<211> LENGTH: 18
<212> TYPE: DNA
<213> ORGANISM: Artificial Sequence
<220> FEATURE:
<223> OTHER INFORMATION: primer

<400> SEQUENCE: 36
gctacaggcg tggtgact                                                    18

<210> SEQ ID NO 37
<211> LENGTH: 21
<212> TYPE: DNA
<213> ORGANISM: Artificial Sequence
<220> FEATURE:
<223> OTHER INFORMATION: primer

<400> SEQUENCE: 37
gcagaccagc ctgacagatt t                                                21

<210> SEQ ID NO 38
<211> LENGTH: 20
<212> TYPE: DNA
<213> ORGANISM: Artificial Sequence
<220> FEATURE:
<223> OTHER INFORMATION: primer

<400> SEQUENCE: 38
ctgacccaca gcagaagagg                                                  20

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
cagtgggaac cttctgggac                                                  20

<210> SEQ ID NO 40
<211> LENGTH: 20
<212> TYPE: DNA
<213> ORGANISM: Artificial Sequence
<220> FEATURE:
<223> OTHER INFORMATION: primer

<400> SEQUENCE: 40
cgcggatctt gagggtgaaa                                                  20

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
ctgctagggc tttaggctcc                                                  20

<210> SEQ ID NO 42
<211> LENGTH: 20
<212> TYPE: DNA
<213> ORGANISM: Artificial Sequence
<220> FEATURE:
<223> OTHER INFORMATION: primer
```

```
<400> SEQUENCE: 42
tttgggagga acgaccttgg                                              20

<210> SEQ ID NO 43
<211> LENGTH: 20
<212> TYPE: DNA
<213> ORGANISM: Artificial Sequence
<220> FEATURE:
<223> OTHER INFORMATION: primer

<400> SEQUENCE: 43
cagagagcat cacgagcaga                                              20

<210> SEQ ID NO 44
<211> LENGTH: 20
<212> TYPE: DNA
<213> ORGANISM: Artificial Sequence
<220> FEATURE:
<223> OTHER INFORMATION: primer

<400> SEQUENCE: 44
ctcttgggca gctcctcttc                                              20

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
gcgggttcat gcaagttgtt                                              20

<210> SEQ ID NO 46
<211> LENGTH: 20
<212> TYPE: DNA
<213> ORGANISM: Artificial Sequence
<220> FEATURE:
<223> OTHER INFORMATION: primer

<400> SEQUENCE: 46
gtttcagagc acctcccctc                                              20

<210> SEQ ID NO 47
<211> LENGTH: 20
<212> TYPE: DNA
<213> ORGANISM: Artificial Sequence
<220> FEATURE:
<223> OTHER INFORMATION: primer

<400> SEQUENCE: 47
tctgagtctg ccttcttctg                                              20

<210> SEQ ID NO 48
<211> LENGTH: 22
<212> TYPE: DNA
<213> ORGANISM: Artificial Sequence
<220> FEATURE:
<223> OTHER INFORMATION: primer

<400> SEQUENCE: 48
gccagggttc acaagtcctg ag                                           22

<210> SEQ ID NO 49
<211> LENGTH: 20
```

```
<212> TYPE: DNA
<213> ORGANISM: Artificial Sequence
<220> FEATURE:
<223> OTHER INFORMATION: primer

<400> SEQUENCE: 49
ttgatggaca agcctgtacc                                               20

<210> SEQ ID NO 50
<211> LENGTH: 20
<212> TYPE: DNA
<213> ORGANISM: Artificial Sequence
<220> FEATURE:
<223> OTHER INFORMATION: primer

<400> SEQUENCE: 50
tcatttgctg ccagatcctc                                               20

<210> SEQ ID NO 51
<211> LENGTH: 20
<212> TYPE: DNA
<213> ORGANISM: Artificial Sequence
<220> FEATURE:
<223> OTHER INFORMATION: primer

<400> SEQUENCE: 51
cctcaacgac cactttgtca                                               20

<210> SEQ ID NO 52
<211> LENGTH: 20
<212> TYPE: DNA
<213> ORGANISM: Artificial Sequence
<220> FEATURE:
<223> OTHER INFORMATION: primer

<400> SEQUENCE: 52
ttactccttg gaggccatgt                                               20

<210> SEQ ID NO 53
<211> LENGTH: 20
<212> TYPE: DNA
<213> ORGANISM: Artificial Sequence
<220> FEATURE:
<223> OTHER INFORMATION: primer

<400> SEQUENCE: 53
aagcccagct caactccatc                                               20

<210> SEQ ID NO 54
<211> LENGTH: 20
<212> TYPE: DNA
<213> ORGANISM: Artificial Sequence
<220> FEATURE:
<223> OTHER INFORMATION: primer

<400> SEQUENCE: 54
tgtccatcaa agccccatcc                                               20
```

VECTORS AND METHODS FOR REGENERATIVE THERAPY

This application claims benefit of U.S. provisional patent application No. 62/150,159, filed Apr. 20, 2015, the entire contents of which are incorporated by reference into this application.

STATEMENT REGARDING FEDERALLY SPONSORED RESEARCH

This invention was made with government support under Grant No. RO1 HL070748, awarded by the National Institutes of Health. The government has certain rights in the invention.

REFERENCE TO A SEQUENCE LISTING SUBMITTED VIA EFS-WEB

The content of the ASCII text the of the sequence listing named "UW57WOU1_ST25", which is 15 kb in size was created on Apr. 19, 2016, and electronically submitted via EFS-Web with this application is incorporated herein by reference in its entirety.

TECHNICAL FIELD OF THE INVENTION

The present invention relates to nucleic acid molecules, vectors, cells, and related compositions and their use for inducing proliferation of quiescent cells and in methods of regenerative therapy.

BACKGROUND OF THE INVENTION

The vast majority of mammalian cardiac myocytes (CM) stop proliferating soon after birth and subsequent heart growth predominately comes from hypertrophy, an increase in cell size, instead of hyperplasia, an increase in cell number. Because CM proliferation is required for the heart regeneration seen in lower vertebrates and neonatal mammalian injury models, there is great interest in understanding the mechanisms regulating CM cell cycle exit and whether this cell cycle withdrawal can be reversed.

Ischemic heart disease leading to heart failure[1, 2] is the leading cause of death in the world[3]. Although adult human hearts are unable to replace lost CMs after injury, substantial cardiac regeneration is seen in lower vertebrate and mammalian models. Adult zebrafish[4] and neonatal mice[5] are able to regenerate their hearts after ±5% has been amputated. Models of myocardial infarction (MI) in newborn mice offer a more clinically relevant injury model to demonstrate heart regeneration capacity in mammals[6, 7]. A common finding in these studies was the mechanism by which cardiac regeneration occurred. Blood clot formation, inflammation, and collagen deposition were seen in response to the injuries, but ultimately new CMs repopulated the lost tissue. Fate mapping studies revealed that the new cardiac myocytes came from dedifferentiation and proliferation of pre-existing cardiac myocytes, in contrast to cardiac progenitor or stem cells[4-6]. However, when cardiac injury was induced in mice at a later time-point, postnatal day 7 (P7), the regenerative response was lost leading to fibrotic scarring[5,6] similar to what is seen with human MIs[1, 2]. Thus, mammalian hearts lose their regenerative capacity early in life, a process that requires CM proliferation.

The poor regenerative response seen in adult hearts highlights the question of whether there is any turnover of CMs in adults. Though there has been controversy over the extent of ACM proliferation, elegant studies have estimated a 0.8% annual renewal rate in mammals[8, 9]. But this very limited source of new ACMs was demonstrated to come from pre-existing ACMs[8]. The rate of ACM hyperplasia increased slightly after MI, though most DNA-synthesis activity resulted in polyploidization and multi-nucleation, rather than complete cell division[8]. Consistent with very rare ACM cell division, gene expression analysis reveals a dramatic downregulation of cell cycle progression genes in ACMs compared with embryonic CMs[10]. Pressure-overload trans-aortic-constriction (TAC) models stimulate ACM expression of G1/S-phase promoting genes, but genes that promote mitosis and cytokinesis remain silenced[10]. As G1/S-phase genes are required for CM hypertrophy[11, 12], the gene expression results are consistent with the hypertrophy-restricted growth and increased DNA-content displayed in ACMs after TAC or MI[8, 13]. Thus, ACMs have cell growth that is uncoupled from cell division[14]. Interestingly, CM switching to hypertrophic growth coincides with the postnatal loss of regeneration capacity[5, 6, 13].

The stable silencing of G2/M and cytokinesis genes represents part of the change in gene expression profile that occurs when CMs undergo terminal differentiation[13]. Recent studies suggest epigenetic mechanisms, such as post-translational modifications of histone proteins, DNA methylation, and non-coding RNAs, direct the changes in gene expression that occur during cardiac development and disease[6, 15-19]. Modulating epigenetic mechanisms can delay CM loss of proliferative and regenerative potential until adolescence, but regeneration in adult hearts remains elusive[20]. Simplistically, there are two types of epigenetically-defined chromatin structure and function: accessible and actively transcribed euchromatin, and, in contrast, condensed and transcriptionally silenced heterochromatin[21, 22]. Each chromatin type is associated with distinct sets of histone modifications and chromatin-associated proteins[22-24]. Histone modifications are thought to establish different states of chromatin by physically altering its structure[25-27], as well as recruiting other effector proteins which possess modification-specific-binding domains[21, 22]. In general, euchromatin is enriched with histone acetylations, H3K4me3, and H3K36me3, which recruit transcriptional machinery[22]. In contrast, heterochromatin is enriched with H3K9me3, H3K27me3, and H4K23me3: repressive methylations that recruit heterochromatin-protein-1 (HP1) family members, Polycomb proteins, and other repressive effectors[21, 22]. Interestingly, cells that have permanently exited the cell cycle show a striking difference in the organization of chromatin within the nucleus. In proliferating fetal CMs, there is limited heterochromatin that is organized into many small foci within the nucleus, while in ACM, these foci accumulate into few, large foci with additional heterochromatin at the nuclear lamina[10]. Similar patterns are observed in other non-proliferative cells; accumulation of heterochromatin coincides with terminal differentiation and cell cycle-exiting[28-30].

E2F and Retinoblastoma family members (Rb, p107, p130) are at the interface of cell cycle gene and chromatin structural regulation[31-34]. In proliferating cells, E2F family proteins bind to a consensus sequence found in the promoters of many cell cycle progression genes, acting as master regulators of cell division[34, 35]. When hypophosphorylated Rb family members bind to E2Fs, they inhibit cell cycle gene expression and cell proliferation. However, mitogenic stimulation can lead to phosphorylation of Rb proteins, freeing E2Fs to activate calf cycle gene expression[34]. In contrast to quiescent cells, terminally differentiated skeletal and cardiac myocytes do not proliferate in response to mitogenic stimuli[36, 37]. This permanent cell cycle exit is mediated by Rb-dependent recruitment of H3K9me3- and H3K27me3-associated proteins to E2F-dependent gene promoters[10, 32, 38, 39]. H3K9me3 and H3K27me3 are highly enriched on cell cycle gene promoters in ACMs compared to embryonic CMs, with H3K9me3 showing preferential enrichment on G2/M and cytokinesis gene promoters[10]. ACM-specific Rb knock out (KO), combined with germline deletion of p130, abrogated the heterochromatin formation of cell cycle genes in ACMs[10]. ACMs in these mice upregulated cell cycle genes, including G2/M and cytokinesis genes, which resulted in ACM proliferation. The Rb/p130 KO mice develop heart failure, though it is unclear if it is a result of ACM proliferation, or due to more broad changes in gene expression profile and loss of global heterochromatin-organization[10]. Rb-family proteins interact with many chromatin-modifiers and transcription factors that also govern gene expression outside of cell-cycle[33, 34], making it difficult to attribute changes in the Rb/p130 KO hearts to a single factor or pathway. Specific perturbation of H3K9me3 in vitro by knockdown of H3K9me3 methyltransferase Suv39h1 resulted in global reduction of H3K9me3, accompanied with specific re-induction of G2/M and cytokinesis genes in ACMs, but this was not seen in vivo[10]. Knockdown of HP1γ also specifically re-induced late cell cycle genes in ACMs, demonstrating that H3K9me3 and its downstream effector are required for the silencing of these genes in vitro[10], but its physiological role in vivo remains uncertain.

There remains a need to understand the mechanisms regulating CM cell cycle exit and provide means by which this cell cycle withdrawal can be reversed. There further remains a need for methods of treating ischemic heart disease to reduce the incidence of heart failure and related deaths.

SUMMARY OF THE INVENTION

The invention provides an expression vector capable of disrupting the silencing of cell cycle genes in adult cells, such as adult cardiac myocytes and other quiescent cells in terminally differentiated tissues. Other examples of quiescent cells and terminally differentiated tissues in which vectors and methods of the invention can be used to induce proliferation include, but are not limited to, skeletal muscle, neurons, pancreatic islet cells, and hepatocytes. These vectors and methods provide tools for regenerative therapy and tissue repair.

In one embodiment, the expression vector comprises: (a) a nucleic acid sequence encoding lysine-specific demethylase 4D (KDM4D); (b) a promoter that induces or effects overexpression of KDM4D, wherein the promoter is operably linked to the nucleic add sequence: and (c) a regulatory element that inducibly represses the overexpression of KDM4D. Optionally, the vector further comprises (d) a tissue-specific promoter operably linked to the nucleic add sequence. Alternatively, tissue-specific overexpression of KDM4D can be achieved through selection of a tissue-specific promoter in (b). The KDM4D is capable of specifically removing the histone modification H3K9me3 by demethylating the lysine residue at position 9 (H3K9) of heterochromatin protein 1 (HP1).

In one embodiment, the promoter of (b) is a tissue-specific promoter. In another embodiment, separate promoters serve the functions described in (b) and (d) above. Representative examples of tissue-specific promoters include, but are not limited to, promoters specific to cardiac tissue, skeletal muscle, neurons, pancreatic islet cells, or hepatocytes. A promoter that is tissue-specific promotes expression of the gene encoded by the nucleic add sequence predominantly in the particular tissue. In one embodiment, the tissue-specific promoter is specific to cardiac tissue. An α-myosin heavy chain (αMHC) promoter is one example of a cardiac-specific promoter. In another embodiment, the tissue-specific promoter is specific to liver tissue, or hepatocytes. A CBA promoter is one example of a liver-specific promoter. Other examples of tissue-specific promoters known in the art include the neuron-specific enolase (NSE) and tubulin α1 promoters for neurons, α1-antitrypsin and albumin (ALB) promoters for hepatocytes, and troponin, CMV, or myosin light chain-2 (MLC2) for cardiac myocytes.

Representative examples of a regulatory element capable of inducibly repressing expression (or overexpression) include, but are not limited to, tetracycline responsive elements. Those skilled in the art will appreciate alternative methods of controlled gene expression that can be adapted for use in a similar manner to regulate the expression of KDM4D, both temporally and histologically. For example, in one embodiment, the regulatory element enables positive regulation of KDM4D expression, while in another embodiment, the regulatory element enables negative regulation of KDM4D expression. In another example, the regulatory element enables tissue-specific and/or condition-specific regulation of KDM4D expression.

Vectors for use in the methods described herein include viral vectors, as well as non-viral vectors, virus-like particles, bacterial vectors, bacteriophage vectors, and other vectors known in the art. In one embodiment, the vector is a viral vector. In a particular embodiment, the viral vector is an adeno-associated virus (AAV) vector, or other vector suited for infecting quiescent cells. Representative examples of an AAV vector include, but are not limited to, AAV6 and AAV9.

The invention also provides a method for inducing proliferation in a mammalian cell by reducing H3K9me3 levels in the cell via KDM4D. In one embodiment, the invention provides a method for inducing tissue-specific hyperplasia in a mammal comprising administering an expression vector as described herein to the mammal. Also provided is a method for inducing cardiac myocyte (CM) hyperplasia in a mammal comprising administering an expression vector of the invention to the mammal. The invention further provides a method for inducing cardiac myocyte (CM) hyperplasia in a mammal. The method comprises grafting CMs to the heart of the mammal, wherein the CMs contain an expression vector of the invention.

The invention additionally provides a method for inducing CM hyperplasia comprising administering KDM4D to CMs. The KDM4D can be administered using a modification of the peptide and/or a delivery means that protects the activity of KDM4D. Administration can be oral, intravenous, subcutaneous, or transdermal.

In one embodiment, the invention provides a method of improving organ function in a mammal comprising grafting cells genetically modified with an expression vector of the invention to the organ. The organ can be, for example, heart, muscle, brain, pancreas, or liver. In one embodiment, the invention provides a method of improving cardiac function in a mammal comprising grafting CMs to the heart of the mammal, wherein the CMs contain an expression vector of the invention. In another embodiment, the invention provides a method of improving cardiac function in a mammal comprising administering an expression vector of the invention to the mammal. Also provided is a method of improving cardiac function in a mammal comprising administering KDM4D to the mammal.

The invention further provides a method of proliferating CM comprising culturing CM with KDM4D under conditions effective to induce CM hyperplasia. In one embodiment, the CM are adult CM (ACM). In addition, the invention provides a method of promoting cardiac regeneration comprising reducing lysine 9 of histone H3 (H3K9me3) levels in CMs. In one embodiment, the reducing comprises administering an expression vector of the invention to a subject in need of cardiac regeneration. In a particular embodiment, the expression vector is administered by administering CMs that contain the expression vector. In another embodiment, the reducing comprises administering KDM4D.

The methods of the invention can involve administration to the subject by any of a variety of means understood by those skilled in the art to be suitable for particular circumstances. In some embodiments, the administration is systemic. In other embodiments, the administration is intravenous. In some embodiments, the administration is by intramyocardial injection. The subject is typically a mammal. In one embodiment, the mammal is human. In other embodiments, the mammal is a veterinary subject. Examples of veterinary subjects include, but are not limited to, equine, canine, bovine, porcine, ovine, and feline subjects.

DETAILED DESCRIPTION OF THE INVENTION

Figures 1A, 1B, 1C, 1D, 1E, 1F:
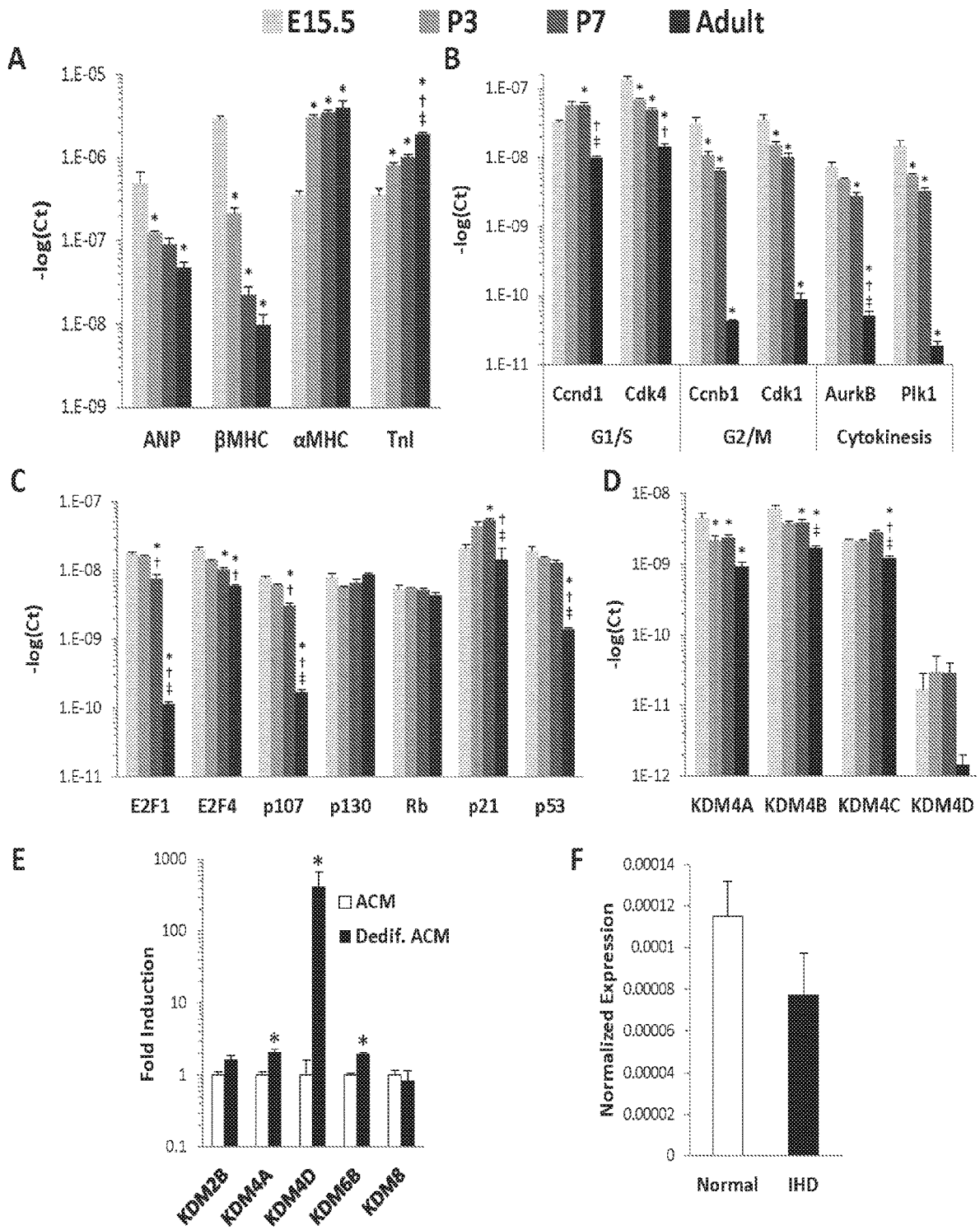
FIGS. 1A-1F. Characterization of histone demethylases in development and disease. (1A-1D) E15.5, P3, P7, and 10 week (adult) CM expression levels of (1A) cardiac myocyte genes, (1B) cell cycle progression genes, (1C) cell cycle regulators, and (1D) KDM4 H3K9me3-demethylase family members through development. (1E) Gene expression of HDMs in dedifferentiated mouse ACMs. (1F) KDM4D expression in human ischemic cardiomyopathy sample (IHD), expression normalized to GAPDH. Sample Number: (A-D) P0=3, P3=2, P7=4, 10 week=3. (1E) ACM=3, Dedif. ACM=3. (1F) Normal=2, IHD=3. Statistics: (1A-1D) One-way ANOVA/Tukey's test, *$P<0.05$ vs E15.5, †$P<0.05$ vs P3, ‡$P<0.05$ vs P7. (1E-1F) Two-tailed T-test, *$P<0.05$.

The invention is based on the unexpected finding that terminally differentiated cells can be induced to proliferate via epigenetic manipulation. The invention thus provides materials and methods for reversibly inducing proliferation in quiescent cells based on discovery of the role of H3K9me3 demethylases in regulating ACM cell cycle gene silencing.

Before the discovery of histone demethylases (HDMs)[40], H3K9me3, and histone methylation in general, was thought to be a permanent mark[41]. However, the dynamic nature of histone methylation is beginning to be appreciated[42-44], though little is known about the functions of HDMs in the heart. Interestingly, members of the KDM4 family of H3K9me3 demethylases are upregulated in several forms of cancer and are thought to promote cell proliferation and survival[45-48]. A member of the KDM4 family, KDM4A, has been studied in the heart[17, 49]. CM-specific overexpression of KDM4A in mice exacerbated TAC-induced hypertrophy and fetal CM gene expression, while CM-specific KDM4A deletion diminished the effects of pressure-overload, though neither manipulation had an effect at baselines[49]. Mechanistic studies demonstrated KDM4A knockdown in neonatal CMs increases H3K9me3 levels at the ANP promoter and modestly downregulates ANP expression[17]. H3K9me3 and HP1 enrichment on the ANP promoter was reduced in an isolated-working heart model of elevated preload that induces ANP expression[17]. However, KDM4A expression and enrichment on the ANP gene promoter were not changed in this model[17]. Thus, it is not clear how KDM4A regulates fetal CM gene expression in ACMs. Complicating the interpretation of these results further is the fact that KDM4A has dual-substrate specificity; KDM4A can demethylate repressive H3K9me3, but also activating H3K36me3[50-52]. We also found that global levels of both these modifications were reduced in ACMs with adenovirus-mediated KDM4A overexpression. One KDM4 family member, KDM4D, has robust and specific H3K9-demethylase activity[50, 52], giving it particular usefulness as an experimental tool to study H3K9me3 specifically. Until this study, KDM4D has not been explored.

Definitions

All scientific and technical terms used in this application have meanings commonly used in the art unless otherwise specified. As used in this application, the following words or phrases have the meanings specified.

As used herein, "lysine-specific demethylase 4D" or "KDM4D" means a specific member of the KDM4 family of lysine-specific demethylases that exhibits demethylase activity specific to the methylated lysine residue at position 9 (H3K9) of heterochromatin protein 1 (HP1). In one embodiment, the KDM4D has the amino acid sequence shown in SEQ ID NO: 1. The amino acid sequence optionally further includes tags, such as, for example, a MYC tag and/or a FLAG tag, as shown in SEQ ID NO: 2.

As used herein, "inducibly represses" or "inducible repression" refers to regulation of gene expression whereby expression of the gene can be repressed upon introduction of an inducing condition. The inducing condition can be administration of or contact with an agent that effects the repression. The agent can be a corepressor, such as is found in repressible gene regulation wherein expression is on except when the corepressor is present to suppress gene expression. Alternatively, the agent can be an inducer, such as is found in inducible gene regulation wherein expression is off except when the inducer is present to allow for gene expression.

As used herein, a "regulatory element" refers to an element that regulates gene expression. The regulatory element may induce or repress gene expression in response to the presence or absence of a condition.

As used herein, a "tetracycline responsive element" refers to a regulatory element that reduces expression from a tet-inducible promoter in the presence of tetracycline or a derivative thereof, e.g., doxycycline. One example of a tetracycline responsive element is a tetracycline-controlled transactivator (tTA), created by fusion of the tetracycline repressor (tetR) with a transcriptional activation domain, such as the C-terminal domain of VP16 of herpes simplex virus (HSV).

The term "nucleic acid" or "polynucleotide" or "oligonucleotide" refers to a sequence of nucleotides, a deoxyribonucleotide or ribonucleotide polymer in either single- or double-stranded form, and unless otherwise limited, encompasses known analogs of natural nucleotides that hybridize to nucleic acids in a manner similar to naturally occurring nucleotides.

The term "primer," as used herein, means an oligonucleotide designed to flank a region of DNA to be amplified. In a primer pair, one primer is complementary to nucleotides present on the sense strand at one end of a polynucleotide fragment to be amplified and another primer is complementary to nucleotides present on the antisense strand at the other end of the polynucleotide fragment to be amplified. A primer can have at least about 11 nucleotides, and preferably, at least about 16 nucleotides and no more than about 35 nucleotides. Typically, a primer has at least about 80% sequence identity, preferably at least about 90% sequence identity with a target polynucleotide to which the primer hybridizes.

As used herein, the term "probe" refers to an oligonucleotide, naturally or synthetically produced, via recombinant methods or by PCR amplification, that hybridizes to at least part of another oligonucleotide of interest. A probe can be single-stranded or double-stranded.

As used herein, the term "active fragment" refers to a substantial portion of an oligonucleotide that is capable of performing the same function of specifically hybridizing to a target polynucleotide.

As used herein, "hybridizes," "hybridizing," and "hybridization" means that the oligonucleotide forms a noncovalent interaction with the target DNA molecule under standard conditions. Standard hybridizing conditions are those conditions that allow an oligonucleotide probe or primer to hybridize to a target DNA molecule. Such conditions are readily determined for an oligonucleotide probe or primer and the target DNA molecule using techniques well known to those skilled in the art. The nucleotide sequence of a target polynucleotide is generally a sequence complementary to the oligonucleotide primer or probe. The hybridizing oligonucleotide may contain nonhybridizing nucleotides that do not interfere with forming the noncovalent interaction. The nonhybridizing nucleotides of an oligonucleotide primer or probe may be located at an end of the hybridizing oligonucleotide or within the hybridizing oligonucleotide. Thus, an oligonucleotide probe or primer does not have to be complementary to all the nucleotides of the target sequence as long as there is hybridization under standard hybridization conditions.

The term "complement" and "complementary" as used herein, refers to the ability of two DNA molecules to base pair with each other, where an adenine on one DNA molecule will base pair to a guanine on a second DNA molecule and a cytosine on one DNA molecule will base pair to a thymine on a second DNA molecule. Two DNA molecules are complementary to each other when a nucleotide sequence in one DNA molecule can base pair with a nucleotide sequence in a second DNA molecule. For instance, the two DNA molecules 5'-ATGC and 5'-GCAT are complementary, and the complement of the DNA molecule 5'-ATGC is 5'-GCAT. The term complement and complementary also encompasses two DNA molecules where one DNA molecule contains at least one nucleotide that will not base pair to at least one nucleotide present on a second DNA molecule. For instance the third nucleotide of each of the two DNA molecules 5'-ATTGC and 5'-GCTAT will not base pair, but these two DNA molecules are complementary as defined herein. Typically two DNA molecules are complementary if they hybridize under the standard conditions referred to above. Typically, two DNA molecules are complementary if they have at least about 80% sequence identity, preferably at least about 90% sequence identity.

As used herein, "a" or "an" means at least one, unless clearly indicated otherwise.

As used herein, to "prevent" or "protect against" a condition or disease means to hinder, reduce or delay the onset or progression of the condition or disease.

As used herein, the term "isolated" means that a naturally occurring DNA fragment, DNA molecule, coding sequence, or oligonucleotide is removed from its natural environment, or is a synthetic molecule or cloned product. Preferably, the DNA fragment, DNA molecule, coding sequence, or oligonucleotide is purified, i.e., essentially free from any other DNA fragment, DNA molecule, coding sequence, or oligonucleotide and associated cellular products or other impurities.

Vectors

In one embodiment, the expression vector comprises: (a) a nucleic acid sequence encoding lysine-specific demethylase 4D (KDM4D); (b) a promoter that induces or effects overexpression of KDM4D, wherein the promoter is operably linked to the nucleic acid sequence; and (c) a regulatory element that inducibly represses the overexpression of KDM4D. Optionally, the vector further comprises (d) a tissue-specific promoter operably linked to the nucleic acid sequence. In some embodiments, the tissue-specific overexpression of KDM4D is be achieved through selection of a tissue-specific promoter in (b). In some embodiments, tissue-specific expression is provided through both (b) and an additional promoter (d). The KDM4D is capable of specifically removing the histone modification H3K9me3 by demethylating the lysine residue at position 9 of histone 3 (H3K9).

While the promoter of (b) can be a tissue-specific promoter, and in some embodiments, separate promoters serve the functions described in (b) and (d) above, the selection of a tissue-specific promoter is designed to optimize preferential expression in the target tissue while minimizing unintended expression elsewhere. Representative examples of tissue-specific promoters include, but are not limited to, promoters specific to cardiac tissue (myosin heavy chain, troponin I or T), skeletal muscle (myogenein, MyoD, muscle creatine kinase), neurons, pancreatic islet cells, or hepatocytes. A promoter that is tissue-specific promotes expression of the gene encoded by the nucleic acid sequence predominantly in the particular tissue. In one embodiment, the tissue-specific promoter is specific to cardiac tissue. An α-myosin heavy chain (αMHC) promoter is one example of a cardiac-specific promoter. In another embodiment, the tissue-specific promoter is specific to liver tissue, or hepatocytes. A CBA promoter is one example of a liver-specific promoter. Other examples of tissue-specific promoters known in the art include the neuron-specific enolase (NSE) and tubulin α1 promoters for neurons, α1-antitrypsin and albumin (ALB) promoters for hepatocytes, and troponin, CMV, or myosin light chain-2 (MLC2) for cardiac myocytes.

Representative examples of a regulatory element capable of inducibly repressing expression (or overexpression) include, but are not limited to, tetracycline responsive elements and hormone responsive proteins. Those skilled in the art will appreciated alternative methods of controlled gene expression that can be adapted for use in a similar manner to regulate the expression of KDM4D, both temporally and histologically. For example, in one embodiment, the regulatory element enables positive regulation of KDM4D expression, while in another embodiment, the regulatory element enables negative regulation of KDM4D expression. In another example, the regulatory element enables tissue-specific and/or condition-specific regulation of KDM4D expression. While the ability to turn off expression of KDM4D is desirable, it is not essential to all embodiments. In one embodiment, the invention provides a vector comprising a nucleic acid sequence encoding lysine-specific demethylase 4D (KDM4D) and a promoter that induces or effects overexpression of KDM4D, wherein the promoter is operably linked to the nucleic acid sequence.

Vectors for use in the methods described herein include viral vectors, as well as non-viral vectors, virus-like particles, bacterial vectors, bacteriophage vectors, and other vectors known in the art. In one embodiment, the vector is a viral vector. In a particular embodiment, the viral vector is an adeno-associated virus (AAV) vector, or other vector suited for infecting quiescent cells. Representative examples of an AAV vector include, but are not limited to, AAV6 and AAV9.

KDM4D amino acid sequence (SEQ ID NO: 1):

```
MetETMetKSKANCAQNPNCNIMetIFHPTKEEFNDFDKYIAYMet
ESQGAHRAGLAKIIPPKEWKARETYDNISEILIATPLQQVASGRAG
VFTQYHKKKKAMetTVGEYRHLANSKKYQTPPHQNFEDLERKYWK
NRIYNSPIYGADISGSLFDENTKQWNLGHLGTIQDLLEKECGVVIE
GVNTPYLYFGMetWKTTFAWHTEDMetDLYSINYLHLGEPKTWYVV
PPEHGQRLERLARELFPGSSRGCGAFLRHKVALISPTVLKENGIP
FNRITQEAGEFMetVTFPYGYHAGFNHGFNCAEAINFATPRWIDYG
KMetASQCSCGEARVTFSMetDAFVRILQPERYDLWKRGQDRAVVD
HMetEPRVPASQELSTQKEVQLPRRAALGLRQLPSHWARHSPWP
MetAARSGTRCHTLVCSSLPRQSAVSGTATQPRAAAVHSSKKPSS
TPSSTPGPSAQIIHPSNGRRGRGRPPQKLRAQELTLQTPAKRPLL
AGTTCTASGPEPEPLPEDGALMetDKPVPLSPGLQHPVKASGCSW
APVP
```

Optional additional amino acid sequence with myc (underlined) and flag (shaded) tags (SEQ ID NO: 2):

T R T L P L E Q K L I S E E D L A A N D I L D Y K D D D D K V Stop

Compositions & Kits

The invention provides compositions, which can be provided as kits and/or used for the methods described herein. Compositions of the invention comprise vectors, nucleic acid molecules, and cells as described herein. Compositions and kits of the invention can include additional containers, agents, and materials to facilitate practice of the invention.

Methods of the Invention

The invention provides methods for inducing tissue-specific hyperplasia in a mammal comprising administering an expression vector as described herein to the mammal. The method can be tailored to any organ or tissue in which proliferation or regeneration of quiescent cells is of interest. Examples of tissues in which regeneration or proliferation may be of interest include, but art not limited to, heart, muscle, brain, nervous system, pancreas and liver. Also provided is a method for inducing cardiac myocyte (CM) hyperplasia in a mammal comprising administering an expression vector of the invention to the mammal. The invention further provides a method for inducing cardiac myocyte (CM) hyperplasia in a mammal. The method comprises grafting CMs to the heart of the mammal, wherein the CMs contain an expression vector of the invention.

The invention additionally provides a method for inducing CM hyperplasia comprising administering KDM4D to CMs. The KDM4D can be administered using a modification of the peptide and/or a delivery means that protects the activity of KDM4D. Administration can be systemic, localized, oral, intravenous, subcutaneous, or transdermal.

In one embodiment, the invention provides a method of improving organ function in a mammal comprising grafting cells genetically modified with an expression vector of the invention to the organ. The organ can be, for example, heart, muscle, brain, pancreas, or liver. In one embodiment, the invention provides a method of improving cardiac function in a mammal comprising grafting CMs to the heart of the mammal, wherein the CMs contain an expression vector of the invention. In another embodiment, the invention provides a method of improving cardiac function in a mammal comprising administering an expression vector of the invention to the mammal. Also provided is a method of improving cardiac function in a mammal comprising administering KDM4D to the mammal.

The invention further provides a method of proliferating CM comprising culturing CM with KDM4D under conditions effective to induce CM hyperplasia. In one embodiment, the CM are adult CM (ACM). In addition, the invention provides a method of promoting cardiac regeneration comprising reducing lysine 9 of histone H3 (H3K9me3) levels in CMs. In one embodiment, the reducing comprises administering an expression vector of the invention to a subject in need of cardiac regeneration. In a particular embodiment, the expression vector is administered by administering CMs that contain the expression vector. In another embodiment, the reducing comprises administering KDM4D.

The methods of the invention can involve administration to the subject by any of a variety of means understood by those skilled in the art to be suitable for particular circumstances. In some embodiments, the administration is systemic. In other embodiments, the administration is intravenous. In some embodiments, the administration is by intramyocardial injection. The subject is typically a mammal. In one embodiment, the mammal is human. In other embodiments, the mammal is a veterinary subject. Examples of veterinary subjects include, but are not limited to, equine, canine, bovine, porcine, ovine, and feline subjects.

EXAMPLES

The following examples are presented to illustrate the present invention and to assist one of ordinary skill in making and using the same. The examples are not intended in any way to otherwise limit the scope of the invention.

Example 1

Epigenetic Regulation of Cardiac Myocyte Cell Cycle Arrest

This example demonstrates that trimethylation of Lysine 9 of Histone H3 (H3K9me3), a histone modification associated with heterochromatin, is required for the silencing of cell cycle genes in adult CMs (ACMs). To test this, we developed a transgenic (BiTg) mouse model where H3K9me3 is specifically removed by histone demethylase KDM4D in CMs. Loss of H3K9me3 in CMs disrupts ACM cell cycle gene silencing preferentially and results in increased CM cycling. Normalized heart mass was increased by postnatal day 14 (P14) and continued to increase until 9-weeks of age. ACM number, but not size, was significantly increased in BiTg hearts, suggesting CM hyperplasia accounts for the increased heart mass. Challenging H3K9me3-depleted hearts with a hypertrophic growth signal stimulated ACM mitotic activity. Thus, we demonstrated that H3K9me3 is required for cell cycle gene silencing in ACMs and depletion of H3K9me3 allows hyperplastic growth in vivo.

Methods

Mouse Studies. The αMHC-tTA mice used to control transgene expression was generated by the Robbins lab (60). We used the previously published responder construct, which possesses a tetracycline responsive element upstream of an attenuated αMHC promoter to drive KDM4D expression (60). Plasmid containing FLAG- and MYC-tagged human KDM4D cDNA (origene RC212600) had a NotI restriction site present in the cDNA sequence, which we destroyed by inducing a silent mutation (Agilent 200521). The resulting cDNA was subcloned into the responder construct, then freed of vector backbone, purified, and injected into mouse pronuclei (University of Washington transgenic core facility). The resulting tet transgenic was bred to the αMHC-tTA line to generate the CM-specific KDM4D induction model. Littermate controls were used for all experiments involving transgenic mice. TAC and sham operations were performed on 10 to 12 week old littermates from breeders backcrossed ≥8 generations to the C57/B6 strain. Mice were anesthetized using ketamine (130 mg/kg i.p.) and xylazine (8.8 mg/kg i.p.) and subjected to transverse aortic constriction using a 26-gauge needle as described (103).

CM cell isolation and culture. Heparinized mice were euthanized with isoflurane and hearts were extracted and arrested in KB buffer (mmol/L: KCl 20, KH2PO4 10, K+-glutamate 70, MgCl2 1, glucose 25, taurine 20, EGTA 0.5, HEPES 10, 0.1% albumin, pH 7.4 with KOH). For purified ACM preparations, the aorta was cannulated and the heart was washed with Tyrodes solution (pH 7.4, supplemented with 25 uM Blebbistatin −/−) and digested for 7 minutes with collagenase II (Worthington 4176) and Protease Streptomyces griseus XIV (Sigma P5147) using Langendorf perfusion. Ventricles were dissociated and the resulting cell suspension was filtered through a 100 μm mesh. Three rounds of low speed centrifugation, where ACMs are loosely pelleted and non-CMs in suspension are aspirated, density purify the ACM population, resulting in >90% rod-shaped ACMs. For embryonic and postnatal CM preparations, hearts were washed in Ads buffer (mmol/L: NaCl 116, HEPES 20, NAH2PO4 10.8, glucose 5.5, KCl 5.4, MgSO4 0.83) and incubated with enzyme solution (Collagenase II, Pancreatin (Sigma P3292)) with rotation. Freed cells were collected into serum (stopping digestion) every 20 minutes, resulting in dissociation of the entire heart within 2 hours. The resulting cell suspension was fractionated using a percoll (Sigma P4937) gradient, and the CM layer and non-CM layer were each collected. Quality and purity of CM preparations were verified by immunostaining, flow cytometry, and RNA expression of cell-type-specific markers.

Control ACM and dedifferentiated ACM cDNA was generated as described (57). In brief, ACMs were plated on laminin-coated dishes and cultured with growth factors for 10-14 days, resulting in a loss of sarcomere organization and increased CC activity.

RNA isolation and analysis. RNA was isolated from cells and tissue using TRISOL (Sigma T9424) phenol/chloroform purification, followed by column purification with DNase treatment (Qiagen 74004). For human gene expression studies, normal human heart sample was obtained from commercial vendors (Clontech 636532, lot 1206518A: and Agilent 540011, lot 6151000). Ischemic heart disease samples came from consenting male subjects in their 60's that underwent placement of a left ventricular assist device.

cDNA was synthesized as described in the manufacturers guidelines (Roche 04896866001). qPCR was performed using SYBR green (Life Technologies 4472908) on a realtime PCR machine (ABI 7900HT). Primers were validated by standard PCR with electrophoresis to confirm specific target band and lack of primer dimers. qPCR dissociation curves were consistent with a single specific product. Ct values were assigned using ABI's SDS 2.4 software with automated thresholding and baselines. The standard curve method or dCt method was used to quantify expression, and expression of each gene was normalized by GAPDH. However, in FIG. 1A-D, we present -log(Ct) values. Finding a suitable control gene that is stably expressed at different stages in CM development is not trivial (104). Gapdh was the most stably expressed control across all samples compared to S26 and RpIp0, but compared to normalization by input RNA, Gapdh normalization resulted in E15.5 CM gene expression being underestimated by ~2.5 fold, as Gapdh expression decreases in P3 CMs, then remains stable; consistent with the high glycolytic activity in fetal hearts (105). Standard Curves were generated using tissue or cells that highly express the indicated gene, resulting in qPCR efficiencies ranging from 88-97%. The sequences of primers used are:

Mouse (SEQ ID NOs: 3-50, respectively; individual SEQ ID Nos in parentheses below):

```
Gapdh
F-CCAATGTGTCCGTCGTGGATCT (3),

R-GTTGAAGTCGCAGGAGACAACC (4);

ANP
F-AGGATTGGAGCCCAGAGTGGA (5),

R-TGATAGATGAAGGCAGGAAGC (6);

bMHC
F-GCGACTCAAAAAGAAGGACTTTG (7),

R-GGCTTGCTCATCCTCAATCC (8);

AMHC
F-AGAAGCCCAGCGCTCCCTCA (9),

R-GGGCGTTCTTGGCCTTGCCT (10);

cTNIF
F-GCAGCCCAGAGGAAACCCAACC (11),

R-AGCCGCATCGCTGCTCTCATC (12);

Ccnd1
F-TGCTGCAAATGGAACTGCTTCTGG (13),

R-TACCATGGAGGGTGGGTTGGAAAT (14);

Ccne1
F-GCTTCGGGTCTGAGTTCCAA (15),

R-GGATGAAGAGCAGGGGTCC (16);

Cdk4
F-GGGACCTGAAGCCAGAGAAC (17),

R-CCACAGAAGAGAGGCTTCCG (18);

Ccnb1
F-GCCTCACAAAGCACATGACTG (19),

R-TCGACAACTTCCGTTAGCCT (20);

Cdk1
F-GGCGAGTTCTTCACAGAGACTTG (21),

R-CCCTATACTCCAGATGTCAACCGG (22);

AurkB
F-GCACCTGAAACATCCCAACAT (23),

R-GGTCCGACTCTTCTGCAGTT (24);

Pik1
F-GTATTCCCAAGCACATCAA (25),

R-GTAGCCAGAAGTGAAGAAC (26);

E2F1
F-TGCCAAGAAGTCCAAGAATCA (27),

R-CTGCTGCTCACTCTCCTG (28);

E2F4
F-TGTCCTTGGCAGCACTCA (29);

R-TTCACCACTGTCCTTGTTCTCA (30);

Rb
F-CCTGATAACCTTGAACCTGCTTGT (31),

R-GCTGAGGCTGCTTGTGTCT (32);

p130
F-CACCGAACTTATGATGGACAG (33),

R-ATGGCTTCTGCTCTCACT (34);

p107
F- GCAGAGGAGGAGATTGGAACA (35),

R-GCTACAGGCGTGGTGACT (36);

p21
F-GCAGACCAGCCTGACAGATTT (37),

R-CTGACCCACAGCAGAAGAGG (38);

p53
F-CAGTGGGAACCTTCTGGGAC (39),

R-CGCGGATCTTGAGGGTGAAA (40);

KDM4A
F-CTGCTAGGGCTTTAGGCTCC (41),

R-TTTGGGAGGAACGACCTTGG (42);

KDM4B
F-CAGAGAGCATCACGAGCAGA (43),

R-CTCTTGGGCAGCTCCTCTTC (44);

KDM4C
F-GCGGGTTCATGCAAGTTGTT (45),

R-GTTTCAGAGCACCTCCCCTC (46);

KDM4D (endogenous)
F-TCTGAGTCTGCCTTCTTCTG (47),

R-GCCAGGGTTCACAAGTCCTGAG (48);

KDM4D (transgene)
F-TTGATGGACAAGCCTGTACC (49),

R-TCATTTGCTGCCAGATCCTC (50).
```

Mouse: TaqMan (Life Technologies) reagents were used for the following genes: KDM2B (Mm01194587_m1), KDM4A (Mm00605000_m1), KDM6B (Mm01332680_m1), KDM8 (Mm00513079_m1), GAPDH (Mm99999915_g1).

Human (SEQ ID NOs: 51-54, respectively; individual SEQ ID Nos in parentheses below):

```
GAPDH
F-CCTCAACGACCACTTTGTCA (51),

R-TTACTCCTTGGAGGCCATGT (52);

KDM4D
F-AAGCCCAGCTCAACTCCATC (53),

R-TGTCCATCAAAGCCCCATCC (54).
```

RNAseg library construction (Illumina Tru-Seq) and paired-end RNA-sequencing (ABI3730XL) was performed by the Stam Lab's University of Washington core facility. Read alignment was performed using Bowtie/Cufflinks package. Partek Genomic Suites was used for mRNA quantification, differential expression analysis, and gene ontology.

2-D Echocardiography. Under 0.5% isoflurane, mice EKG and heart function was assessed using Visual Sonics Vevo 2100. Parasternal short axis images at the plane of the papillary muscle were collected in B- and M-Modes. Images were collected with heart rates ranging from 400-500 BPMs. Imaging and analysis was performed by a single operator who was blinded to the genotypes. Quantification of images was performed using Vevo Labs 1.7.0, according to the manufacturer's guidelines.

Protein extraction and Western Blotting. Isolated ACMs were pelleted and resuspended in lysis buffer (0.5% NP-40, 25 mM KCl, 5 mM MgCl2, 10 mM Tris-HCl, pH 8.0) and homogenized (Wheaton 358103), releasing soluble cytoplasmic proteins. Nuclear-enriched pellets were processed to release chromatin-associated proteins from DNA; including sonication, MNase treatment, and addition of 1% SDS, 600 mM NaCl, and 20 mM βME. The nuclear proteins were quantified using a BOA assay (Thermo Scientific 23252) and were loaded on polyacrylamide gels for electrophoresis, subsequently transferred onto PVDF membrane, and probed with the indicated antibodies: KDM4D (Abcam ab93694). H3K9me3 (Abcam ab8898), pan H3 (Millipore 05-928), H3K36me3 (Active Motif 61101), H3K9me2 (Millipore 07-441), and H4K20me3 (Abcam ab9053). HRP-conjugated secondary antibodies (Santa Cruz) and ECL-detection (Thermo Scientific 34095) were used.

Histological studies and quantification CM dimensions and CM number. For histological analysis, arrested P14 or 9 week hearts were fixed with 4% PFA. Paraffin sections were stained with H&E, Masson Trichrome, or immunostained using standard protocol with FLAG (Sigma F7425) α-actinin (Sigma A7811), cardiac Troponin T (Thermo Scientific MS-295-P), Ki67 (Abcam ab15580) and phospho-H3 (Abcam ab5176) antibodies, and Hoechst (Life Technologies H3570) to visualize nuclei. Images were acquired with confocal microscopy (Nikon A1R). To assess ACM transverse area, sections were stained with Wheat Germ Agglutinin (WGA, Life Technologies W6748), a marker for plasma membrane. Stitched-images of the whole left ventricle were acquired on a Nikon Ti-E scope. We chose several regions in each section at random, though we excluded large vessels, epicardium and endocardium, and >1000 cells per animal were analyzed using Image J's "analyze particle" function (negative image of WGA stain), resulting in direct measurement of transverse area. For ACM longitudinal area and length measurements, isolated ACMs were fixed with 4% PFA and imaged. The area and long-axis of hundreds of ACMs for each animal were manually traced and quantified using Image J's "measure" function. We calculated CM volume using the formula: (mean ACM length×mean ACM transverse area). CM number was estimated from the following formula: [mean Heart Volume (Heart mass/1.06, the density of muscle tissue(106))/mean ACM volume×0.75 (the proportion of adult murine heart volume occupied by CMs(106))] The number of nuclei per ACM was counted manually for >100 cells per animal.

Imaging of thick sections. For unambiguous determination of cell type in our phospho-H3 staining assays in operated mice, we developed a method for generating, staining, and imaging 100 μm-thick heart sections, which will be described in detail in a methodologies article. Briefly, hearts were arrested in KB buffer, perfused with KB, then perfusion fixed with methanol cooled to −20° C. The hearts were rehydrated in Methanol:PBS gradients (100:0, 80:20, 60:40), then washed with PBS and mounted in 5% low-melt agarose. 100 μm-thick sections were cut from a Leica 1200s vibratome and were stained in suspension, with reagents listed above as well as with Phalloidin (ThermoFisher Scientific A22287). The stained sections were mounted to glass coverslips coated with 0.01% poly-L-lysine. To increase the transparency of the sections, which is needed to view the interior of the thick sections, they were cleared: sections were incubated in an isopropanol series (70%, 85%, 95%, 100%) followed by incubations in a 1:2 solution of benzyl alcohol and benzyl benzoate. The samples were prepared, imaged with confocal microscopy, and analyzed by a single operator blinded to the genotypes. We calculated the number of pH3+ ACMs using the formula: [(pH3+ ACM nuclei/mm3))/(nuclei #/ACM)/(ACM/mm3)] We note that transverse area measurements in the sham-operated hearts were 19.2% less than at baseline, which we attribute to differences in fixation procedure, consistent with other reports comparing cell shrinkage after formaldehyde or alcohol fixation (107). Because of this, transverse area in all groups was corrected by multiplying by a constant factor of 1.192, when calculating ACM number in the post-operation methanol-fixed samples: [mean Heart Volume (Heart mass/1.06, the density of muscle tissue(106))/mean ACM volume (mean ACM baseline length×mean ACM post-operation transverse area)×0.75 (the proportion of adult murine heart volume occupied by CMs (106))].

Figures 5A, 5B, 5C, 5D, 5E:
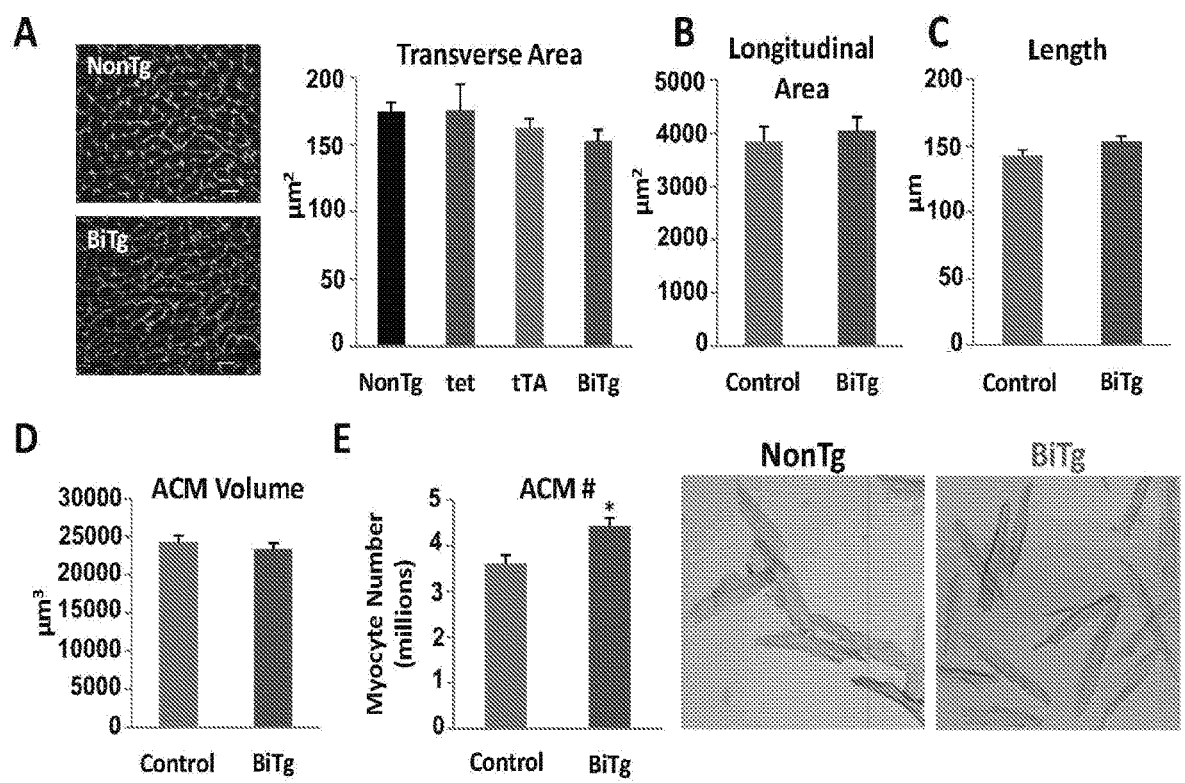
FIGS. 5A-5E. Cardiac myocyte number is increased in BiTg mice. (5A) Left, WGA staining in 9-week NonTg and BiTg PFA-fix hearts, bar=20 μm. Right, quantification of ACM transverse area. (5B) Quantification of longitudinal area and (5C) length measured in dispersed, isolated 9-wk CMs, with representative images below. (5D) Calculated ACM volume and (5E) ACM number at 9-wks of age. Sample Number: (5A-5E) Each assay had ≥3 animals per group. Statistics: (5A) One-way ANOVA/Tukey's test, *$P<0.05$ vs NonTg, †$P<0.05$ vs tet, ‡$P<0.05$ vs tTA. (5B,5C) Two-tailed T-test, control vs. BiTg, *$P<0.05$. (5D-5E) The Bootstrap method was used to compute standard error and Permutation test was used to compute p-value, *$P<0.05$.

Statistics. All results are displayed as mean±standard error of means. Graphpad Prism was used for one-way-ANOVAs and Tukey's post hoc tests performed on studies comparing more than two groups. Graphpad Prism was used for two-way-ANOVAs and Tukey's post hoc tests performed on studies with two independent variables. Microsoft Excel F-test and two-tailed T-test functions were used to analyze studies comparing two groups. For outcomes where different basic measurements were combined for calculations (FIGS. 5D and E, and FIG. 9D) we used the bootstrap method (10,000 bootstrap samples) to compute standard error and the Permutation test (100,000 Monte-Carlo samples) was used to compute p-value; with the assumption that ACM transverse area, ACM length, and heart volume are independent variables. For RNA-seq analysis, Partek Genomic Suites was used to perform statistics.

Study approval. All animal studies were performed in accordance with an approved Institutional Animal Care and Use Committee (IACUC protocol #4290-01), the University of Washington institutional guidelines, and the National Institute of Health Guide for the Care and Use of Laboratory Animals. Human ischemic heart disease samples came from participants that gave written and informed consent; the use of human samples was approved by the University of Washington's Institutional Review Board (IRB #35358).

Adenoviral studies. Adenoviruses for KDM4A and LacZ were generated according to manufacturers guidelines (Agilent 240082), isolated ACMs were plated on laminin coated wells in M199 medium supplemented with 1× ITS, 1× PS, 5 mM Taurine, 1 mM Na-pyruvate, 5 mM Creatine, 2 mM L-carnitine, and 25 mM Blebistatin, with the presence of 5% FBS. After 1 hour, media was changed to 2% FBS containing media and 150 moi of viruses were added. ACMs were maintained in media containing 2% FBS until harvesting. Beta-galactosidase staining was performed on 4% PFA-fixed ACMs that were incubated in 5 mM K+ fend-cyanide, 5 mM K+ferro-cyanide, 2 mM MgCl2, and 1 mg/mL X-gal for 4 hours.

Temporally-controlled KDM4D induction. Doxycycline-containing chow (Harlan TD.00502) was administered ad lib for the indicated times. Note that the Dox 2 weeks-9 weeks group includes mice that received dox ranging from P14-9w to P18-9w.

Myocardium and LV area quantification. Vibratome sections were cut from the mid-papillary muscle plane of hearts and imaged. Myocardium area and LV chamber area were manually traced in ImageJ and area was calculated using the "measure" tool.

Quantification of apoptosis. Apoptosis was visualized in vibratome sections by using a TUNEL staining kit (Life Technologies C10618) according to the manufacturer's guidelines. Following TUNEL labeling, we stained for WGA, Hoechst, and phalloidin, and imaged as described in the procedures for vibratome sections.

Results

Characterization of H3K9me3 Histone Demethylase Expression in CMs.

To better understand the role of H3K9me3 in regulating cell cycle gene expression, we characterized the relationship between cell cycle and H3K9me3-HDM gene expression in CMs through cardiac development (FIG. 1). Developmental changes in CM-specific and cell cycle gene expression included switching of myosin isoforms and dramatic down-regulation of G2/M and cytokinesis genes in ACMs (FIGS. 1A and B), consistent with prior studies (9,53,54). Cell cycle transcription factor E2F1 was downregulated 167-fold in ACMs ($P<0.0001$, vs. E15.5 CMs), while expression of repressive E2F4 remained high (FIG. 1C). Consistent with prior studies in skeletal muscle (35) and CMs (9), we found p107 was the Rb-family-member that was expressed specifically in proliferative myocytes, in contrast to Rb and p130 (FIG. 1C). Expression of KDM4 family members followed a similar, though less dramatic, pattern of expression as fetal CM, G2/M, and cytokinesis genes, and was moderately downregulated after P7 (FIG. 1D), coinciding with loss of CM regenerative potential (2,3). Downregulation of H3K9me3-HDMs in ACMs is consistent with the increase of global H3K9me3 levels in ACMs compared to embryonic CMs (9). The low basal level of KDM4D ACMs is consistent with other reports of KDM4D expression in tissues with limited proliferative potential (55,56).

To screen for HDMs that might be involved in CM proliferation, we looked for HDMs that were upregulated during CM dedifferentiation, as dedifferentiation appears to be a requisite for CM proliferation in the zebrafish and neonatal mouse heart regeneration models (1-3). Dedifferentiation of mammalian ACMs can be achieved in vitro by long-term culture with growth factors, resulting in disassembly of sarcomeres and restoration of proliferative potential (57). From a panel of diverse HDMs, KDM4D was the most highly upregulated (401-fold) during dedifferentiation (FIG. 1E; $P<0.03$). Because KDM4A expression is elevated in human hypertrophic cardiomyopathy samples and CM-specific KDM4A overexpression exacerbated hypertrophic growth in mice (49), we wondered if KDM4D was upregulated in human ischemic myocardium. KDM4D expression was unchanged in hearts of subjects with ischemic cardiomyopathy (FIG. 1F), consistent with the exceedingly low CM hyperplasia in this setting (58).

Generation of a Transgenic Mouse Model to Deplete H3K9me3 Specifically in CM

Figures 2A, 2B, 2C, 2D:
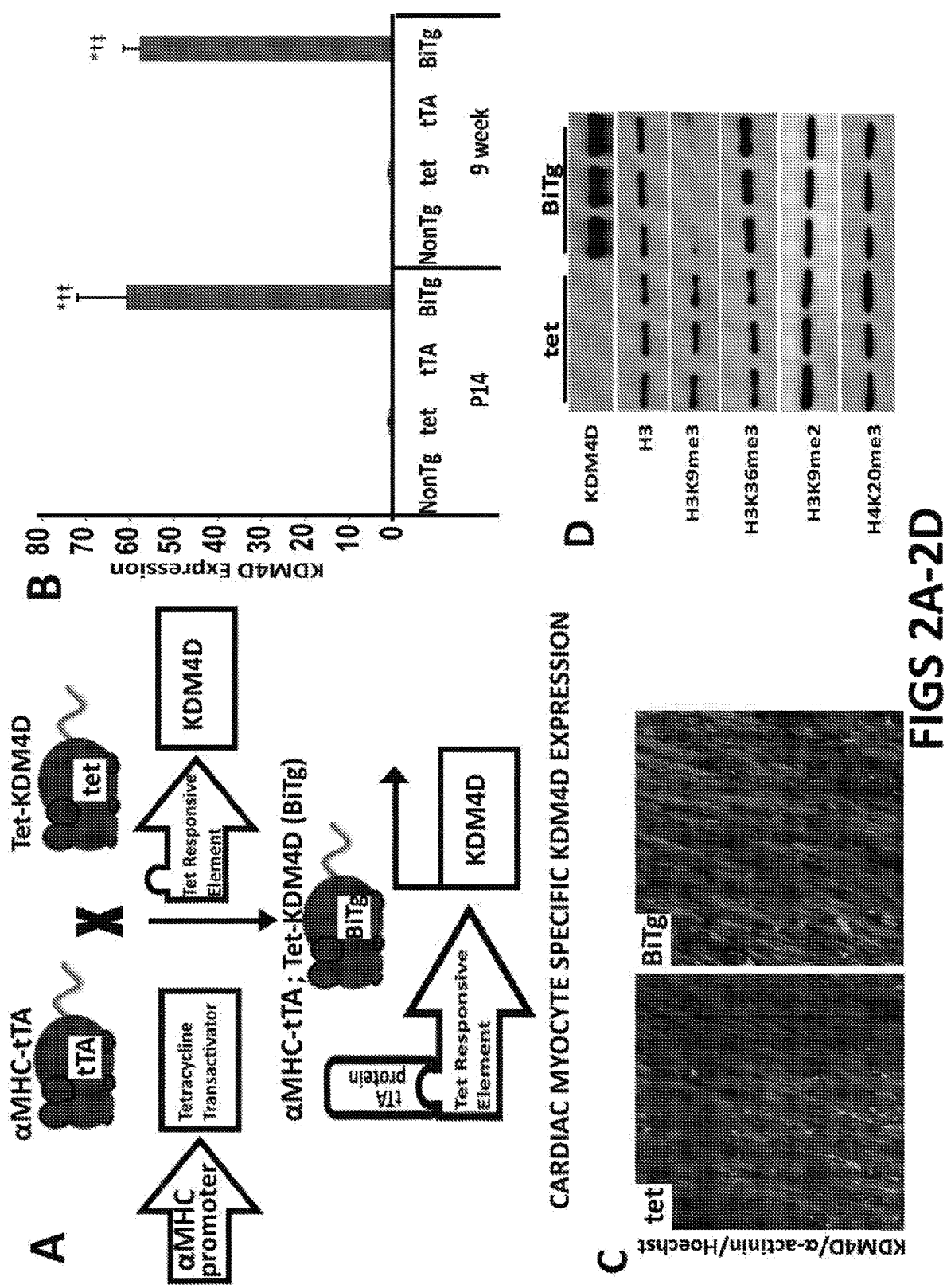
FIGS. 2A-2D. Generation of cardiac myocyte-specific KDM4D model. (2A) Schematic showing breeding strategy resulting in BiTg mice, and KDM4D induction in BiTg CMs. (2B) KDM4D transgene expression is robustly induced in BiTg ACMs and P14 hearts, fold induction vs. tet control. (2C) BiTg mice display nuclear KDM4D (FLAG-tag) localization specifically in CMs. (2D) KDM4D protein induction and global levels of specific histone methylations in 9-week ACMs. Sample Number: (2B-2D) Each assay had animals per group. Statistics: One-way ANOVA/Tukey's test, *$P<0.05$ vs NonTg, †$P<0.05$ vs tet, ‡$P<0.05$ vs tTA.
Figure 10A:
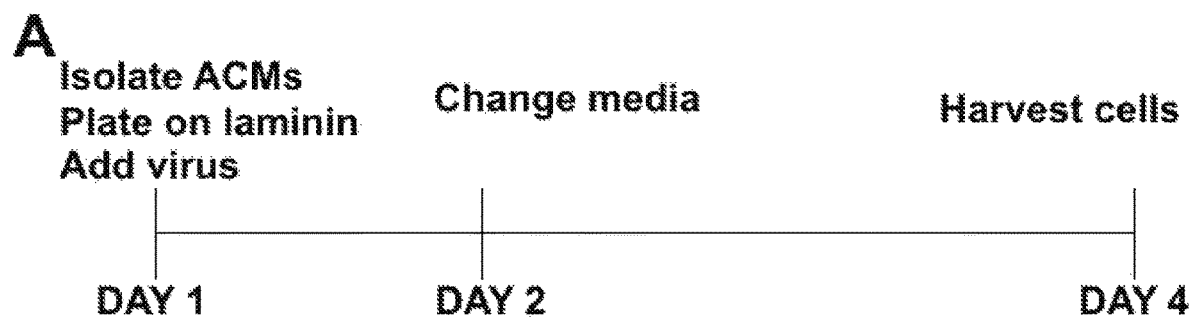
FIGS. 10A-10C. KDM4A demethylates H3K9me3 and H3K36me3 in ACMs. (10A) Timeline showing adenovirus-mediated KDM4A overexpression protocol in cultured WT ACMs. (10B) β-galactosidase staining in (top) uninfected and (bottom) lacZ-infected ACMs, showing >80% infection efficiency. (10C) Immunoblot showing KDM4A-expressing ACMs have global reductions in H3K9me3 and H3K36me3, but not in H3K27me3 (Millipore 07449). Lamin A/C (Cell Signaling 47775) and H3 were used as loading controls. Sample Number: N≥3 for each group.
Figure 10B:
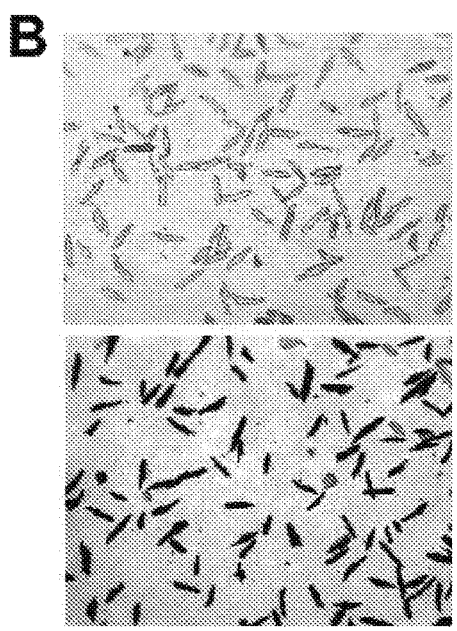
Figure 10C:
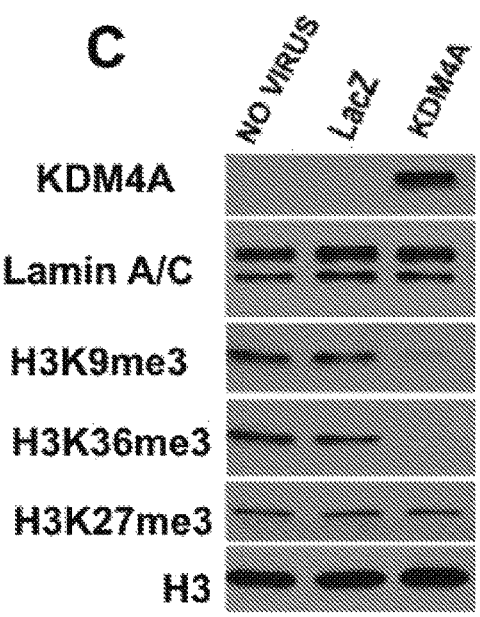
Figures 11A, 11B:
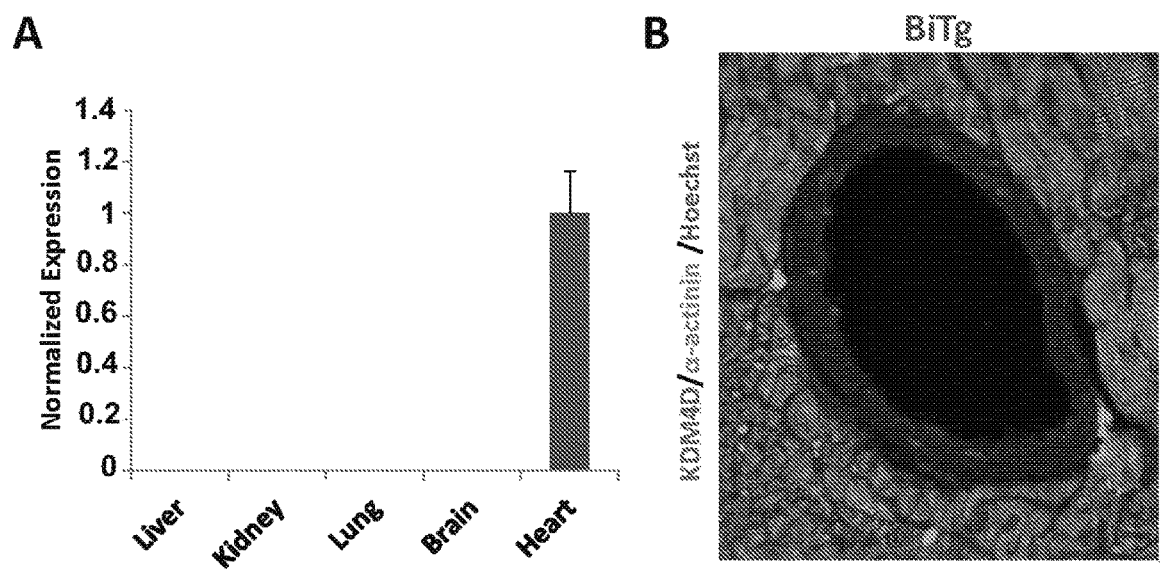
FIGS. 11A-11B. CM-specific KDM4D transgene expression. (11A) KDM4D transgene expression in various BiTg tissue samples at 9 weeks of age, normalized to expression levels in BiTg hearts. (11B) Exogenous KDM4D (FLAG-tag) immunostaining showing lack of expression in non-CM cardiac cells.

To explore the role of H3K9me3 in ACM cell cycle gene silencing in vivo, we chose to overexpress KDM family member 4D because: 1) KDM4D is the most specific H3K9me3 demethylase (50-52) (FIG. 10), 2) it is expressed in proliferative CMs and elevated in dedifferentiated ACMs (FIGS. 1, D and E), 3) it is not expressed in cardiomyopathy samples where hypertrophic growth would predominate (FIG. 1F), 4) it promotes proliferation and survival in non-CMs (46-48), and 5) gain of function experiments are less subject to compensation by redundant factors (59). We used a previously characterized tetracycline inducible (tet-off) overexpression model where the tetracycline transactivator (tTA) is expressed specifically in CMs. (60). We generated a CM-specific transgenic mouse line containing a MYC-and FLAG-tagged KDM4D cDNA downstream of a tetracycline responsive promoter, which contains tTA-binding sequence in the context of an attenuated-αMHC promoter (60). Breeding heterozygous tTA mice with heterozygous tet-responsive KDM4D (tet) mice yields bi-transgenic (BiTg) mice that constitutively express KDM4D specifically in CMs (FIG. 2A) as well as single-transgenic (tet or tTA) and non-transgenic (NonTg) controls. In BiTg CMs, the tTA protein is expressed and binds to the tet-responsive element upstream of KDM4D, inducing KDM4D transgene expression (FIG. 2A). We confirmed that KDM4D expression was robustly induced in BiTg hearts at P14 and 9 weeks (FIG. 2B). KDM4D transgene expression was not detectable in other organs in BiTg mice or non-CM cardiac cells (FIGS. 11, A and B), with the exception that low levels could be detected in BiTg lungs, consistent with previous reports using the αMHC promoter (60). Immunofluorescence imaging in heart sections showed exogenous KDM4D protein was specifically expressed and localized in the nuclei of BiTg CMs (FIG. 2C). Western blot analysis confirmed KDM4D protein expression and showed global H3K9me3 levels were depleted in BiTg ACMs (FIG. 2D). We also confirmed that in contrast to other KDM4 family members (FIG. 10), KDM4D demethylase activity is specific to H3K9me3 (50-52) and did not demethylate H3K9me2 or H3K36me3 in ACMs (FIG. 2D). H4K20me3, which has been implicated as a repressive mark that is downstream of H3K9me3 and HP1 (61-63) was unchanged (FIG. 2D); although this does not rule out changes in methylation levels at specific gene loci.

H3K9me3 is required for ACM cell cycle gene silencing in vivo.

Figure 3A:
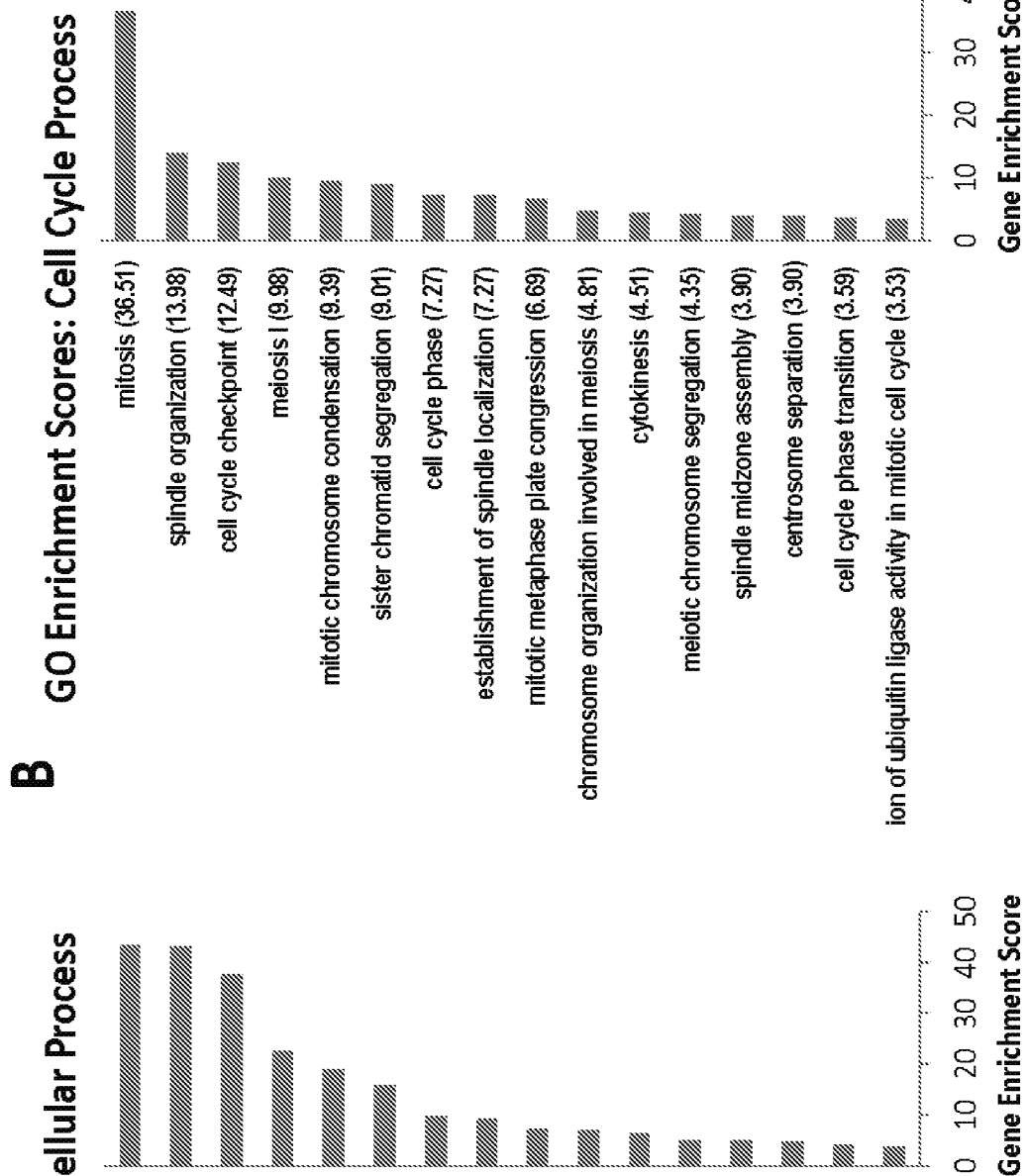
FIGS. 3A-3C. Gene expression in KDM4D-overexpressing ACMs. (3A) Gene Ontology Enrichment scores for "Cellular Process", and (3B) "Cell Cycle Process". GO enrichment scores were generated from lists containing all genes with >3 fold increase in BiTg ACMs at 9 weeks compared controls. (3C) Expression of CM and cell cycle genes in 9-week ACMs, fold induction vs. NonTg. Sample Number: (3A-3B) Control=2, BiTg=2. (3C) NonTg=3, tet=6, tTA=3, BiTg=5. Statistics: (3A-3B) One-way ANOVA was used to identify genes with significantly altered expression ($P<0.05$), Fisher's exact test was used to identify GO terms with significant enrichment scores ($P<0.05$). (3C) One-way ANOVA/Tukey's test, *$P<0.05$ vs NonTg, †$P<0.05$ vs tet, ‡$P<0.05$ vs tTA.
Figure 3B:
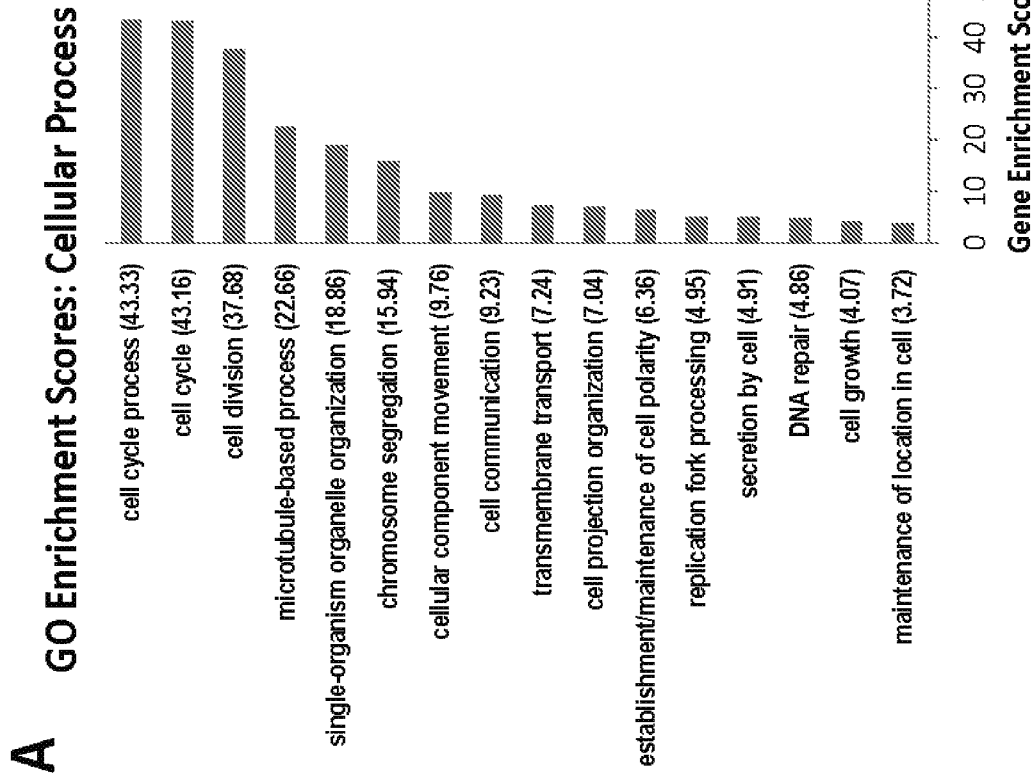
Figure 3C:
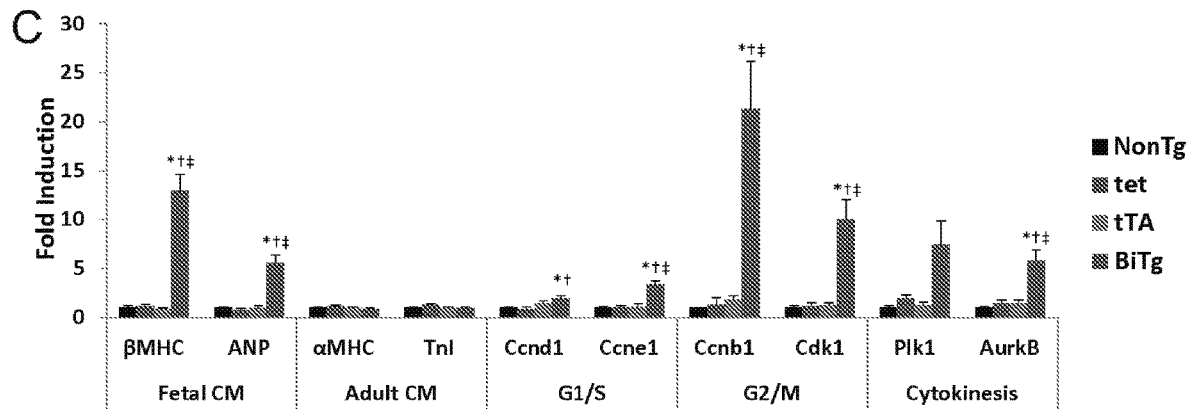
Figures 12A, 12B:
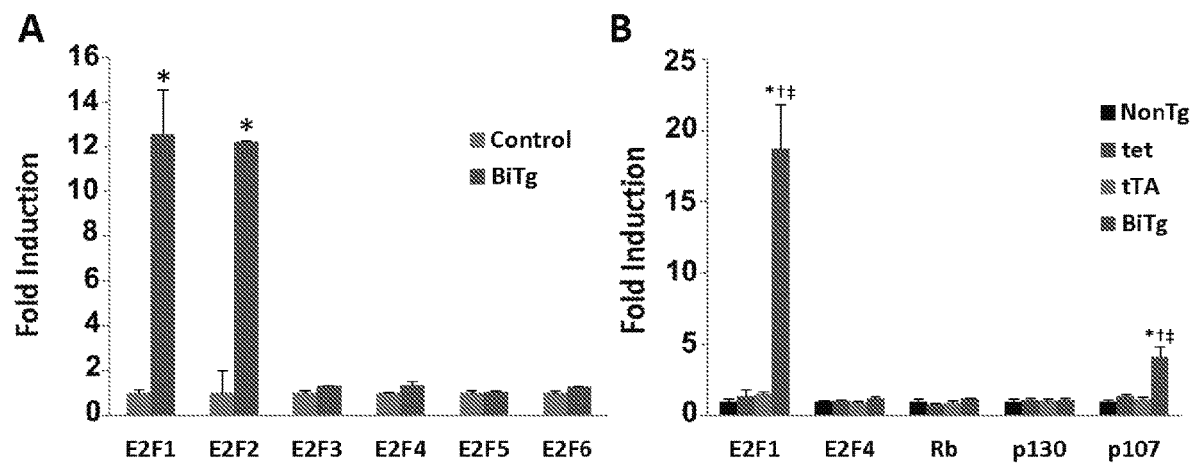
FIGS. 12A-12B. Cell Cycle Regulators in BiTg ACM. (12A) Gene expression (RNA-seq, RPKM, fold induction vs. control) of E2F family members in 9 week ACMs. (12B) qRT-PCR of cell cycle regulators in 9 week ACMs, fold induction vs. NonTg. Sample Number: (12A) N=2 per group, (12B) NonTg=3, tet=6, tTA=3, BiTg=5. Statistics: (12A) Two-tailed T-test, *$P<0.05$. (12B) One-way ANOVA/Tukey's test, *$P<0.05$ vs NonTg, †$P<0.05$ vs tet, ‡$P<0.05$ vs tTA.

To assess the impact of depleting H3K9me3 on global gene expression in vivo we performed RNA-sequencing on 9-week ACMs. Control ACM samples were grouped since NonTg and single transgenic mice showed no differences in gene expression, with the unconstrained slope correlation test showing $R2=0.9764$ when comparing the whole-genome transcriptome. RNA-seq analysis revealed that BiTg ACMs had increased expression of genes involved in 16 of 138 cellular processes and 16 of 142 cell cycle processes (FIGS. 3, A and B). Strikingly, cell processes involved in cell cycling were preferentially increased (FIG. 3A). Within cell cycle processes, categories involved in the later phases of cell cycle, particularly mitosis showed increased gene expression (FIG. 3B). We confirmed increases in G2/M and cytokinesis genes by qRT-PCR (5.8- to 21.4-fold, P<0.01) and fetal CM genes were also increased (FIG. 3C). Although the expression of fetal CM genes is frequently associated with a pathologic state, it should be noted that expression of less mature CM-specific genes could also be consistent with proliferation-competent CMs in fetal and neonatal hearts (9,64) (FIGS. 1A and B). We also examined cell cycle-gene transcriptional regulators (FIGS. 12A and B) and found that positive regulators of cell cycle progression, E2F1 and E2F2, were highly expressed in BiTg ACMs compared to control ACMs (>12-fold, P<0.03). The repressive E2F members, E2F4-6, were unchanged. Interestingly, p107 was also increased in BiTg ACMs (FIG. 12B), consistent with the E2F/Rb-family expression in proliferative myocytes (FIGS. 1B and C).

CM-Specific H3K9me3 Depletion Promotes CM Hyperplasia without Altering Cardiac Function.

Figures 4A, 4B, 4C, 4D, 4E:
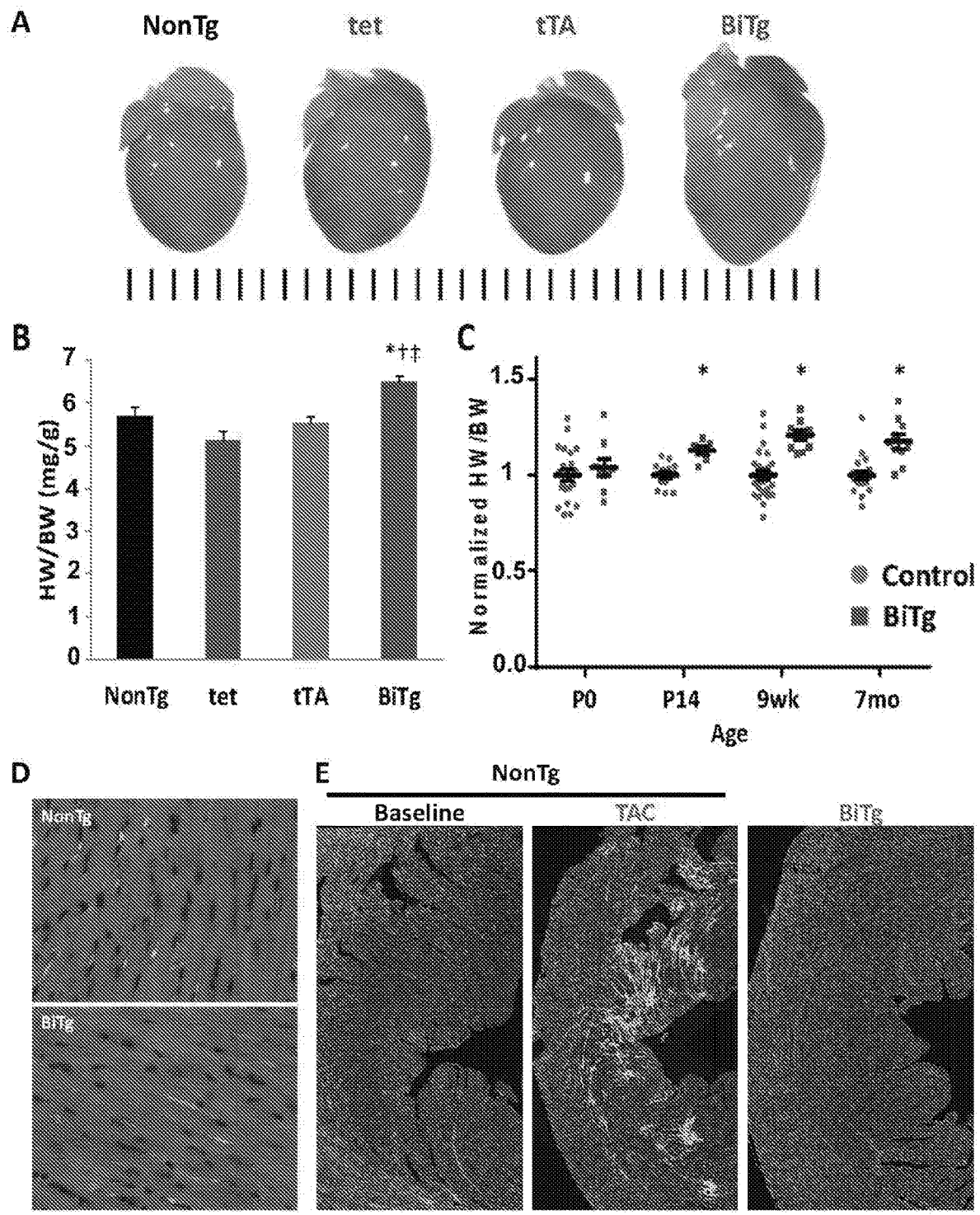
FIGS. 4A-4E. Heart mass is increased in KDM4D induced mice. (4A) Representative image showing PFA-fixed BiTg and control hearts at 9 weeks, tick marks=1 mm. (4B) Quantification of HW/BW at 9 weeks showing cardiac growth phenotype is specific to BiTg mice. (4C) Quantification of HW/BW in different ages of mice, normalized to controls for each time point. (4D) H&E staining in 9-week NonTg and BiTg hearts. (4E) WGA staining in 9-week NonTg and BiTg hearts, and 4 weeks post-TAC surgery in NonTg mice resulting in visible fibrosis. Sample Number: (4A-4B) NonTg=6, tet=11, tTA=9, BiTg=10. (4C) P0, Control=22, BiTg=9; P14, Control=14, BiTg=6; 9 wk Control=26, BiTg=10; 7 mo Control=19, BiTg=10. (D-E) Representative images from N≥3 for each group. Statistics: (4B) One-way ANOVA/Tukey's test, *$P<0.05$ vs NonTg, †$P<0.05$ vs tet, ‡$P<0.05$ vs tTA. (4C) Two-tailed T-test, control vs. BiTg, *$P<0.05$.

BiTg mice had visibly larger hearts (FIG. 4A) with a 20.8% increase in heart weight to body weight ratio (HW/BW) at 9 weeks (FIG. 4B; P<0.0001). This increase in HW/BW first became apparent in BiTg mice at P14 (FIG. 4C; 12.9% increase, P<0.001); suggesting KDM4D overexpression specifically promoted postnatal cardiac growth. This cardiac enlargement was not associated with sarcomere disarray, fibrosis or alteration of vasculature (FIGS. 4D and E) and there was no increase in extracellular matrix (65) (FIG. 4E). Quantification of ACM transverse area or direct measurements of isolated ACM longitudinal area and length did not reveal differences in dimensions or calculated volumes in BiTg ACMs compared to controls (FIG. 5A-D). Calculated myocyte number suggested BiTg hearts had 22% more ACMs compared to controls (FIG. 5E; P<0.03). To determine the longterm effect of H3K9me3-depletion on heart function, we performed echocardiography on 7 month old BiTg and control mice: ejection fractions, fractional shortening, cardiac output, and left ventricle chamber size were similar in all groups (Table 1). No significant differences in cardiac function or morphology were seen.

TABLE 1

Normal cardiac function and morphology in BiTg mice at 7 months. Echocardiography results in 7 month old mice. HR: Heart Rate, EF: Ejection Fraction, CO: Cardiac Output, LVEDD: Left Ventricular End-Diastolic Dimension, LV Mass: Left Ventricular Mass. Mean and SEM values are shown. Sample Number: N = 3 for each genotype. Statistics: One-way ANOVA/Tukey's test, * P < 0.05 vs NonTg, †P < 0.05 vs tet, ‡P < 0.05 vs tTA.

|  | NonTg | tet | tTA | BiTg |
|---|---|---|---|---|
| HR (BPM) | 440 ± 10 | 461 ± 16 | 452 ± 6 | 404 ± 3†‡ |
| EF (%) | 74.5 ± 3.7 | 80.9 ± 1.6 | 83.8 ± 2 | 80.2 ± 4.6 |
| FS (%) | 42.7 ± 3.2 | 48.9 ± 1.6 | 52.3 ± 2.2 | 48.8 ± 4.9 |
| CO (mL/min) | 16.4 ± 1.4 | 20.5 ± 1 | 17.4 ± 1.5 | 19.1 ± 0.7 |
| LVEDD (mm) | 3.47 ± 0.06 | 3.61 ± 0.02 | 3.35 ± 0.15 | 3.73 ± 0.07 |

Figures 6A, 6B, 6C, 6D:
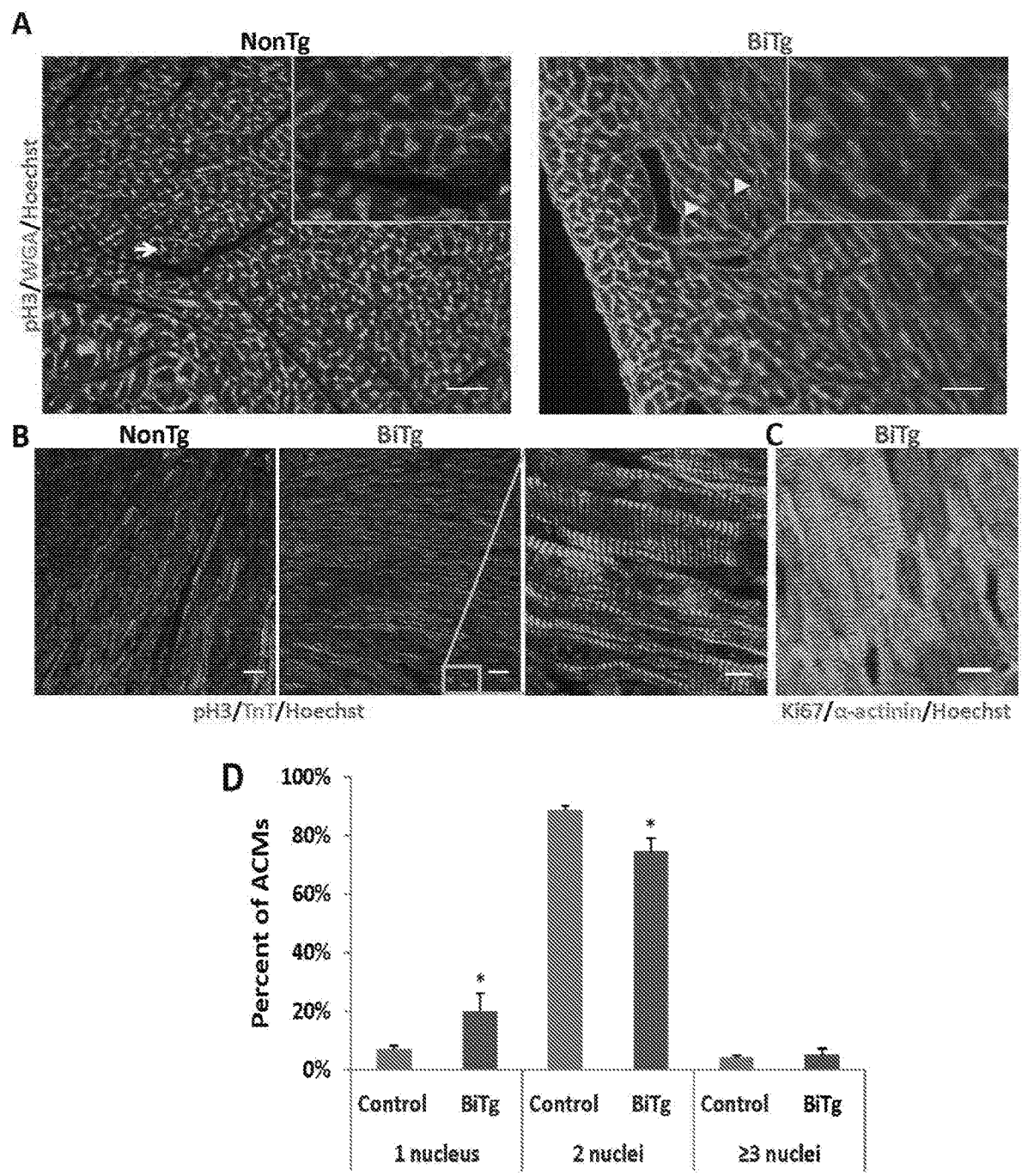
FIGS. 6A-6D. Persistent low level cardiac myocyte cell cycle activity in adult BiTg hearts. Mitotic marker phospho-H3 (pH3) staining in NonTg and BiTg heart sections (6A) at P14 and (6B) 9 weeks, bar=40 μm. (6A) White arrows point to pH3+ non-CM nuclei, yellow arrowheads point to pH3+ CM nuclei. (6B) Right, high magnification of boxed region, bar=10 μm. (6C) Cell cycling marker Ki67 in 9-week BiTg hearts, bar=10 μm. (6D) Quantification of nuclei number in 7 month old ACMs. Sample Number: (6A-6D) Each assay had ≥3 animals per group. Statistics: (6D) Two-tailed T-test, control vs. BiTg, *$P<0.05$.

To assess cell cycle activity, we immunostained P14 and 9 week myocardial sections for phosphorylated histone H3 serine-10 (pH3), a marker of mitosis. We observed pH3+ CMs only in BiTg mice at both time points (FIGS. 6A and B). Similar trends were seen for the general cell cycle activity marker Ki67 in 9 week hearts (FIG. 6C). Quantification of the number of nuclei per ACM at seven months revealed there was an increase of mononucleated and a decrease in binucleated ACMs in BiTg hearts (FIG. 6D). These findings are consistent with a model where the increased heart mass in BiTg mice was secondary to CM hyperplasia.

Figure 7A:
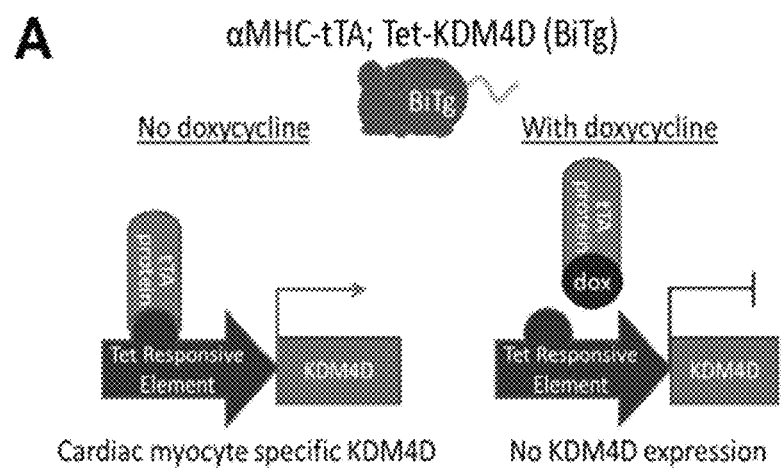
FIGS. 7A-7D. KDM4D expression induces hyperplastic growth in adult BiTg hearts. (7A) Schematic showing usage of doxycycline for temporal control of CM-specific KDM4D expression in BiTg mice. (7B) Timeline showing protocol for development-restricted KDM4D expression. (7C) KDM4D expression in 9 week or 3 week ventricles of doxycycline (dox) treated mice, fold induction compared to tat control. (7D) HW/BW at 9-weeks in mouse models where CM-specific KDM4D expression is un-induced (Dox E0-9w), turned off at P14 (Dox 2w-9w), and constitutively expressed (no dox). Sample Number DoxE0-9w, Control=17, BiTg=4; Dox2w-9w, Control=11, BiTg=G; No dox, Control=26, BiTg=10. Statistics: Two-way ANOVA/Tukey's test, *$P<0.05$ vs DoxE0-9w control and BiTg, Dox2w-9w control and BiTg, and no dox control.
Figure 7B:
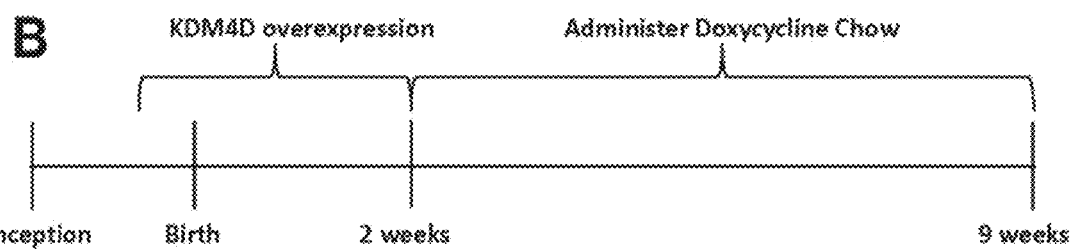
Figure 7C:
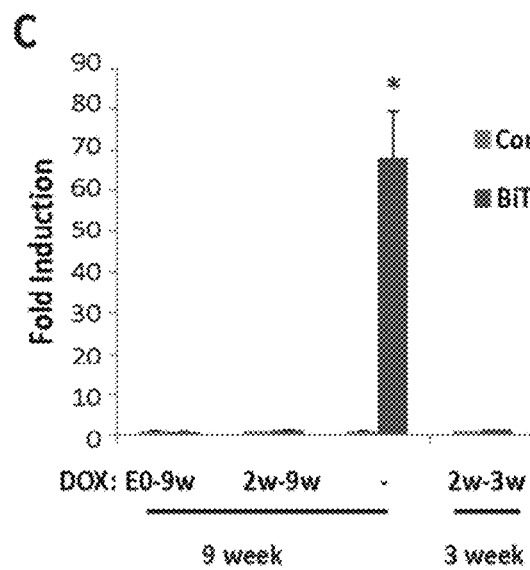
Figure 7D:
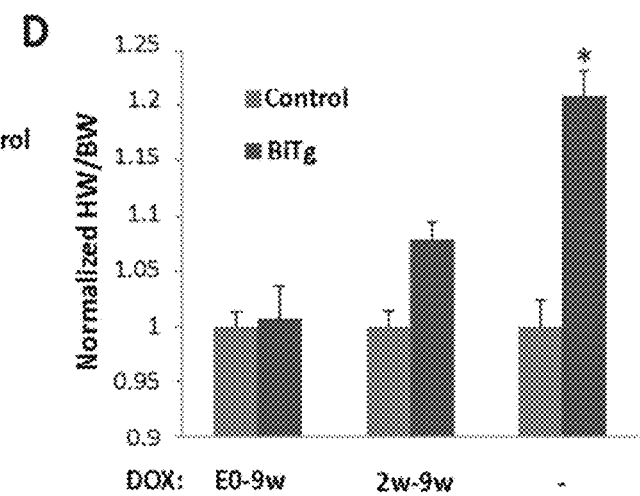

Cardiac mass increased up to 9-weeks of age in BiTg mice (FIG. 4C). Cell cycle activity in 9-week BiTg ACMs, though elevated compared to controls (FIGS. 6B and C), was rare (<2 pH3+ CM/200× field). To determine if the increased mass was related to the normal post-natal hypertrophic growth of an increased number of CMs in BiTg hearts or whether there was ongoing CM hyperplasia we utilized doxycycline (Dox) to shut-off KDM4D expression (FIG. 7A). We examine heart mass in BiTg mice where KDM4D expression was never induced or was induced in utero but suppressed at P14 (FIG. 7B). Dox treatment reduced KDM4D expression in BiTg ventricles to control levels within one week (FIG. 7C). Adult BiTg mice that had KDM4D expression suppressed since conception displayed HW/BWs that were indistinguishable from controls (FIG. 7D). BiTg hearts with constitutive KDM4D expression were larger at P14 (FIG. 4C; 12.9% increase vs. control; P<0.001). However, when KDM4D expression was turned off at 2 weeks, heart size at 9 weeks was less compared to mice with constitutive KDM4D expression (FIG. 7D; 7.9% vs 20.8%; P<0.05). These findings suggest that KDM4D overexpression continues to promote additional CM hyperplasia between weeks 2 through 9.

Hypertrophic Signals Stimulate Proliferation of H3K9me3-Depleted ACMs.

Figures 8A, 8B, 8C:
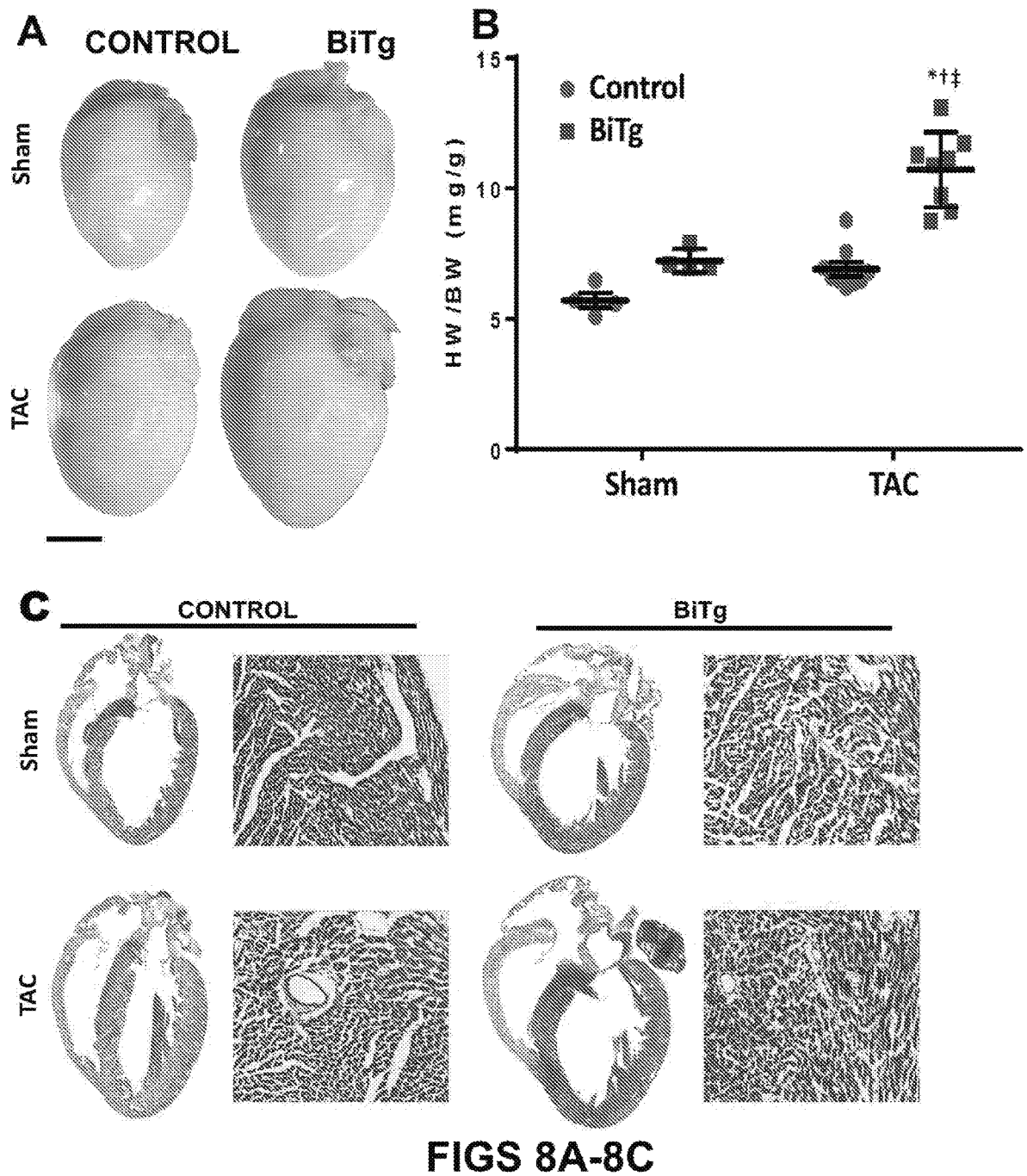
FIGS. 8A-8C. Hemodynamic load stimulates hyperplastic growth in BiTg hearts. (8A) Representative images of methanol-fixed hearts and (8B) HW/BW quantification of control and BiTg hearts at 10 days post-operation, bar=2 mm. (8C) Representative Masson Trichrome staining of operated mice. Sample Number Sham, Control=4, BiTg=4; TAC, Control=9, BiTg=8. Statistics: (8B) Two-way ANOVA/Tukey's test, *$P<0.05$ vs Sham-Control, †$P<0.05$ vs Sham-BiTg, ‡$P<0.05$ vs TAC-Control.
Figures 9A, 9B, 9C, 9D:
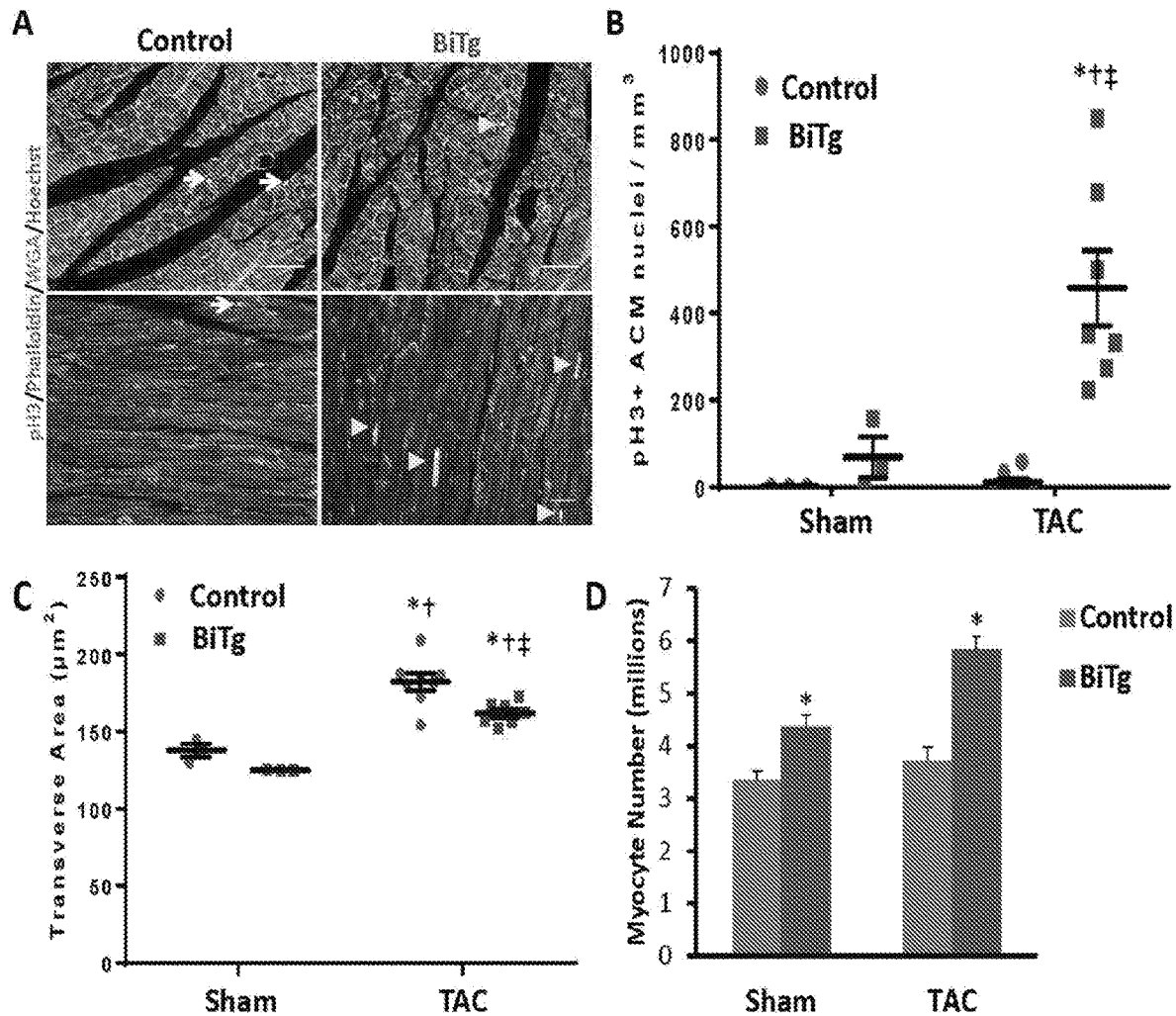
FIGS. 9A-9D. Pressure overload stimulates ACM mitotic activity in BiTg mice. (9A) Low and high magnification images of TAC hearts. Bar=40 µm (top) or 20 µm (bottom), white arrows point to pH3+ non-CM nuclei, yellow arrowheads point to pH3+ ACM nuclei. (9B) Quantification of ACM mitotic activity in control and BiTg hearts, 10 days post-operation. (9C) Quantification of ACM transverse area in methanol-fixed hearts, 10 days post-operation. (9D) Estimated myocyte cell number. Sample Number (9A-9D) Sham, Control=3, BiTg=3; TAC, Control=8, BiTg=7. Statistics: (9B,9C) Two-way ANOVA/Tukey's test, *$P<0.05$ vs Sham-Control, †$P<0.05$ vs Sham-BiTg, ‡$P<0.05$ vs TAC-Control. (9D) The Bootstrap method was used to compute standard error and Permutation test was used to compute p-value, *$P<0.05$ vs control.
Figures 13A, 13B:
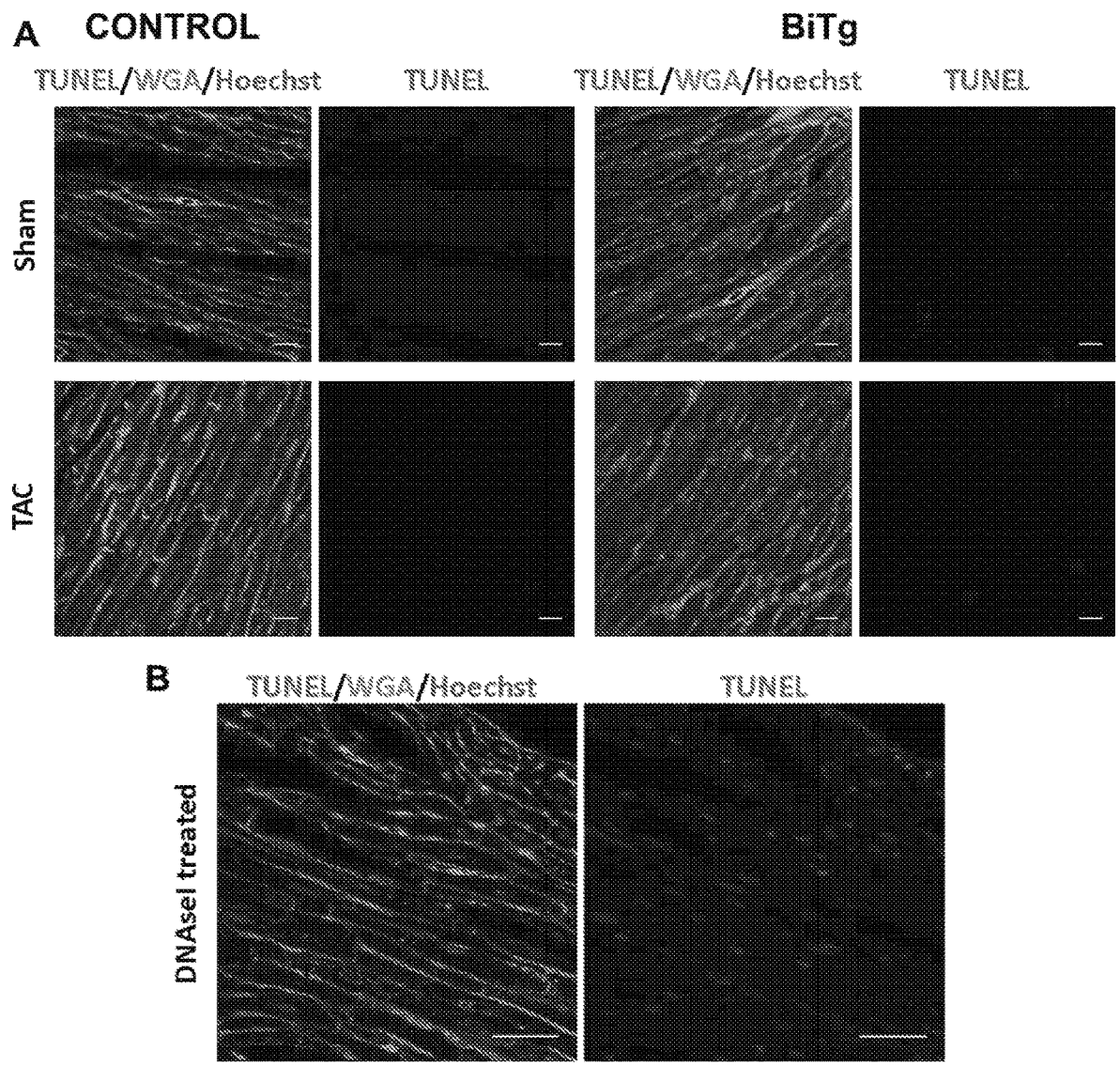
FIGS. 13A-13B. Apoptotic cells are not detected 10 days post-operation. (13A) Representative images of TUNEL staining in vibratome sections. (13B) DNAseI-treated heart sections of adult non-operated mice give robust nuclear-specific signal, showing our assay is able to detect TUNEL staining. Sample Number: N=2 for each group.
Figures 14A, 14B, 14C:
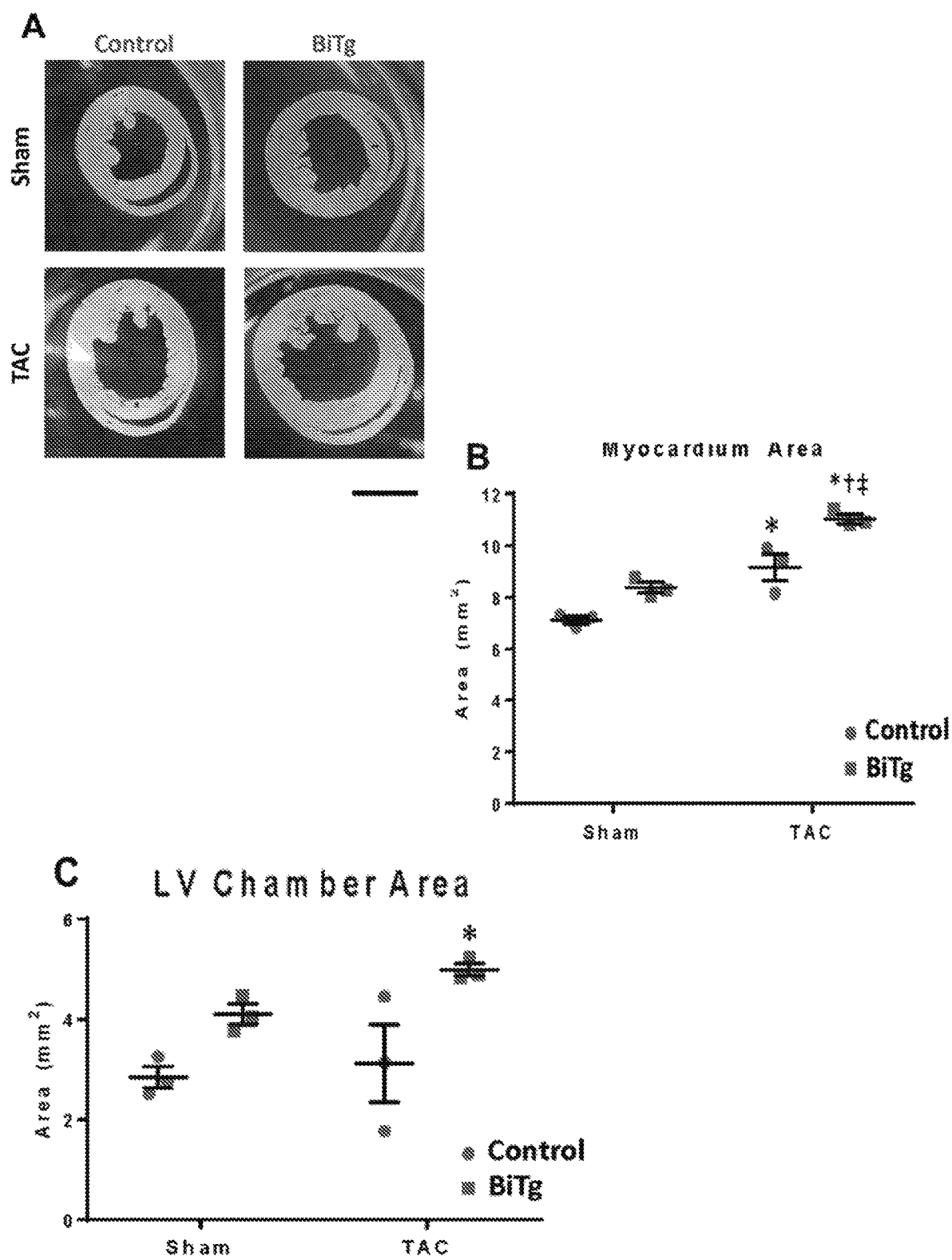
FIGS. 14A-14C. BiTg hearts have increased myocardium and dilated LV chambers. (14A) Representative images of mid-papillary vibratome sections, bar=2 mm. Quantification of (14B) myocardium area and (14C) LV chamber area. Sample Number: N=3 per group. Statistics: Two-way ANOVA/Tukey's test, *$P<0.05$ vs Sham-Control, †$P<0.05$ vs Sham-BiTg, ‡$P<0.05$ vs TAC-Control.

Although highly upregulated compared to controls, late cell cycle gene expression in BiTg ACMs is much less than in wildtype embryonic and postnatal CMs (compare FIG. 1B with FIG. 3C). Also the absolute number of cycling CMs, while increased in BiTg hearts, was low and normalized cardiac mass did not increase further between 9 weeks and 7 months (FIG. 4C) suggesting CM proliferation is very limited at baseline in adult BiTg hearts. Since there is robust activation of numerous growth factor signaling pathways post TAC that typically result in hypertrophic growth (9,66), we thought this might be an excellent model to test KDM4D's ability to promote ACM proliferation in vivo. This allowed us to determine whether a hypertrophic growth signal such as TAC would induce hyperplasia in H3K9me3-depleted ACMs or whether they would undergo hypertrophy similar to control hearts. BiTg and control littermates underwent sham or TAC surgeries at 11 weeks of age and were examined 10-days after surgery. Similar to un-operated mice sham-operated BiTg hearts were visibly larger than controls (FIG. 8A). TAC induced a 48.2% increase in HW/BW in BiTg mice compared to a 20.9% in control mice (FIG. 8B; P<0.0001). To determine if the TAC-induced heart growth occurred through ACM hypertrophy or hyperplasia, we measured ACM transverse area. Sham BiTg ACMs were similar to sham controls (FIG. 5A); however, with TAC BiTg ACM transverse area was 12.5% smaller compared to TAC control ACMs (FIGS. 9, A and C; P<0.05). Since ACM transverse area, but not length, is increased after TAC (67), we estimated CM number and found a 56.6% increase in ACMs in BiTg hearts compared to controls (FIG. 9D, P<0.001). To confirm that BiTg ACMs were cycling after TAC we assayed for phospho-H3 and observed a 41-fold increase in pH3+ ACMs in BiTg mice compared to control mice (0.77% vs 0.019%; P<0.0001) (FIGS. 9, A and B). This cell cycle activity was not associated with fibrosis (FIG. 8C and FIG. 9A) or increased apoptosis (FIG. 13). To determine if reinduction of CM cell cycling negatively impacted cardiac function, 2-D echoes were performed 9 days post-surgery (Table 2). Ejection fraction was decreased in BiTg mice after TAC along with and an increase in LVEDD. However, the calculated cardiac output was unchanged, presumably due to the chamber size in BiTg hearts (FIG. 14).

TABLE 2

Cardiac function and morphology in TAC-operated mice.
Echocardiography results in 12 week old mice, 10 days post-operation.
HR: Heart Rate, EF: Ejection Fraction, CO: Cardiac Output, LVEDD:
Left Ventricular End-Diastolic Dimension, LV Mass: Left Ventricular
Mass. Mean and SEM values are shown. Sample Number: Sham,
Control = 4, BiTg = 4; TAC, Control = 9, BiTg = 8.
Statistics: Two-tailed T-test, control vs. BiTg, *P < 0.05.

|  | Sham | | TAC | |
| --- | --- | --- | --- | --- |
|  | Control | BiTg | Control | BiTg |
| HR (BPM) | 428 ± 17 | 416 ± 7.6 | 430 ± 11 | 406 ± 10 |
| EF (%) | 71.1 ± 4.2 | 72.4 ± 3.7 | 75.5 ± 4.4 | 51.2 ± 3.7* |
| FS (%) | 39.5 ± 3.5 | 40.8 ± 3.4 | 43.7 ± 3.5 | 25.9 ± 2.3* |
| CO (mL/min) | 11.6 ± 2.4 | 12.4 ± 1.5 | 9.8 ± 0.9 | 10.9 ± 0.7 |
| LVEDD (mm) | 3.04 ± 0.14 | 3.19 ± 0.11 | 2.83 ± 0.09 | 3.57 ± 0.10* |

Discussion

Since the discovery that neonatal mammalian hearts can regenerate by CM proliferation (2,3) and that ACMs retain some, though very limited, capacity to divide (7), interest in the regulation of ACM cell cycle has been reignited (4,69-71). Many strategies that can promote proliferation in mammalian neonatal CMs have been ineffective in ACMs (72,73) highlighting the fact that strong barriers to proliferation exist in ACMs. Recently, epicardial paracrine factor FSTL1 (70), miR-15 inhibition (3), and the NRG1 co-receptor Erbb2 (74) were suggested to promote ACM proliferation, though the molecular mechanisms and relevant targets in ACMs remain elusive. We previously found that the heterochromatin marker H3K9me3 was enriched on G2/M and cytokinesis genes in ACMs compared to fetal CMs implicating this mark as a barrier to ACM proliferation (9). This example characterizes the expression of H3K9me3-demethylases in development, dedifferentiation, and disease and shows that KDM4D was expressed in fetal CMs and was the primary H3K9me3-specific demethylase upregulated in dedifferentiating ACMs. CM-specific KDM4D overexpression depleted H3K9me3 specifically and led to increases in ACM expression of G2/M and cytokinesis genes, cardiac mass, ACM number, and ACM mitotic activity.

The renewed interest in CM proliferation has also called attention to the need of improved methodologies for detecting ACM proliferation (75). The standard indicator of ACM proliferation has been indirect in situ histology of phase-specific or general cell cycle markers. However, it has been suggested these results are often equivocal because it can be difficult to determine if the marker is present in a CM or non-CM (75,76). Most studies are performed in cardiac sections less than 10 μm thick, which is significantly thinner than even the shortest axis of mammalian ACMs, and are further confounded by the dense myocardial vasculature and non-CMs that are the majority of cardiac cells (77). We addressed this limitation by developing a novel sample preparation and imaging technique that yields high-resolution 3D image reconstructions of cleared thick sections with several layers of whole ACMs, allowing unambiguous identification of mitotic ACMs in KDM4D overexpressing mice (FIG. 9). Our methods corroborate findings from in vivo cumulative-proliferation-labeling in CM lineage-tracing models (multi-isotope-mass-spectrometry (7), mosaic analysis with double markers (78), and multi-color clonal assays (76)) and supports the emerging consensus that ACM proliferation is rare and difficult to stimulate (75). Despite the fact that late cell cycle gene expression was markedly increased at 9 weeks in H3K9me3-depleted CMs (FIG. 3C) their expression levels were much lower when compared to neonatal CMs (FIG. 1B). As well, the vast majority of BiTg ACMs appeared to exit the cell cycle by P14 (FIG. 6A) and the difference in HW/BW compared to controls did not appear to increase further after 9 weeks (FIG. 4C). This suggests mechanisms, in addition to H3K9me3, prevent proliferation in ACMs.

This example confirms that H3K9me3 is required for ACM cell cycle gene silencing in vivo but that H3K9me3 is not sufficient by itself to explain the stable silencing of cell cycle genes in ACMs since it was maintained on G2/M and cytokinesis genes even after they were derepressed by Rb/p130 double knockout (9). In that study, HP1γ, whose chromodomain specifically binds H3K9me3, was displaced from late cell cycle gene promoters. This study suggested that stable silencing of cell cycle genes in ACMs required recruitment of HP1γ and that H3K9me3, though required, was not sufficient to silence genes (9). Since Rb and H3K9me3 are both required for HP1 binding in many systems it is possible that KDM4D overexpression derepressed late cell cycle genes in ACMs by removing HP1γ's binding-substrate from chromatin. Regardless, since Rb and H3K9me3 are present on numerous genes it remains unclear why late cell cycle genes are preferentially derepressed. It may perhaps be related to particular combinations of E2F- and Rb-family members forming distinct complexes and targeting specific subsets of genes (33,34). In BiTg ACMs, this example showed that the E2F/Rb-family members most increased by H3K9me3-depletion were E2F1 and p107 (FIG. 12), which are the same E2F/Rb-family members that are specifically expressed in proliferative embryonic and neonatal CMs (FIG. 1C) (9). Consistent with HP1 losing the ability to target E2F-dependent genes in BiTg ACMs, p107, in contrast to Rb, has not been shown to bind HP1 (39). In agreement, Rb has additional protein-binding and phospho-regulated domains not found in p107, and deletion of p107 has not shown the hyperplasia phenotype seen with Rb loss of function (79;80). Thus, selective increases in E2F/Rb-family expression levels and differential recruitment of HP1 may explain the preferential increase of late cell cycle genes in BiTg ACMs.

This example demonstrated that ACMs can tolerate moderate levels of G2/M and cytokinesis gene expression without deleterious effects on heart function (FIG. 3 and Table 1). This is similar to other models of limited ACM cycling (76), but contrasts with our previous findings where disrupting heterochromatin formation and inducing cell cycle reentry in ACMs was associated with decreased heart function (9). A fundamental difference between the KDM4D mice and that model is that KDM4D overexpression specifically targets one methylation pathway, whereas Rb/p130 KO likely disrupted multiple epigenetic modifications (H3K9me3, H3K27me3, and H4K20me3) (9,32,33). This may explain why genes involved in promoting all phases of cell cycle were upregulated in Rb/p130 KO, while H3K9me3- or HP1γ-specific disruption leads to preferential increase of G2/M and cytokinesis gene expression(9) (FIG. 3). Consistent with this notion, H3K9me3-depleted chromatin in KDM4D mice maintained its global structure including heterochromatin unlike the Rb/p130 model with the exception of cycling pH3+ ACMs (FIG. 15). Thus, repressive methylations have overlapping roles in maintaining global chromatin structure in ACMs consistent with reports of H3K9me3-depletion in other cell types (27,81,82).

Figures 15A, 15B:
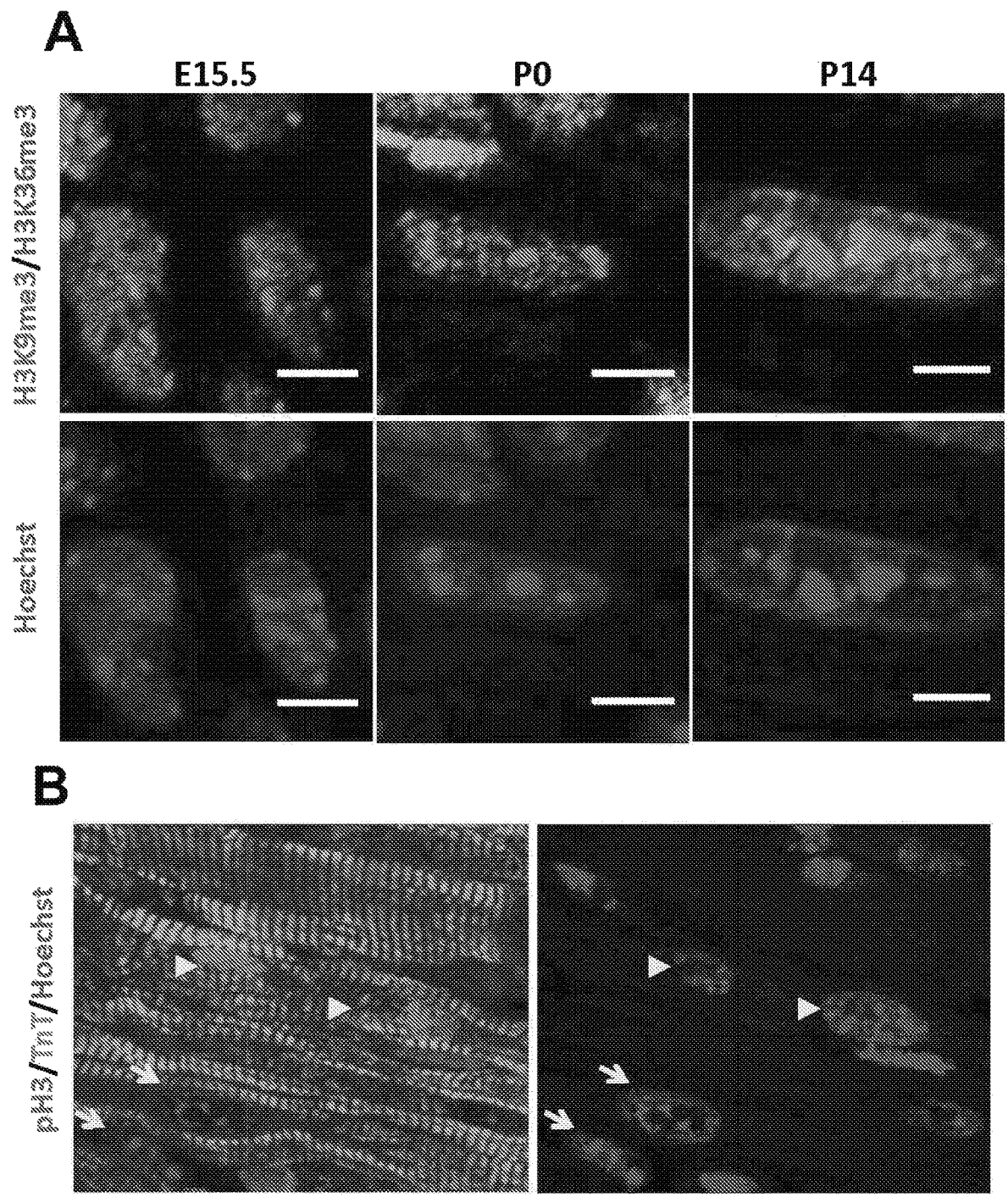
FIGS. 15A-15B. Unique chromatin structure in proliferative CMs. (15A) immunostaining in embryonic and postnatal wildtype heart sections showing anti-localization of heterochromatin marker H3K9me3 (Active Motif, 39161) with euchromatin marker H3K36me3 (Diagenode, C15200183); the change in chromatin organization during postnatal development is also seen, bar=5 µm. (15B) In BiTg heart sections, pH3+ ACM nuclei (arrowheads) display heterochromatin organization that resembles embryonic CMs, in contrast to the typical ACM chromatin organization (arrows).

We have suggested that there is a transition in heterochromatin structure during postnatal differentiation in ACMs (9) from limited heterochromatin organized into many small foci within the nucleus of embryonic CM, to few, large foci with additional heterochromatin at the nuclear lamina in postnatal CM nuclei (FIG. 15A). We found that the pH3+ ACMs in BiTg mice had a gross chromatin structure similar to that of proliferative embryonic CMs (FIG. 15B). The relationship between higher-order chromatin structure and gene-specific regulation is not clear, though studies suggest they act independently (27,82). Interestingly, H3K9me3 and H3K9me3-associated proteins also regulate cell cycle via transcription-independent mechanisms involving changes in global chromatin structure required for DNA synthesis and mitosis (42,83). Not surprisingly, pH3, the hallmark of mitotic activity, is inhibited by trimethylation of the adjacent amino acid residue H3K9 and double knockout of H3K9me3 methyltransferases Suv39h/12 resulted in increased pH3+ mouse embryonic fibroblasts (84,85), suggesting that global H3K9me3-depletion facilitates mitotic activity. Though several mechanisms may contribute to KDM4D-mediated ACM cell cycle activity, we have provided evidence that supports a model where cell cycle gene silencing is prevented by depleting H3K9me3, but additional repressors appear to prevent robust cell cycle activation in the absence of growth stimulation.

The results can be compared to findings in studies of another major cell proliferation regulation signaling pathway, the organ-size-controlling Hippo/Yap pathway. This pathway has been intensely studied with several CM-specific loss of function and gain of function mouse models through CM development and adulthood (71,93). Though Yap1 gain of function in adults increased ACM proliferation, the levels were 20-fold less than NonTg neonatal CMs (76). The authors postulated Yap activation alone is insufficient to overcome the multiple barriers blocking ACM proliferation. In several other systems Yap signaling fads to drive proliferation in the absence of E2F signaling (94-96). Interestingly, informatics and chromatin immunoprecipitation sequencing approaches found E2F- and Yap-binding sites neighbor each other on many cell cycle gene promoters (95-97), which suggests E2F and Yap might be parallel pathways. Indeed, in liver regeneration models enhanced E2F activation by triple knockout of the Rb-family members resulted in cell proliferation; however the increased proliferation declined over time due to dampening of Yap signaling (97). Forced Yap1 activation or reducing liver size by partial hepatectomy allowed the E2F-mediated increases in proliferation to persist. This suggests that the intrinsic Hippo/Yap pathway has a remarkable ability to sense and regulate normal organ size and that E2F-mediated increases in proliferation can be augmented by growth stimulation or Yap signaling. This is consistent with our finding that hemodynamic load, which increases active Yap levels (98) stimulated dramatic proliferation even in quiescent adult KDM4D hearts. Interestingly, endogenous Yap1 protein is expressed highly in postnatal CMs and is maintained at 8-weeks but lost by 20-weeks (99), which may account for the increases in HW/BW leveling out by 9-weeks in our model. The synergism of E2F and Yap activation is also consistent with a model of multiple blocks to ACM proliferation. Future studies examining the connectivity of the E2F/Rb-family and Hippo/Yap signaling pathways in CM cell cycle may clarify if H3K9me3 regulation of cell cycle genes is strictly E2F dependent. The relative importance of these pathways is speculative but growth signals that typically induce ACM hypertrophy caused re-induction of ACM proliferation in both H3K9me3-depleted ACMs and previously reported Yap1 mice (76). Although NonTg ACMs in the present example and these YAP-activated models had similar, very limited mitotic activity after growth stimulus (~0.02% (76) vs 0.019% FIG. 9B) we found substantially more mitotic BiTg ACMs after TAC than seen in Yap1-activated ACMs after MI (0.77% FIG. 9B vs 0.07% (76)). Whether all BiTg ACMs retained proliferative potential or there is a subset of highly proliferative ACMs is unclear but if pH3 signal is present for 3 hours of a 22 hour cell cycle (102) it would suggest that 5.7% of BiTg ACMs were actively cycling 10 days after TAC.

In conclusion, CM-specific KDM4D induction and the subsequent H3K9me3-depletion is sufficient to maintain proliferation competence in ACMs. These results further the understanding of how cardiac growth is regulated and identify a new role for H3K9me3 and common effector pathway for regulation of CM cell cycling. The fact that KDM4D overexpression did not affect normal heart function but allowed hyperplasia in response to hypertrophic signals supports the use of KDM4D to improve the regenerative response in clinical settings. This strategy is very amenable to gene therapies with localized and temporally controlled KDM4D expression and provides regenerative cardiac therapies.

Example 2

Neonatal Mouse Regeneration Model

Figure 16:
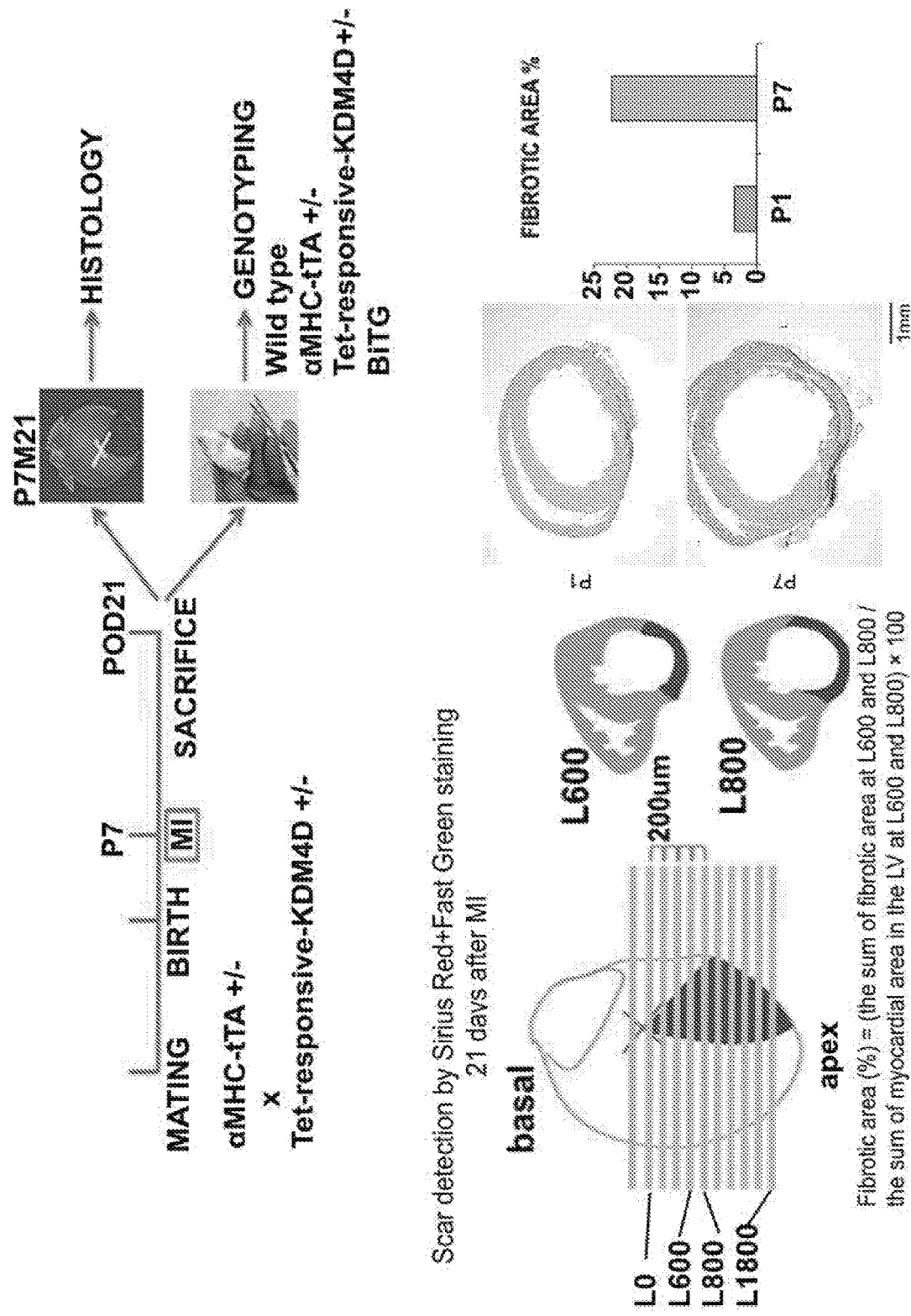
FIG. 16. Neonatal mouse regeneration model. Schematic in upper panel illustrates timeline for creating BiTG mice in which MI occurs at P7 and sacrifice at POD21 for histology and genotyping. Scar detection uses Sirius Red 4+Fast Green staining at 21 days after MI. Fibrotic area is analyzed as a percentage taken from (the sum of fibrotic area at L600 and L800/sum of myocardial area in the LV at L600 and L800)×100.
Figure 17:
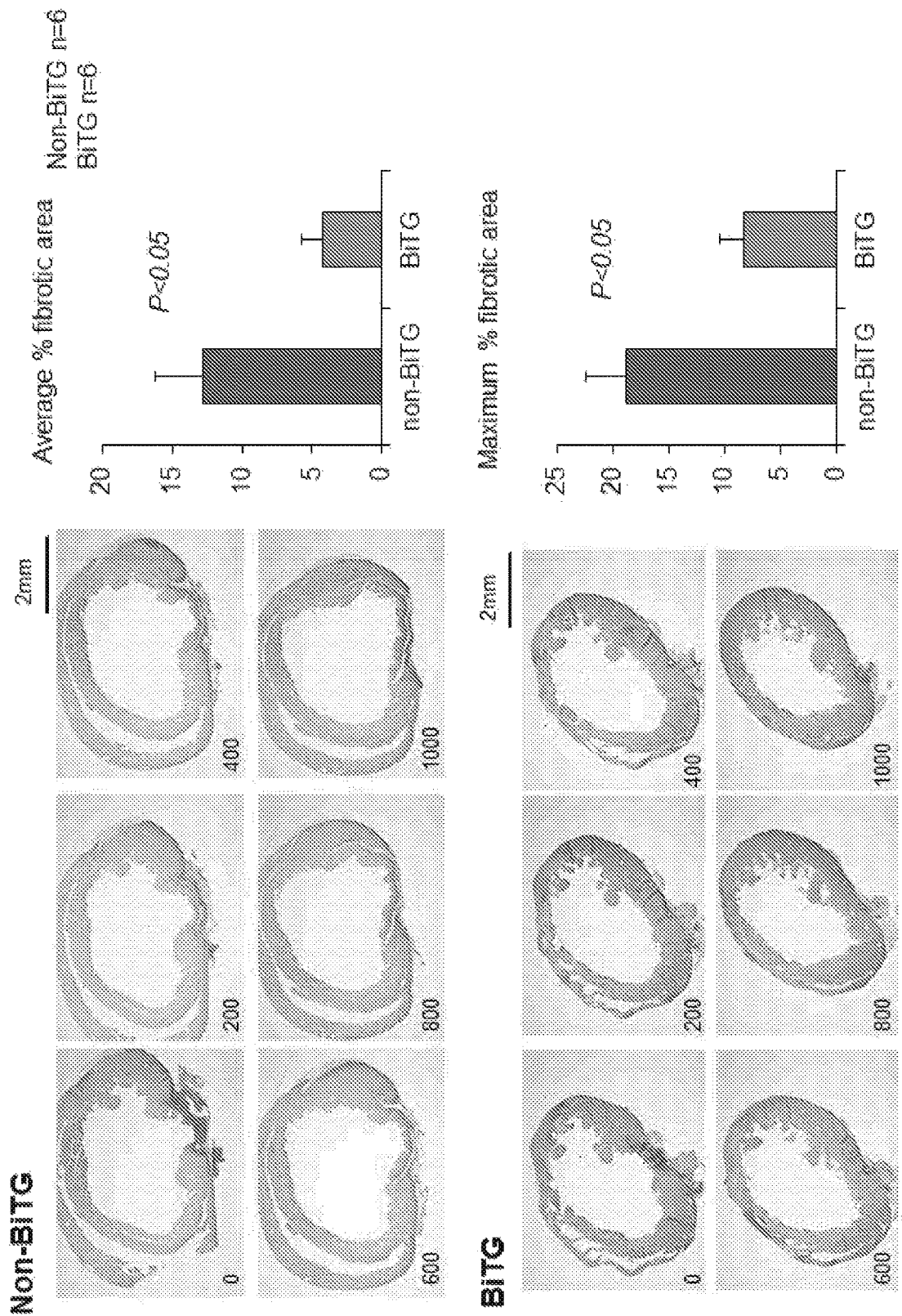
FIG. 17. KDM4 overexpressing mice have enhanced regeneration post-MI. Histological sections in left panels show Non-BiTG and BiTG samples taken at indicated L0 to L1000. Bar graphs on right panels show average and maximum percent fibrotic area for the two groups.
Figures 18A, 18B, 18C:
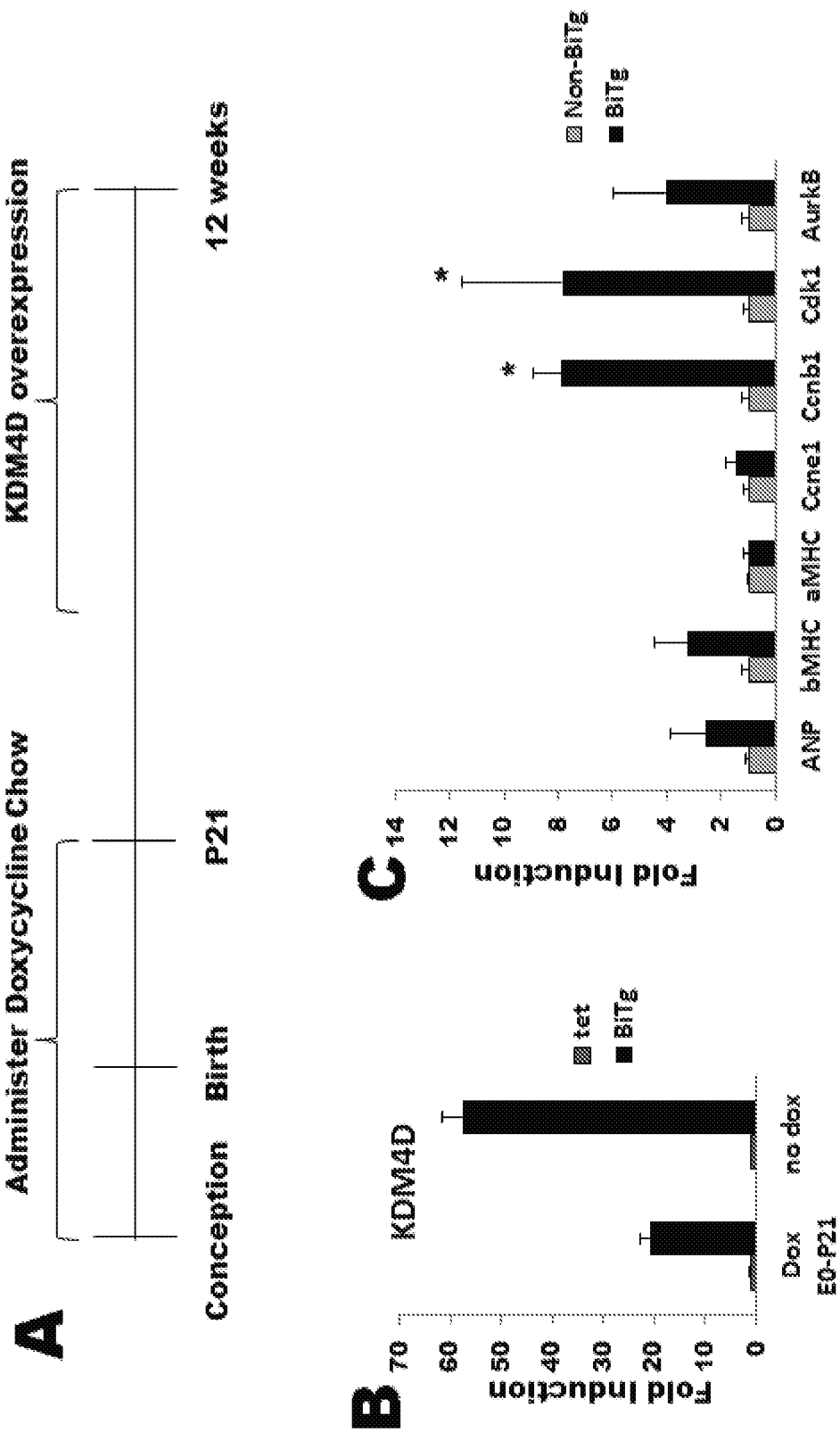
FIGS. 18A-18C. Adult CM-specific KDM4D Expression is sufficient to induce late cell cycle gene expression in ACMs. (18A) Schematic illustration of doxycycline administration through P21, and later KDM4D overexpression. (18B) Fold-Induction of KDM4D plotted for both tet and BiTg subjects, with doxycycline treatment at E0-P21, or without doxycycline treatment. (18C) Fold-induction of indicated genes for Non-BiTg and BiTg subjects.
Figure 19:
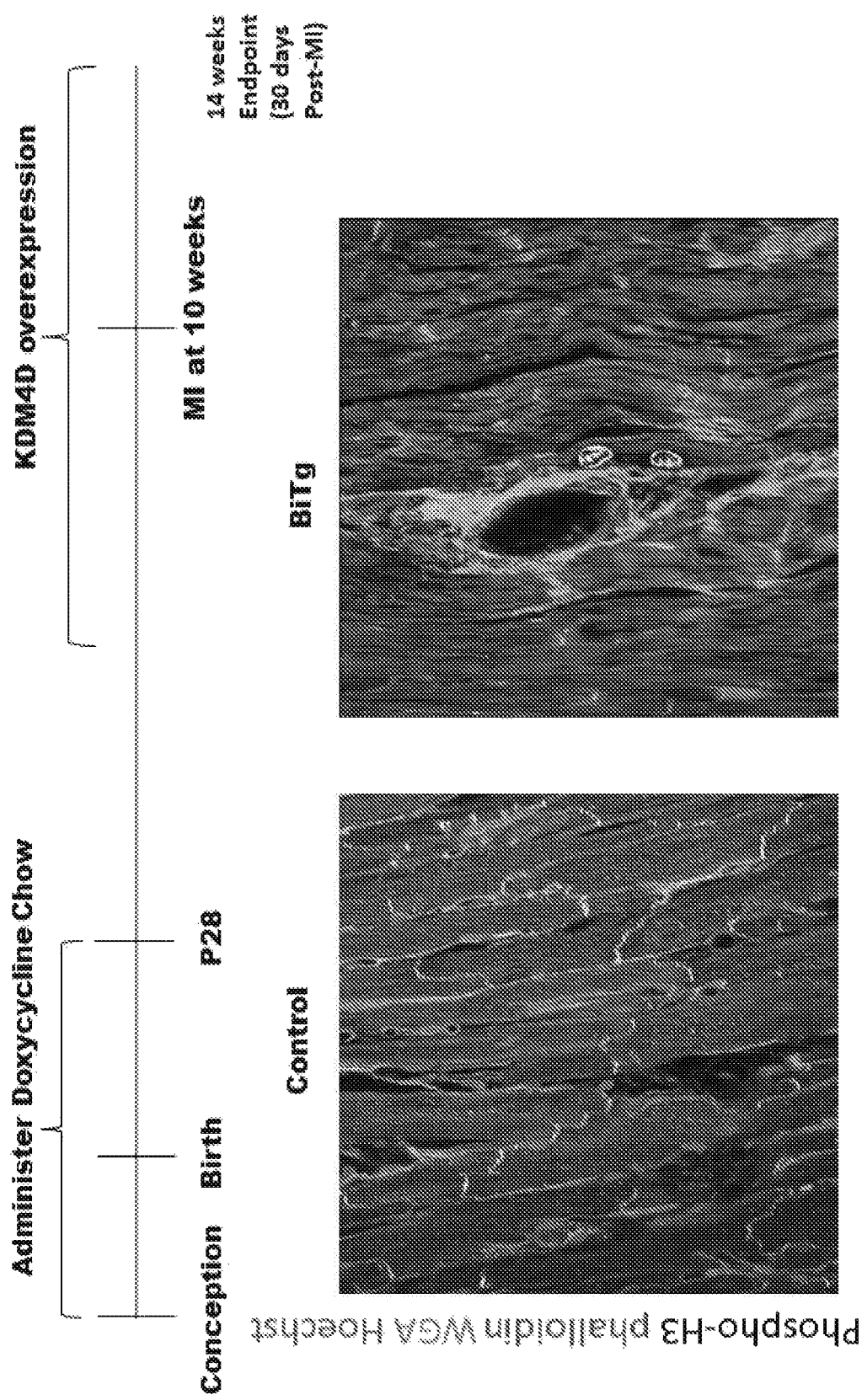
FIG. 19. Preliminary data showing adult CM-specific KDM4D expression and cell cycle activity post-MI. Doxycycline chow was administered from E0-P28. MI occurred at 10 weeks, during period of KDM4D overexpression, and at 14 weeks (30 days post-MI), tissue was examined for phospho-H3, phalloidin, WGA, and Hoechst, comparing control (left panel) and BiTg (right panel).

An animal model for regeneration of heart tissue is illustrated in FIG. 16. Using this model, mice overexpressing KDM4D show enhanced regeneration after myocardial infarct (MI) per histological analysis, as illustrated in FIG. 17. A statistically significant (p<0.05) reduction in both average fibrotic area and maximum fibrotic area was observed in KDM4D overexpressing mice compared to control mice at 21 days after MI. These data demonstrate the utility of KDM4D for regenerative therapy of cardiac tissues.

Example 3

Gene Therapy for Heart Regeneration

Vectors can be constructed for implementation and assessment of cardiac regeneration using gene therapy. The vectors can be constructed using AAV viruses, such as AAV6 or AAV9 or other hybrid AAV serotypes offering specificity for cardiac myocytes. A Troponin promoter is used for CM-specific expression. The AAV-KDM4D vector (expressing SEQ ID NO: 1 and optionally SEQ ID NO: 2) is injected into cardiac tissue at, or shortly after, the time of myocardial infarct. Assessment of heart function by echocardiography (ECHO) and cardiac magnetic resonance (CMR) is performed at subsequent time intervals to monitor recovery and regeneration. At the conclusion of the study, infarct size and ACM proliferation are assessed.

In one version of the construct, KDM4D can be shut off after a few weeks of regeneration to return KDM4D levels back to baseline, once lost CMs have been repopulated. Those skilled in the art will appreciate adjustments to the protocol that can be made to allow for alternative vectors and/or promoters that can achieve the same effect, as well as to allow for appropriate timing of the period of treatment before returning KDM4D levels back to baseline, taking into account individual circumstances such as the extent of damage and/or patient responsiveness.

REFERENCES

1. Jopling, C., et al. 2010. Nature 464:606-609.
2. Porrello, E. R., et al. 2011. Science 331:1078-1080.
3. Porrello, E. R., et al. 2013. Proc. Natl. Acad. Sci. U.S.A 110:187-192.
4. Xin, M., et al 2013. Proc. Natl. Acad. Sci. U.S.A 110:13839-13844.
5. Laflamme, M. A., and Murry, C. E. 2011. Nature 473:326-335.
6. Li, A. H., Liu, P. P., et al. 2014. Circ. Res. 1141916-927.
7. Senyo, S. E., et al. 2013. Nature 493:433-436.
8. Bergmann, O., et al 2009. Science 324:98-102.
9. Sdek, P., et al. 2011. J. Cell Biol. 194:407-423.
10. Angells, E., et al. 2008. Circ. Res. 102:1222-1229.
11. Zhong, W., et al. 2006. EMBO J. 25:3869-3879.
12. Ahuja, P., et al. 2007, Physiol Rev. 87:521-544.
13. Neufeld, T. P., and Edgar, B. A. 1998. Curr. Opin. Cell Biol. 10:784-790.
14. He, A., et al 2012. Circ. Res. 110:406-415.
15. Oyama, K., et al. 2014. Front Genet. 5:375.
16. Hohl, M., et al 2013. J. Clin. Invest 123:1359-1370.
17. Lee, S., et al. 2012. Dev. Cell 22:25-37.
18. Movassagh, M., et al 2011. Circulation 124:2411-2422.
19. Eulalio, A., et al. 2012. Nature 492:376-381.
20. Beisel, C., and Paro, R. 2011. Nat. Rev. Genet. 12:123-135.
21. Musselman, C. A., et al. 2012. Nat. Struct. Mol. Biol. 19:1218-1227.
22. Kouzarides, T. 2007, Cell 128:693-705.
23. Filion, G. J., et al 2010. Cell 143:212-224.
24. Margueron, R., et al. 2008. Mol. Cell 32:503-518.
25. Tessarz, P., and Kouzarides, T. 2014. Nat. Rev. Mol. Cell Biol. 15:703-708.
26. Simon, M., et al. 2011. Proc. Natl. Acad. Sci. U.S.A 108:12711-12716.
27. Chandra, T., et al 2012. Mol. Cell 47:203-214.
28. Solovei, I., et al. 2009. Cell 137:356-368.
29. Zhang, R., et al. 2007. Mol. Cell Biol. 27:2343-2358.
30. Giacinti, C., and Giordano, A. 2006. Oncogene 25:5220-5227.
31. Blais, A., and Dynlacht, B. D. 2007. Curr. Opin. Cell Biol. 19:658-662.
32. Gonzalo, S., et al 2005. Nat. Cell Biol. 7:420-428.
33. Macaluso, M., et al. 2006. Oncogene 25:5263-5267.
34. Bracken, A. P., et al. 2004. Trends Biochem. Sci. 29:409-417.
35. Blais, A., et al. 2007. J. Cell Biol. 179:1399-1412.
36. Xiao, G., et al. 2001. Circ. Res. 89:1122-1129.
37. Dahiya, A., et al. 2001. Mol. Cell 8:557-569.
38. Narita, M., et al. 2003. Cell 113:703-716.
39. Nielsen, S. J., et al 2001. Nature 412:561-565.
40. Whetstine, J. R., et al 2006. Cell 125:467-481.
41. Bannister, A. J., and Kouzarides, T. 2005. Nature 436:1103-1106.
42. McManus, K. J., et al. 2006. J. Biol. Chem. 281:8888-8897.
43. Mosammaparast, N., and Shi, Y. 2010. Annu. Rev. Biochem. 79:155-179.
44. Shi, Y., and Whetstine, J. R. 2007. Mol. Cell 25:1-14.
45. Berry, W. L., et al. 2012. J. Oncol. 41:1701-1706.
46. Berry, W. L., and Janknecht, R. 2013. Cancer Res. 73:2936-2942.
47. Kim, T. D., et al. 2012. PLoS. One. 7:e34618.
48. Shin, S., and Janknecht, R. 2007. Biochem. Biophys. Res. Commun. 359:742-746.
49. Zhang, Q. J., et al. 2011. J. Clin. Invest 121:2447-2456.
50. Hillringhaus, L, et al. 2011. J. Biol. Chem. 286:41616-41625.
51. Krishnan, S., and Trievel, R. C. 2013. Structure. 21:98-108.
52. Shin, S., and Janknecht, R. 2007. Biochem. Biophys. Res. Commun. 353:973-977.
53. Zhang, Y., et al. 2013. J. Regan. Med. 2:2.
54. Siedner, S., et al. 2003. J. Physiol 548:493-505.
55. Iwamori, N., et al. 2011. Biol. Reprod. 84:1225-1234.
56. Zhu, Y., et al. 2012. Mol. Cell 46:408-423.
57. Zhang, Y., et al. 2010. PLoS. One. 5:e12559.
58. Kaistura, J., et al. 1998. Proc. Natl. Acad. Sci. U.S.A 95:8801-8805.
59. Peters, A. H., et al 2001. Cell 107:323-337.
60. Sanbe, A., et al. 2003. et al Circ. Res. 92:609-616.
61. Schoeftner, S., and Blasco, M. A. 2009. EMBO 28:2323-2336.
62. Lange, U. C., et al. 2013. Nat. Commun. 4:2233.
63. Schotta, G., et al. 2004 Genes Dev. 18:1251-1262.
64. Kikuchi, K., et al. 2010. Nature 464:601-605.
65. Emde, B., et al. 2014. Eur. J. Histochem. 58:2448.
66. Esposito, G., et al 2010. Hypertension 55:137-143.
67. Qu, J., et a 2007. J. Mol. Cell Cardiol. 43:319-326.
68. Okada, K., et al 2004. Circulation 110:705-712.
69. Mahmoud, A. I., et al 2013. Nature 497:249-253.
70. Wei, K., et al 2015. Nature 525:479-485.
71. Zhou, Q., et al 2015. Circ. Res. 116:1431-1447.
72. Novoyatleva, T., et al. 2010. Cardiovasc. Res. 85:681-690.
73. Oh, H., et al. 2001. Proc. Natl. Acad. Sci. U.S.A 98:10308-10313.
74. D'Uva, G., et al 2015. Nat. Cell Biol. 17:627-638.
75. van Berlo, J. H., and Molkentin, J. D. 2014. Nat. Med. 20:1386-1393.
76. Lin, Z., et al 2014. Circ. Res. 115:354-363.
77. Zhou, P., and Pu, W. T. 2016. Circ. Res. 118:368-370.
78. Ali, S. R., et al. 2014. Proc. Natl. Acad. Sci. U.S.A 111:8850-8855.
79. Khidr, L., and Chen, P. L. 2006. Oncogene 25:5210-5219.
80. Knudsen, E. S., and Wang, J. Y. 1998. Oncogene 16:1655-1663.
81. Muramatsu, D., et al. 2013. J. Biol. Chem. 288:25285-25296.
82. Peters, A. H., et al 2003 Mol. Cell 12:1577-1589.
83. Black, J. C., et al 2010. Cell 40:736-748.
84. Rea, S., et al 2000. Nature 406:593-599.
85. Xu, D., et al. 2009. Cell Cycle 8:3688-3604.
86. Ponnaluri, V. K., et al. 2009 Biochem. Biophys. Res. Commun. 390:280-284.
87. Yang, L., et al. 2011. Cell 147:773-788.
88. Munro, S., et al. 2010. Oncogene 29:2357-2367.
89. Saddic, L. A., et al. 2010. J. Biol. Chem. 285:37733-37740.
90. Khoury-Haddad, H., et al. 2014. Proc. Natl. Acad. Sci. U.S.A 111:E728-E737.
91. Khoury-Haddad, H., et al. 2015. Cell Cycle 14:950-958.
92. Puente, B. N., et al 2014. Cell 157:565-579.

93. Lin, Z., and Pu, W. T. 2014. Stem Cell Res. 13:571-581.
94. Dick, F. A., and Mymryk, J. S. 2011. Genes Dev. 25:889-894.
95. Ehmer, U., and Sage, J. 2016. Mol. Cancer Res. 14:127-140.
96. Nicolay, B. N., et al. 2011. Genes Dev. 25:323-335.
97. Ehmer, U., et al. 2014. Cell Rep. 8:371-381.
98. Wang, P., et al 2014. Basic Res. Cardiol. 109:435.
99. von, G. A., et al 2012. Proc. Natl. Acad. Sci. U.S.A 109:2394-2399.
100. Dong, J., et al. 2007. Cell 130:1120-1133.
101. Esteve, P. O., et al. 2005. Proc. Natl. Acad. Sci. U.S.A 102:1000-1005.
102. Choi, B. H., et al. 2015. Genes Cancer 6:371-377.
103. Liu, Y., et al. 2010. Am. J. Physiol Heart Circ. Physiol 298:H2082-H2092.
104. Brattelid, T., et al. 2010. BMC. Mol. Biol. 11:22.
105. Kolwicz, S. C., Jr., et al. 2013. Circ. Res. 113:603-616.
106. Anversa, P., et al. 1990. Circ. Res. 67:871-885.
107. Schnell, U., et al. 2012. Nat. Methods 9:152-158.

Throughout this application various publications are referenced. The disclosures of these publications in their entireties are hereby incorporated by reference into this application in order to describe more fully the state of the art to which this invention pertains.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. An expression vector comprising:
   (a) a nucleic acid sequence encoding lysine-specific demethylase 4D (KDM4D);
   (b) a cardiac-specific promoter capable of effecting overexpression of KDM4D only in cardiac tissue, wherein the promoter is operably linked to the nucleic acid sequence; and
   (c) a regulatory element that inducibly represses the overexpression of KDM4D.

2. The expression vector of claim 1, wherein the regulatory element is a tetracycline responsive element.

3. The vector of claim 1, wherein the vector is a viral vector that infects quiescent cells.

4. The vector of claim 3, wherein the viral vector is an adeno-associated virus (AAV) vector.

5. A method for inducing cardiac myocyte (CM) hyperplasia in a mammal comprising:
   administering the expression vector of claim 4 to the mammal.

6. A method for inducing cardiac myocyte (CM) hyperplasia in a mammal comprising:
   grafting CMs to the heart of the mammal, wherein the CMs contain the expression vector of claim 4.

7. A cardiac myocyte that comprises the expression vector of claim 1.

8. The cardiac myocyte of claim 7, which is an adult cardiac myocyte.

9. A cardiac myocyte that comprises the expression vector of claim 4.

10. The vector of claim 4, wherein the AAV vector is AAV6.

11. The vector of claim 4, wherein the AAV vector is AAV9.

12. The vector of claim 1, wherein the nucleic acid sequence encodes the KDM4D amino acid sequence of SEQ ID NO:1.

* * * * *